(12) United States Patent
Stevenson et al.

(10) Patent No.: US 10,350,421 B2
(45) Date of Patent: Jul. 16, 2019

(54) METALLURGICALLY BONDED GOLD POCKET PAD FOR GROUNDING AN EMI FILTER TO A HERMETIC TERMINAL FOR AN ACTIVE IMPLANTABLE MEDICAL DEVICE

(71) Applicant: Greatbatch Ltd., Clarence, NY (US)

(72) Inventors: Robert A. Stevenson, Canyon Country, CA (US); Christine A. Frysz, Orchard Park, NY (US); Jason Woods, Carson City, NV (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 15/943,998

(22) Filed: Apr. 3, 2018

(65) Prior Publication Data
US 2018/0236244 A1 Aug. 23, 2018

Related U.S. Application Data

(63) Continuation-in-part of application No. 15/797,278, filed on Oct. 30, 2017, and a continuation-in-part of
(Continued)

(51) Int. Cl.
*A61N 1/00* (2006.01)
*A61N 1/375* (2006.01)
(Continued)

(52) U.S. Cl.
CPC ........... *A61N 1/3754* (2013.01); *A61N 1/378* (2013.01); *H01R 4/58* (2013.01); *H01R 13/26* (2013.01);
(Continued)

(58) Field of Classification Search
CPC .. A61N 1/3754; A61N 1/37512; A61N 1/378; H01R 4/58; H01R 13/26;
(Continued)

(56) References Cited

U.S. PATENT DOCUMENTS

| 3,681,612 A | 8/1972 | Kinzler et al. |
| 3,745,430 A | 7/1973 | Kerr et al. |

(Continued)

FOREIGN PATENT DOCUMENTS

| EP | 0243573 | 11/1987 |
| EP | 0145430 | 5/1991 |

(Continued)

OTHER PUBLICATIONS

Lamouri, et al., "Control of the y-alumina to a-alumina phase transformation for an optimized alumina densification", Boletin de la Sociedad Espanola De Ceramica Y Vidrio 56 (2017) pp. 47-54.
(Continued)

*Primary Examiner* — Lindsey G Wehrheim
(74) *Attorney, Agent, or Firm* — Michael F. Scalise; Marc G. Martino

(57) ABSTRACT

A feedthrough subassembly for an active implantable medical device includes a metallic ferrule having a conductive ferrule body, at least one surface disposed on a device side, and a ferrule opening passing through the at least one surface. An insulator body hermetically seals the ferrule opening of the conductive ferrule body by at least one of a first gold braze ceramic seal, a glass seal or a glass-ceramic seal. At least one hermetically sealed conductive pathway is disposed through the insulator body. At least one pocket formed in the at least one surface has a gold pocket pad disposed within. When the first gold braze ceramic seal is present, the first gold braze ceramic seal and the gold pocket pad are not physically touching one another.

25 Claims, 43 Drawing Sheets

Related U.S. Application Data application No. 15/603,521, filed on May 24, 2017, and a continuation-in-part of application No. 15/250,210, filed on Aug. 29, 2016, now Pat. No. 9,931,514, which is a continuation-in-part of application No. 14/826,229, filed on Aug. 14, 2015, now Pat. No. 9,427,596, which is a continuation-in-part of application No. 14/202,653, filed on Mar. 10, 2014, now Pat. No. 9,108,066.

(60) Provisional application No. 61/841,419, filed on Jun. 30, 2013, provisional application No. 62/646,552, filed on Mar. 22, 2018.

(51) Int. Cl.
*A61N 1/378* (2006.01)
*H01R 13/52* (2006.01)
*H01R 4/58* (2006.01)
*H01R 13/26* (2006.01)
*H03H 1/00* (2006.01)

(52) U.S. Cl.
CPC ..... *H01R 13/5221* (2013.01); *H01R 13/5224* (2013.01); *A61N 1/37512* (2017.08); *H01R 2201/12* (2013.01); *H03H 2001/0014* (2013.01); *H03H 2001/0021* (2013.01); *H03H 2001/0042* (2013.01)

(58) Field of Classification Search
CPC ............ H01R 13/5221; H01R 13/5224; H01R 2201/12; H03H 2001/0014; H03H 2001/0021
See application file for complete search history.

(56) References Cited

U.S. PATENT DOCUMENTS

| | | |
|---|---|---|
| 3,871,382 A | 3/1975 | Mann |
| 3,961,294 A | 6/1976 | Hollyday |
| 3,968,802 A | 7/1976 | Ballis |
| 3,980,975 A | 9/1976 | Maxon et al. |
| 4,188,598 A | 2/1980 | Hunt |
| 4,236,127 A | 11/1980 | Scherba |
| 4,295,467 A | 10/1981 | Mann et al. |
| 4,320,763 A | 3/1982 | Money |
| 4,424,551 A | 1/1984 | Stevenson et al. |
| 4,431,005 A | 2/1984 | McCormick |
| 4,437,474 A | 3/1984 | Peers-Trevarton et al. |
| 4,445,501 A | 5/1984 | Bresler |
| 4,572,198 A | 2/1986 | Codrington |
| 4,585,001 A | 4/1986 | Belt |
| 4,633,181 A | 12/1986 | Murphy-Boesch et al. |
| 4,643,186 A | 2/1987 | Rosen et al. |
| 4,654,880 A | 3/1987 | Sontag |
| 4,672,972 A | 6/1987 | Berke |
| 4,689,621 A | 8/1987 | Kleinberg |
| 4,712,555 A | 12/1987 | Thornander et al. |
| 4,746,864 A | 5/1988 | Satoh et al. |
| 4,754,752 A | 7/1988 | Ginsburg et al. |
| 4,757,820 A | 7/1988 | Itoh |
| 4,766,381 A | 8/1988 | Conturo et al. |
| 4,788,980 A | 12/1988 | Mann et al. |
| 4,799,499 A | 1/1989 | Bisping |
| 4,813,429 A | 3/1989 | Eshel et al. |
| 4,823,812 A | 4/1989 | Eshel et al. |
| 4,832,023 A | 5/1989 | Murphy-Chutorian et al. |
| 4,858,064 A | 8/1989 | Segawa et al. |
| 4,858,623 A | 8/1989 | Bradshaw et al. |
| 4,859,950 A | 8/1989 | Keren |
| 4,932,411 A | 6/1990 | Fritschy et al. |
| 4,940,052 A | 7/1990 | Mann et al. |
| 4,944,298 A | 7/1990 | Sholder |
| 4,960,106 A | 10/1990 | Kubokawa et al. |
| 4,989,608 A | 2/1991 | Ratner |
| 4,991,580 A | 2/1991 | Moore |
| 5,019,075 A | 5/1991 | Spears et al. |
| 5,039,965 A | 8/1991 | Higgins |
| 5,044,375 A | 9/1991 | Bach et al. |
| 5,052,404 A | 10/1991 | Hodgson et al. |
| 5,063,348 A | 11/1991 | Kuhara et al. |
| 5,095,911 A | 3/1992 | Pomeranz |
| 5,099,208 A | 3/1992 | Fitzpatrick et al. |
| 5,167,233 A | 12/1992 | Eberle et al. |
| 5,178,618 A | 1/1993 | Kandarpa |
| 5,190,046 A | 3/1993 | Shturman |
| 5,197,468 A | 3/1993 | Proctor et al. |
| 5,209,233 A | 5/1993 | Holland et al. |
| 5,211,165 A | 5/1993 | Dumoulin et al. |
| 5,217,010 A | 6/1993 | Tsitlik et al. |
| 5,222,506 A | 6/1993 | Patrick et al. |
| 5,246,438 A | 9/1993 | Langberg |
| 5,251,120 A | 10/1993 | Smith |
| 5,268,810 A | 12/1993 | DiMarco et al. |
| 5,271,400 A | 12/1993 | Dumoulin et al. |
| 5,300,108 A | 4/1994 | Rebell et al. |
| 5,306,291 A | 4/1994 | Kroll et al. |
| 5,307,808 A | 5/1994 | Dumoulin et al. |
| 5,307,814 A | 5/1994 | Kressel et al. |
| 5,318,025 A | 6/1994 | Dumoulin et al. |
| 5,323,776 A | 6/1994 | Blakeley et al. |
| 5,323,778 A | 6/1994 | Kandarpa et al. |
| 5,331,505 A | 7/1994 | Wilheim |
| 5,333,095 A | 7/1994 | Stevenson et al. |
| 5,334,045 A | 8/1994 | Cappa et al. |
| 5,334,193 A | 8/1994 | Nardella |
| 5,348,010 A | 9/1994 | Schnall et al. |
| 5,352,979 A | 10/1994 | Conturo |
| 5,358,515 A | 10/1994 | Hurter et al. |
| 5,363,845 A | 11/1994 | Chowdhury et al. |
| 5,365,928 A | 11/1994 | Rhinehart et al. |
| 5,370,644 A | 12/1994 | Langberg |
| 5,398,683 A | 3/1995 | Edwards et al. |
| 5,400,787 A | 3/1995 | Marandos |
| 5,404,880 A | 4/1995 | Throne |
| 5,413,104 A | 5/1995 | Buijs et al. |
| 5,419,325 A | 5/1995 | Dumoulin et al. |
| 5,428,337 A | 6/1995 | Vinclarelli et al. |
| 5,433,717 A | 7/1995 | Rubinsky et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,447,156 A | 9/1995 | Dumoulin et al. |
| 5,450,090 A | 9/1995 | Gels et al. |
| 5,451,232 A | 9/1995 | Rhinehart et al. |
| 5,462,055 A | 10/1995 | Casey et al. |
| 5,466,254 A | 11/1995 | Helland |
| 5,476,095 A | 12/1995 | Schnall et al. |
| 5,476,483 A | 12/1995 | Bornzin et al. |
| 5,491,300 A | 2/1996 | Huppenthal et al. |
| 5,493,259 A | 2/1996 | Blalock et al. |
| 5,498,261 A | 3/1996 | Strul |
| 5,507,743 A | 4/1996 | Edwards et al. |
| 5,512,825 A | 4/1996 | Atalar et al. |
| 5,514,173 A | 5/1996 | Rebell et al. |
| 5,540,679 A | 7/1996 | Fram et al. |
| 5,545,201 A | 8/1996 | Helland et al. |
| 5,558,093 A | 9/1996 | Pomeranz |
| 5,578,008 A | 11/1996 | Hara |
| 5,588,432 A | 12/1996 | Crowley |
| 5,590,657 A | 1/1997 | Cain et al. |
| 5,591,218 A | 1/1997 | Jacobson |
| 5,620,476 A | 4/1997 | Truex et al. |
| 5,623,241 A | 4/1997 | Minkoff |
| 5,623,724 A | 4/1997 | Gurkovich et al. |
| 5,629,622 A | 5/1997 | Scampini |
| 5,650,759 A | 7/1997 | Hittman et al. |
| 5,662,108 A | 9/1997 | Budd et al. |
| 5,682,897 A | 11/1997 | Pomeranz |
| 5,683,435 A | 11/1997 | Truex et al. |
| 5,685,878 A | 11/1997 | Falwell et al. |
| 5,697,958 A | 12/1997 | Paul et al. |
| 5,699,801 A | 12/1997 | Atalar et al. |

(56) References Cited

U.S. PATENT DOCUMENTS

| | | |
|---|---|---|
| 5,700,548 A | 12/1997 | Warnier et al. |
| 5,706,810 A | 1/1998 | Rubinsky et al. |
| 5,715,825 A | 2/1998 | Crowley |
| 5,716,390 A | 2/1998 | Li |
| 5,722,998 A | 3/1998 | Prutchi et al. |
| 5,735,884 A | 4/1998 | Thompson et al. |
| 5,735,887 A | 4/1998 | Barreras et al. |
| 5,741,321 A | 4/1998 | Brennen |
| 5,751,539 A | 5/1998 | Stevenson et al. |
| 5,757,252 A | 5/1998 | Cho et al. |
| 5,759,202 A | 6/1998 | Schroeppel |
| 5,765,779 A | 6/1998 | Hancock et al. |
| 5,769,800 A | 6/1998 | Gelfand et al. |
| 5,772,693 A | 6/1998 | Brownlee |
| 5,775,338 A | 7/1998 | Hastings |
| 5,779,669 A | 7/1998 | Haissaguerre et al. |
| 5,782,891 A | 7/1998 | Hassler et al. |
| 5,792,055 A | 8/1998 | McKinnon |
| 5,800,467 A | 9/1998 | Park et al. |
| 5,822,174 A | 10/1998 | Yamate et al. |
| 5,824,026 A | 10/1998 | Diaz et al. |
| 5,824,029 A | 10/1998 | Weijand et al. |
| 5,833,608 A | 11/1998 | Acker |
| 5,836,992 A | 11/1998 | Thompson et al. |
| 5,840,031 A | 11/1998 | Crowley |
| 5,851,226 A | 12/1998 | Skubitz et al. |
| 5,855,995 A | 1/1999 | Haq et al. |
| 5,864,234 A | 1/1999 | Luedeke |
| 5,867,361 A | 2/1999 | Seifried et al. |
| 5,868,674 A | 2/1999 | Glowinski et al. |
| 5,879,347 A | 3/1999 | Saadat |
| 5,891,134 A | 4/1999 | Goble et al. |
| 5,896,267 A | 4/1999 | Hittman et al. |
| 5,905,627 A | 5/1999 | Brendel et al. |
| 5,916,162 A | 6/1999 | Snelten et al. |
| 5,928,145 A | 7/1999 | Ocali et al. |
| 5,928,159 A | 7/1999 | Eggers et al. |
| 5,929,729 A | 7/1999 | Swarup |
| 5,938,609 A | 8/1999 | Pomeranz |
| 5,938,692 A | 8/1999 | Rudie |
| 5,959,336 A | 9/1999 | Barsan |
| 5,959,829 A | 9/1999 | Stevenson et al. |
| 5,964,705 A | 10/1999 | Truwit et al. |
| 5,973,906 A | 10/1999 | Stevenson et al. |
| 5,973,907 A | 10/1999 | Reed |
| 5,978,204 A | 11/1999 | Stevenson |
| 6,004,269 A | 12/1999 | Crowley et al. |
| 6,008,980 A | 12/1999 | Stevenson et al. |
| 6,011,995 A | 1/2000 | Guglielmi et al. |
| 6,026,316 A | 2/2000 | Kucharczyk et al. |
| 6,027,500 A | 2/2000 | Buckles et al. |
| 6,031,375 A | 2/2000 | Atalar et al. |
| 6,031,710 A | 2/2000 | Wolf et al. |
| 6,041,496 A | 3/2000 | Haq et al. |
| 6,045,532 A | 4/2000 | Eggers et al. |
| 6,052,614 A | 4/2000 | Morris et al. |
| 6,055,457 A | 4/2000 | Bonner |
| 6,066,136 A | 5/2000 | Geistert |
| 6,099,524 A | 8/2000 | Lipson et al. |
| 6,101,417 A | 8/2000 | Vogel et al. |
| 6,128,522 A | 10/2000 | Acker et al. |
| 6,129,670 A | 10/2000 | Burdette et al. |
| 6,137,161 A | 10/2000 | Gilliland et al. |
| 6,141,594 A | 10/2000 | Flynn et al. |
| 6,146,743 A | 11/2000 | Haq et al. |
| 6,159,560 A | 12/2000 | Stevenson et al. |
| 6,171,240 B1 | 1/2001 | Young et al. |
| 6,171,241 B1 | 1/2001 | McVeigh et al. |
| 6,188,219 B1 | 2/2001 | Reeder et al. |
| 6,198,972 B1 | 3/2001 | Hartlaub et al. |
| 6,209,764 B1 | 4/2001 | Hartlaub et al. |
| 6,226,545 B1 | 5/2001 | Gilderdale |
| 6,236,205 B1 | 5/2001 | Lüdeke et al. |
| 6,238,390 B1 | 5/2001 | Tu et al. |
| 6,252,761 B1 | 6/2001 | Branchevsky |
| 6,263,229 B1 | 7/2001 | Atalar et al. |
| 6,272,370 B1 | 8/2001 | Gillies et al. |
| 6,275,369 B1 | 8/2001 | Stevenson et al. |
| 6,275,379 B1 | 8/2001 | Sleboda et al. |
| 6,280,385 B1 | 8/2001 | Melzer et al. |
| 6,284,080 B1 | 9/2001 | Haq et al. |
| 6,284,971 B1 | 9/2001 | Atalar et al. |
| 6,332,089 B1 | 12/2001 | Acker et al. |
| 6,370,427 B1 | 4/2002 | Alt et al. |
| 6,373,673 B1 | 4/2002 | Anthony |
| 6,390,996 B1 | 5/2002 | Halperin et al. |
| 6,395,637 B1 | 5/2002 | Park et al. |
| 6,408,202 B1 | 6/2002 | Lima et al. |
| 6,414,835 B1 | 7/2002 | Wolf et al. |
| 6,424,234 B1 | 7/2002 | Stevenson |
| 6,428,537 B1 | 8/2002 | Swanson et al. |
| 6,433,653 B1 | 8/2002 | Matsumura et al. |
| 6,456,481 B1 | 9/2002 | Stevenson |
| 6,459,935 B1 | 10/2002 | Piersma |
| 6,470,545 B1 | 10/2002 | Branchevsky |
| 6,473,291 B1 | 10/2002 | Stevenson |
| 6,473,314 B1 | 10/2002 | Custer et al. |
| 6,486,529 B2 | 11/2002 | Chi et al. |
| 6,493,591 B1 | 12/2002 | Stokes |
| 6,512,666 B1 | 1/2003 | Duva |
| 6,529,103 B1 | 3/2003 | Brendel et al. |
| 6,535,766 B1 | 3/2003 | Thompson et al. |
| 6,539,253 B2 | 3/2003 | Thompson et al. |
| 6,539,261 B2 | 3/2003 | Dal Molin |
| 6,549,800 B1 | 4/2003 | Atalar et al. |
| 6,556,009 B2 | 4/2003 | Kellman et al. |
| 6,566,978 B2 | 5/2003 | Stevenson et al. |
| 6,567,259 B2 | 5/2003 | Stevenson et al. |
| 6,567,703 B1 | 5/2003 | Thompson et al. |
| 6,593,884 B1 | 7/2003 | Gilboa et al. |
| 6,606,513 B2 | 8/2003 | Lardo et al. |
| 6,615,483 B2 | 9/2003 | Lindegren |
| 6,628,980 B2 | 9/2003 | Atalar et al. |
| 6,633,780 B1 | 10/2003 | Berger |
| 6,643,903 B2 | 11/2003 | Stevenson et al. |
| 6,654,628 B1 | 11/2003 | Silber et al. |
| 6,660,116 B2 | 12/2003 | Wolf |
| 6,675,033 B1 | 1/2004 | Lardo et al. |
| 6,675,036 B2 | 1/2004 | Kreger et al. |
| 6,675,779 B2 | 1/2004 | King et al. |
| 6,675,780 B1 | 1/2004 | Wendels et al. |
| 6,687,550 B1 | 2/2004 | Doan |
| 6,690,963 B2 | 2/2004 | Ben-Haim et al. |
| 6,694,583 B2 | 2/2004 | Branchevsky |
| 6,697,675 B1 | 2/2004 | Safarevich et al. |
| 6,701,176 B1 | 3/2004 | Halperin et al. |
| 6,714,809 B2 | 3/2004 | Lee et al. |
| 6,728,575 B2 | 4/2004 | Hedberg |
| 6,728,579 B1 | 4/2004 | Lindgren et al. |
| 6,759,388 B1 | 7/2004 | Marchant et al. |
| 6,765,779 B2 | 7/2004 | Stevenson |
| 6,765,780 B2 | 7/2004 | Brendel et al. |
| 6,768,630 B2 | 7/2004 | Togashi |
| 6,771,067 B2 | 8/2004 | Kellman et al. |
| 6,795,730 B2 | 9/2004 | Connelly et al. |
| 6,806,806 B2 | 10/2004 | Anthony |
| 6,823,215 B2 | 11/2004 | Obel et al. |
| 6,829,509 B1 | 12/2004 | MacDonald et al. |
| 6,847,837 B1 | 1/2005 | Melzer et al. |
| 6,868,288 B2 | 3/2005 | Thompson |
| 6,871,091 B2 | 3/2005 | Wilkinson et al. |
| 6,876,885 B2 | 4/2005 | Swoyer et al. |
| 6,882,248 B2 | 4/2005 | Stevenson et al. |
| 6,888,715 B2 | 5/2005 | Stevenson et al. |
| 6,898,454 B2 | 5/2005 | Atalar et al. |
| 6,901,292 B2 | 5/2005 | Hrdlicka et al. |
| 6,904,307 B2 | 6/2005 | Karmarkar et al. |
| 6,925,328 B2 | 8/2005 | Foster et al. |
| 6,930,242 B1 | 8/2005 | Helfer et al. |
| 6,931,283 B1 | 8/2005 | Magnusson |
| 6,931,286 B2 | 8/2005 | Sigg et al. |
| 6,934,588 B1 | 8/2005 | Brand et al. |
| 6,944,489 B2 | 9/2005 | Zeijlemaker et al. |
| 6,944,507 B2 | 9/2005 | Fröberg et al. |

(56) References Cited

U.S. PATENT DOCUMENTS

| | | |
|---|---|---|
| 6,949,929 B2 | 9/2005 | Gray et al. |
| 6,950,696 B2 | 9/2005 | Björling et al. |
| 6,952,613 B2 | 10/2005 | Swoyer et al. |
| 6,971,391 B1 | 12/2005 | Wang et al. |
| 6,985,347 B2 | 1/2006 | Stevenson et al. |
| 6,985,775 B2 | 1/2006 | Reinke et al. |
| 6,987,660 B2 | 1/2006 | Stevenson et al. |
| 6,999,818 B2 | 2/2006 | Stevenson et al. |
| 7,012,192 B2 | 3/2006 | Stevenson et al. |
| 7,013,180 B2 | 3/2006 | Dougherty et al. |
| 7,015,393 B2 | 3/2006 | Weiner et al. |
| 7,035,076 B1 | 4/2006 | Stevenson |
| 7,038,900 B2 | 5/2006 | Stevenson et al. |
| 7,039,455 B1 | 5/2006 | Brosovich et al. |
| 7,046,499 B1 | 5/2006 | Imani et al. |
| 7,047,073 B2 | 5/2006 | Höijer et al. |
| 7,050,855 B2 | 5/2006 | Zeijlemaker et al. |
| 7,068,491 B1 | 6/2006 | Burdon et al. |
| 7,091,412 B2 | 8/2006 | Wang et al. |
| 7,092,766 B1 | 8/2006 | Salys et al. |
| 7,110,227 B2 | 9/2006 | Anthony et al. |
| 7,113,387 B2 | 9/2006 | Stevenson et al. |
| 7,123,013 B2 | 10/2006 | Gray |
| 7,127,294 B1 | 10/2006 | Wang et al. |
| 7,136,273 B2 | 11/2006 | Stevenson et al. |
| 7,148,783 B2 | 12/2006 | Parsche et al. |
| 7,149,578 B2 | 12/2006 | Edvardsson |
| 7,149,773 B2 | 12/2006 | Haller et al. |
| 7,155,271 B2 | 12/2006 | Halperin et al. |
| 7,162,302 B2 | 1/2007 | Wang et al. |
| 7,164,572 B1 | 1/2007 | Burdon et al. |
| 7,164,950 B2 | 1/2007 | Kroll et al. |
| 7,174,219 B2 | 2/2007 | Wahlstrand et al. |
| 7,174,223 B2 | 2/2007 | Money et al. |
| 7,199,995 B2 | 4/2007 | Stevenson |
| 7,211,103 B2 | 5/2007 | Greenberg et al. |
| 7,236,816 B2 | 6/2007 | Kumar et al. |
| 7,236,834 B2 | 6/2007 | Christopherson et al. |
| 7,276,474 B2 | 10/2007 | Marchant et al. |
| 7,301,748 B2 | 11/2007 | Anthony et al. |
| 7,310,216 B2 | 12/2007 | Stevenson et al. |
| 7,319,905 B1 | 1/2008 | Morgan et al. |
| 7,322,832 B2 | 1/2008 | Kronich et al. |
| 7,327,553 B2 | 2/2008 | Brendel |
| 7,363,090 B2 | 4/2008 | Halperin et al. |
| 7,369,898 B1 | 5/2008 | Kroll et al. |
| 7,387,928 B2 | 6/2008 | Cheung |
| 7,388,378 B2 | 6/2008 | Gray et al. |
| 7,422,568 B2 | 9/2008 | Yang et al. |
| 7,423,860 B2 | 9/2008 | Anthony et al. |
| 7,428,136 B2 | 9/2008 | Barnett |
| 7,433,168 B2 | 10/2008 | Anthony |
| 7,436,672 B2 | 10/2008 | Ushijima et al. |
| 7,439,449 B1 | 10/2008 | Kumar et al. |
| 7,446,996 B2 | 11/2008 | Togashi |
| 7,450,396 B2 | 11/2008 | Ye et al. |
| 7,480,988 B2 | 1/2009 | Ok et al. |
| 7,489,495 B2 | 2/2009 | Stevenson |
| 7,495,884 B2 | 2/2009 | Togashi |
| 7,517,769 B2 | 4/2009 | Van Schuylenbergh et al. |
| 7,529,590 B2 | 5/2009 | MacDonald |
| 7,535,693 B2 | 5/2009 | Stevenson et al. |
| 7,551,963 B2 | 6/2009 | Rusin et al. |
| 7,561,906 B2 | 7/2009 | Atalar et al. |
| 7,586,728 B2 | 9/2009 | Anthony |
| 7,593,208 B2 | 9/2009 | Anthony et al. |
| 7,623,335 B2 | 11/2009 | Stevenson et al. |
| 7,675,729 B2 | 3/2010 | Anthony et al. |
| 7,679,926 B2 | 3/2010 | Hsu et al. |
| 7,689,288 B2 | 3/2010 | Stevenson et al. |
| 7,693,576 B1 | 4/2010 | Lavie et al. |
| 7,702,387 B2 | 4/2010 | Stevenson et al. |
| 7,719,854 B2 | 5/2010 | Youker et al. |
| 7,729,770 B2 | 6/2010 | Cabelka et al. |
| 7,733,621 B2 | 6/2010 | Anthony et al. |
| 7,797,048 B2 | 9/2010 | Stevenson et al. |
| 7,812,691 B1 | 10/2010 | Fisk et al. |
| 7,839,146 B2 | 11/2010 | Gray |
| 7,844,319 B2 | 11/2010 | Susil et al. |
| 7,844,343 B2 | 11/2010 | Wahlstrand et al. |
| 7,853,324 B2 | 12/2010 | Stevenson et al. |
| 7,899,551 B2 | 3/2011 | Westlund et al. |
| 7,901,761 B1 | 3/2011 | Jiang et al. |
| 7,957,806 B2 | 6/2011 | Stevenson et al. |
| 7,989,080 B2 | 8/2011 | Greenberg et al. |
| 8,000,804 B1 | 8/2011 | Wessendorf et al. |
| 8,043,454 B1 | 10/2011 | Jiang et al. |
| 8,095,224 B2 | 1/2012 | Truex et al. |
| 8,131,376 B1 | 3/2012 | Greenberg et al. |
| 8,163,397 B2 | 4/2012 | Ok et al. |
| 8,179,658 B2 | 5/2012 | Stevenson et al. |
| 8,219,208 B2 | 7/2012 | Stevenson et al. |
| 8,301,249 B2 | 10/2012 | Min |
| 8,494,635 B2 | 7/2013 | Guebler et al. |
| 8,528,201 B2 | 9/2013 | Guebler et al. |
| 8,588,916 B2 | 11/2013 | Satou et al. |
| 8,604,341 B2 | 12/2013 | Barry et al. |
| 8,653,384 B2 | 2/2014 | Tang et al. |
| 8,659,870 B2 | 2/2014 | Brendel et al. |
| 8,670,829 B2 | 3/2014 | Satou et al. |
| 8,755,887 B2 | 6/2014 | Troetzschel et al. |
| 8,763,245 B1 | 7/2014 | Lucisano et al. |
| 8,841,558 B2 | 9/2014 | Satou et al. |
| 8,855,768 B1 | 10/2014 | Dabney et al. |
| 8,872,035 B2 | 10/2014 | Satou et al. |
| 8,874,206 B2 | 10/2014 | Malinowski et al. |
| 8,886,320 B2 | 11/2014 | Wollenberg et al. |
| 8,927,862 B2 | 1/2015 | Barry et al. |
| 8,929,987 B2 | 1/2015 | Troetzschel et al. |
| 8,938,309 B2 | 1/2015 | Marzano et al. |
| 9,008,779 B2 | 4/2015 | Satou et al. |
| 9,032,614 B2 | 5/2015 | Specht |
| 9,108,066 B2 | 8/2015 | Woods et al. |
| 9,233,253 B2 | 1/2016 | Stevenson et al. |
| 9,407,076 B2 | 8/2016 | Troetzschel et al. |
| 9,418,778 B2 | 8/2016 | Makino et al. |
| 9,427,596 B2 | 8/2016 | Brendel et al. |
| 9,431,814 B2 | 8/2016 | Blilie et al. |
| 9,480,168 B2 | 10/2016 | Troetzschel et al. |
| 9,492,659 B2 | 11/2016 | Brendel et al. |
| 9,552,899 B2 | 1/2017 | Glynn et al. |
| 2002/0055678 A1 | 5/2002 | Scott et al. |
| 2002/0095197 A1 | 7/2002 | Lardo et al. |
| 2002/0177771 A1 | 11/2002 | Guttman et al. |
| 2002/0192688 A1 | 12/2002 | Yang et al. |
| 2003/0013928 A1 | 1/2003 | Saruwatari |
| 2003/0013948 A1 | 1/2003 | Russell |
| 2003/0028094 A1 | 2/2003 | Kumar et al. |
| 2003/0028095 A1 | 2/2003 | Tulley et al. |
| 2003/0050557 A1 | 3/2003 | Susil et al. |
| 2003/0053284 A1 | 3/2003 | Stevenson et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0144706 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0171792 A1 | 9/2003 | Zarinetchi et al. |
| 2003/0179536 A1 | 9/2003 | Stevenson et al. |
| 2003/0204217 A1 | 10/2003 | Greatbatch |
| 2003/0208252 A1 | 11/2003 | O" Boyle et al. |
| 2003/0212373 A1 | 11/2003 | Hall et al. |
| 2003/0213605 A1 | 11/2003 | Brendel et al. |
| 2004/0015079 A1 | 1/2004 | Berger et al. |
| 2004/0034338 A1 | 2/2004 | Thierfelder et al. |
| 2004/0088012 A1 | 5/2004 | Kroll et al. |
| 2004/0167392 A1 | 8/2004 | Halperin et al. |
| 2004/0210289 A1 | 10/2004 | Wang et al. |

(56) References Cited

U.S. PATENT DOCUMENTS

| | | |
|---|---|---|
| 2004/0230271 A1 | 11/2004 | Wang et al. |
| 2004/0249428 A1 | 12/2004 | Wang et al. |
| 2004/0263173 A1 | 12/2004 | Gray |
| 2004/0263174 A1 | 12/2004 | Gray et al. |
| 2005/0007718 A1 | 1/2005 | Stevenson et al. |
| 2005/0070972 A1 | 3/2005 | Wahlstrand et al. |
| 2005/0113669 A1 | 5/2005 | Helfer et al. |
| 2005/0113676 A1 | 5/2005 | Weiner et al. |
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0197677 A1 | 9/2005 | Stevenson |
| 2005/0201039 A1 | 9/2005 | Stevenson et al. |
| 2005/0215914 A1 | 9/2005 | Bornzin et al. |
| 2005/0222642 A1 | 10/2005 | Przybyszewski et al. |
| 2005/0222647 A1 | 10/2005 | Wahlstrand et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0247472 A1 | 11/2005 | Helfer et al. |
| 2005/0248340 A1 | 11/2005 | Berkcan et al. |
| 2005/0248907 A1 | 11/2005 | Stevenson et al. |
| 2006/0009819 A1 | 1/2006 | Przybyszewski |
| 2006/0025820 A1 | 2/2006 | Phillips et al. |
| 2006/0030774 A1 | 2/2006 | Gray et al. |
| 2006/0032665 A1 | 2/2006 | Ice |
| 2006/0041294 A1 | 2/2006 | Gray |
| 2006/0085043 A1 | 4/2006 | Stevenson |
| 2006/0100506 A1 | 5/2006 | Halperin et al. |
| 2006/0119361 A1 | 6/2006 | Karmarkar et al. |
| 2006/0200218 A1 | 9/2006 | Wahlstrand |
| 2006/0211979 A1 | 9/2006 | Smith et al. |
| 2006/0212096 A1 | 9/2006 | Stevenson |
| 2006/0221543 A1 | 10/2006 | Stevenson et al. |
| 2006/0229693 A1 | 10/2006 | Bauer et al. |
| 2006/0247684 A1 | 11/2006 | Halperin et al. |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0259093 A1 | 11/2006 | Stevenson et al. |
| 2006/0271138 A1 | 11/2006 | MacDonald |
| 2007/0035910 A1 | 2/2007 | Stevenson |
| 2007/0043399 A1 | 2/2007 | Stevenson et al. |
| 2007/0083244 A1 | 4/2007 | Stevenson et al. |
| 2007/0088416 A1 | 4/2007 | Atalar et al. |
| 2007/0093142 A1 | 4/2007 | MacDonald et al. |
| 2007/0106332 A1 | 5/2007 | Denker et al. |
| 2007/0112398 A1 | 5/2007 | Stevenson et al. |
| 2007/0123949 A1 | 5/2007 | Dabney et al. |
| 2007/0167867 A1 | 7/2007 | Wolf |
| 2007/0168005 A1 | 7/2007 | Gray |
| 2007/0168006 A1 | 7/2007 | Gray |
| 2007/0179554 A1 | 8/2007 | Iyer et al. |
| 2007/0179577 A1 | 8/2007 | Marshall et al. |
| 2007/0203529 A1 | 8/2007 | Iyer et al. |
| 2007/0208383 A1 | 9/2007 | Williams |
| 2007/0250143 A1 | 10/2007 | Sommer et al. |
| 2007/0255332 A1 | 11/2007 | Cabelka et al. |
| 2007/0255377 A1 | 11/2007 | Marshall et al. |
| 2007/0288058 A1 | 12/2007 | Halperin et al. |
| 2007/0299490 A1 | 12/2007 | Yang et al. |
| 2008/0004670 A1 | 1/2008 | McVenes et al. |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0049410 A1 | 2/2008 | Kawaguchi et al. |
| 2008/0051854 A1 | 2/2008 | Bulkes et al. |
| 2008/0071313 A1 | 3/2008 | Stevenson et al. |
| 2008/0116997 A1 | 5/2008 | Dabney et al. |
| 2008/0132986 A1 | 6/2008 | Gray et al. |
| 2008/0132987 A1 | 6/2008 | Westlund et al. |
| 2008/0140149 A1 | 6/2008 | John et al. |
| 2008/0158746 A1 | 7/2008 | Anthony et al. |
| 2008/0161886 A1 | 7/2008 | Stevenson et al. |
| 2008/0195180 A1 | 8/2008 | Stevenson et al. |
| 2008/0195186 A1 | 8/2008 | Li et al. |
| 2008/0195187 A1 | 8/2008 | Li et al. |
| 2008/0221638 A1 | 9/2008 | Wedan et al. |
| 2008/0239622 A1 | 10/2008 | Hsu et al. |
| 2008/0243218 A1 | 10/2008 | Bottomley et al. |
| 2008/0247111 A1 | 10/2008 | Anthony et al. |
| 2008/0247116 A1 | 10/2008 | Kawano et al. |
| 2008/0247117 A1 | 10/2008 | Elam et al. |
| 2008/0262584 A1 | 10/2008 | Bottomley et al. |
| 2008/0262592 A1 | 10/2008 | Jordan et al. |
| 2008/0264685 A1 | 10/2008 | Park et al. |
| 2008/0269591 A1 | 10/2008 | Halperin et al. |
| 2008/0277153 A1 | 11/2008 | Teshome et al. |
| 2009/0036944 A1 | 2/2009 | Fonte |
| 2009/0097219 A1 | 4/2009 | Cho et al. |
| 2009/0099440 A1 | 4/2009 | Viohl |
| 2009/0099555 A1 | 4/2009 | Viohl et al. |
| 2009/0107717 A1 | 4/2009 | Hsu et al. |
| 2009/0116167 A1 | 5/2009 | Stevenson et al. |
| 2009/0128976 A1 | 5/2009 | Anthony |
| 2009/0139760 A1 | 6/2009 | Tanaka |
| 2009/0163974 A1 | 6/2009 | Taylor et al. |
| 2009/0163980 A1 | 6/2009 | Stevenson |
| 2009/0180237 A1 | 7/2009 | Hou et al. |
| 2009/0187229 A1 | 7/2009 | Lavie |
| 2009/0236141 A1 | 9/2009 | Kim et al. |
| 2009/0243756 A1 | 10/2009 | Stevenson et al. |
| 2009/0270948 A1 | 10/2009 | Nghiem et al. |
| 2009/0281592 A1 | 11/2009 | Vase |
| 2009/0312835 A1 | 12/2009 | Stevenson |
| 2010/0010602 A1 | 1/2010 | Wedan et al. |
| 2010/0016936 A1 | 1/2010 | Stevenson et al. |
| 2010/0023000 A1 | 1/2010 | Stevenson et al. |
| 2010/0023095 A1 | 1/2010 | Stevenson et al. |
| 2010/0046135 A1 | 2/2010 | Niki et al. |
| 2010/0046137 A1 | 2/2010 | Adachi |
| 2010/0076538 A1 | 3/2010 | Desai et al. |
| 2010/0109958 A1 | 5/2010 | Haubrich et al. |
| 2010/0109966 A1 | 5/2010 | Mateychuk et al. |
| 2010/0114276 A1 | 5/2010 | Min et al. |
| 2010/0114277 A1 | 5/2010 | Zhao et al. |
| 2010/0138192 A1 | 6/2010 | Min |
| 2010/0149042 A1 | 6/2010 | Utsi et al. |
| 2010/0151113 A1 | 6/2010 | Shelton |
| 2010/0160989 A1 | 6/2010 | Legay |
| 2010/0174348 A1 | 7/2010 | Bulkes et al. |
| 2010/0174349 A1 | 7/2010 | Stevenson et al. |
| 2010/0198312 A1 | 8/2010 | Stevenson et al. |
| 2010/0217262 A1 | 8/2010 | Stevenson et al. |
| 2010/0217264 A1 | 8/2010 | Odom et al. |
| 2010/0217341 A1 | 8/2010 | John et al. |
| 2010/0234907 A1 | 9/2010 | Dobak |
| 2011/0043297 A1 | 2/2011 | Stevenson et al. |
| 2011/0248184 A1 | 10/2011 | Shah |
| 2013/0184796 A1 | 7/2013 | Marzano et al. |
| 2014/0168917 A1 | 6/2014 | Marzano et al. |
| 2014/0243944 A1 | 8/2014 | Stevenson et al. |
| 2015/0217111 A1 | 8/2015 | Stevenson et al. |
| 2015/0245468 A1 | 8/2015 | Barry et al. |
| 2015/0283374 A1 | 10/2015 | Kronmueller et al. |
| 2015/0314131 A1 | 11/2015 | Marzano et al. |
| 2016/0287883 A1 | 10/2016 | Barry et al. |

FOREIGN PATENT DOCUMENTS

| | | |
|---|---|---|
| EP | 0466424 | 1/1992 |
| EP | 0557127 | 8/1993 |
| EP | 0673621 | 9/1995 |
| EP | 0498996 | 3/1997 |
| EP | 1021730 | 4/2003 |
| EP | 0930509 | 3/2004 |
| EP | 1469910 | 12/2006 |
| EP | 1883449 | 1/2009 |
| EP | 2025361 | 2/2009 |
| JP | 60141034 | 7/1985 |
| JP | 61181925 | 8/1986 |
| JP | 62233905 | 10/1987 |
| JP | 4071536 | 3/1992 |

(56) References Cited

FOREIGN PATENT DOCUMENTS

| | | |
|---|---|---|
| JP | 6054823 | 3/1994 |
| JP | 06070902 | 3/1994 |
| JP | 6176962 | 6/1994 |
| JP | 7272975 | 10/1995 |
| JP | 9094238 | 4/1997 |
| JP | 11239572 | 9/1999 |
| JP | 2004254257 | 9/2004 |
| JP | 2004289760 | 10/2004 |
| JP | 2005117606 | 4/2005 |
| JP | 2007129565 | 5/2007 |
| WO | 8704080 | 7/1987 |
| WO | 9210213 | 6/1992 |
| WO | 9423782 | 10/1994 |
| WO | 9740396 | 10/1997 |
| WO | 9852461 | 11/1998 |
| WO | 9919739 | 4/1999 |
| WO | 0010456 | 3/2000 |
| WO | 0025672 | 5/2000 |
| WO | 02083016 | 10/2002 |
| WO | 2003037424 | 5/2003 |
| WO | 2003063946 | 8/2003 |
| WO | 2003063952 | 8/2003 |
| WO | 2003063953 | 8/2003 |
| WO | 2003063955 | 8/2003 |
| WO | 2003063956 | 8/2003 |
| WO | 2003063957 | 8/2003 |
| WO | 2005081784 | 9/2005 |
| WO | 2005102445 | 11/2005 |
| WO | 2005102446 | 11/2005 |
| WO | 2005102447 | 11/2005 |
| WO | 2005115531 | 12/2005 |
| WO | 2006093685 | 9/2006 |
| WO | 2007047966 | 4/2007 |
| WO | 2007089988 | 8/2007 |
| WO | 2007102893 | 9/2007 |
| WO | 2007145671 | 12/2007 |
| WO | 2008077037 | 6/2008 |
| WO | 2008111986 | 9/2008 |
| WO | 2010008833 | 1/2010 |
| WO | 2013/158552 | 10/2013 |

OTHER PUBLICATIONS

Luchinger, "Safety Aspects of Cardiac Pacemakers in Magnetic Resonance Imaging", A dissertation submitted to the Swiss Federal Institute of Technology Zurich, Switzerland, 2002.
Olenick, "Ultrathin Flexible Ceramics for Electronics Applications", www.ceramicindustry.com—Product Profile, Oct. 2016, pp. 30 and 31.
Roguin, et al., "Modem Pacemaker and Implantable Cardioverter/ Defibrillator systems Can Be Magnetic Resonance Imaging Safe", Journal of the American Heart Association, Aug. 4, 2004, 475-482.
Shellock, et al., "Comparative Analyses of MR-Induced Distal Heating in Novel Filtered Cardiac Pacing Leads UsingTwo Geometric Configurations", 17th Scientific Meeting & Exhibition of the International Society for Magnetic Resonance in Medicine, Honolulu, Hawaii, Apr. 2009, 3014.
Shellock, "MRI Issues for Neuromodulation Devices", Institute for Magnetic Resonance Safety Education, and Research (IMRSER).
Susil, et al., "Multifunctional Interventional Devices for MRI: A Combined Electrophysiology/MRI Catheter", 2002, 594-600.
Susil, et al., "U.S. Appl. No. 60/283,725", Multifunctional Interventional Devices for Use in MRI, Apr. 13, 2001.
Weiner, et al., "U.S. Appl. No. 60/269,817", Electromagnetic Interference immune Cardiac Assist System, Feb. 20, 2001.
Wilk, et al., "High-K Gate Dielectrics: Current Status and Materials Properties Considerations", Journal of Applied Physi s, vol. 89, No. 10, May 15, 2001, 5243-5275.
European Search Report, Application No. 12157697.9, dated Jul. 5, 2012.
Balanis, "Advanced Engineering Electromagnetics", 1989.
Becker, "Die Keimbildung Bei Der Ausscheidung in Metallischen Mischkristallen", Published in Annalen der Physik, Issue 5, vol. 32, 1938, pp. 128-140.
Clement, et al., "Estimation of Effective Lead Loop Area for Implantable Pulse Generators and Cardioverter/Defibrillators for Determination of Susceptibility to Radiated Electromagnetic Interference", AAMI EMC Task Force, Apr. 12, 2004, 10 pages.
Ennis, et al., "Cautions About the Use of Equivalent Series Resistance (ESR) in Specifying Capacitors", Mar. 8, 1993, 58-64.
European Search Report, Application No. 10167031.3, dated Sep. 19, 2012.
European Search Report, Application No. 10167045.3, dated Oct. 10, 2012.
Gabriel, et al., "The Dielectric Properties of Biological Tissues: Parametric Models for the Dielectric Spectrum of Tissues", Phys. Med. Bio. 41, 1996, 2271-2293.
Johnson, et al., "Characterization of the Relationship between MR-Induced Distal Tip Heating in Cardiac Pacing Leads and Electrical Performance of Novel Filtered Tip Assemblies", 17th Scientific Meeting & Exhibition of the International Society for Magnetic Resonance in Medicine, Honolulu, Hawaii, Apr. 2009, 307.
Karbasi, "Developing a High Density PT/Alumina Hermetic Feedthrough", Florida International University, FIU Digital Commons, FIU Electronic Theses and Dissertations, University Graduate School, Published Jun. 15, 2012.
Kingery, et al., "Atom Mobility in Introduction to Ceramics, 2nd Edition", Published in New York, Wiley, copyright 1976, pp. 217-263.
Kingery, et al., "Surfaces, Interfaces, and Grain Boundaries in Introduction to Ceramics", 2nd Edition, Published in New York, Wiley, copyright 1976, pp. 177-215.
Konings, et al., "Heating Around Intravascular Guidewires by Resonating RF Waves", Journal of Magnetic Resonance Imaging, 2000, 79-85.

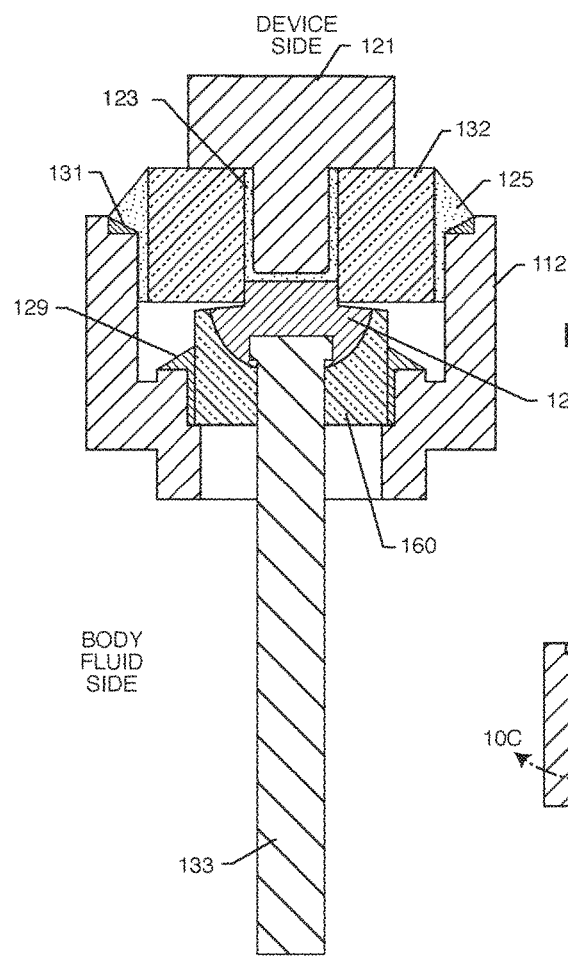
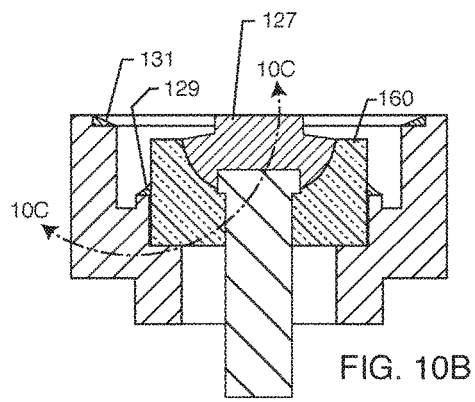
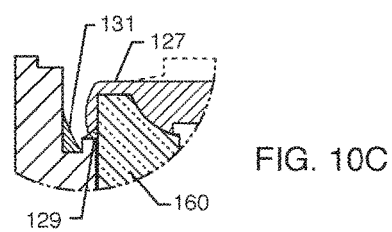

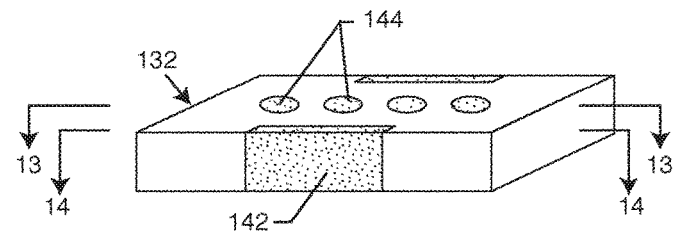
FIG. 11
PRIOR ART
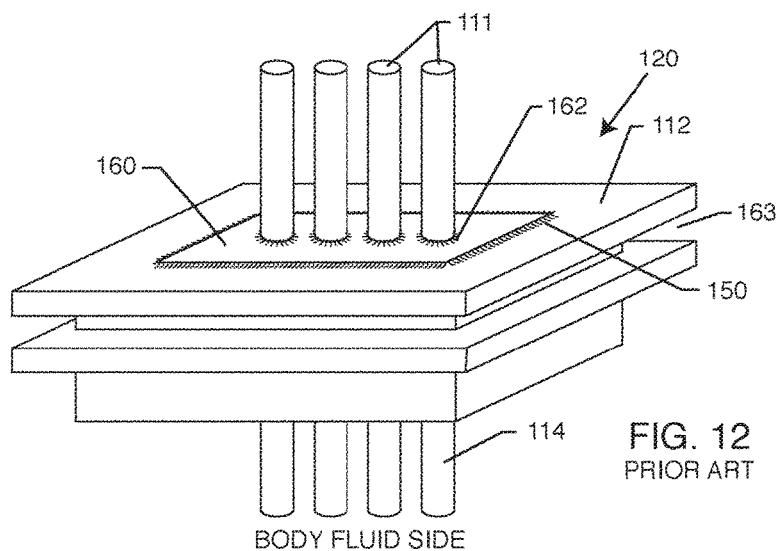
BODY FLUID SIDE
FIG. 12
PRIOR ART
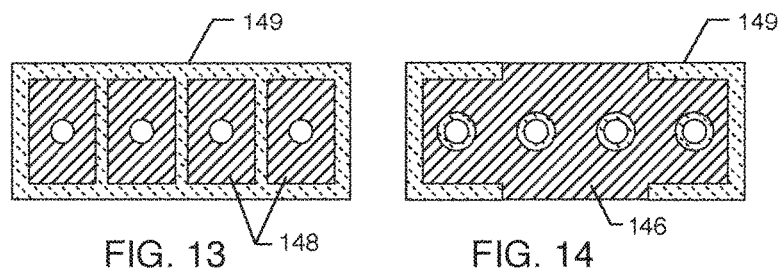
FIG. 13
PRIOR ART
FIG. 14
PRIOR ART

BODY FLUID SIDE
PRIOR ART

BODY FLUID SIDE
PRIOR ART

BODY FLUID SIDE

BODY FLUID SIDE

BODY FLUID SIDE

BODY FLUID SIDE

BODY FLUID SIDE

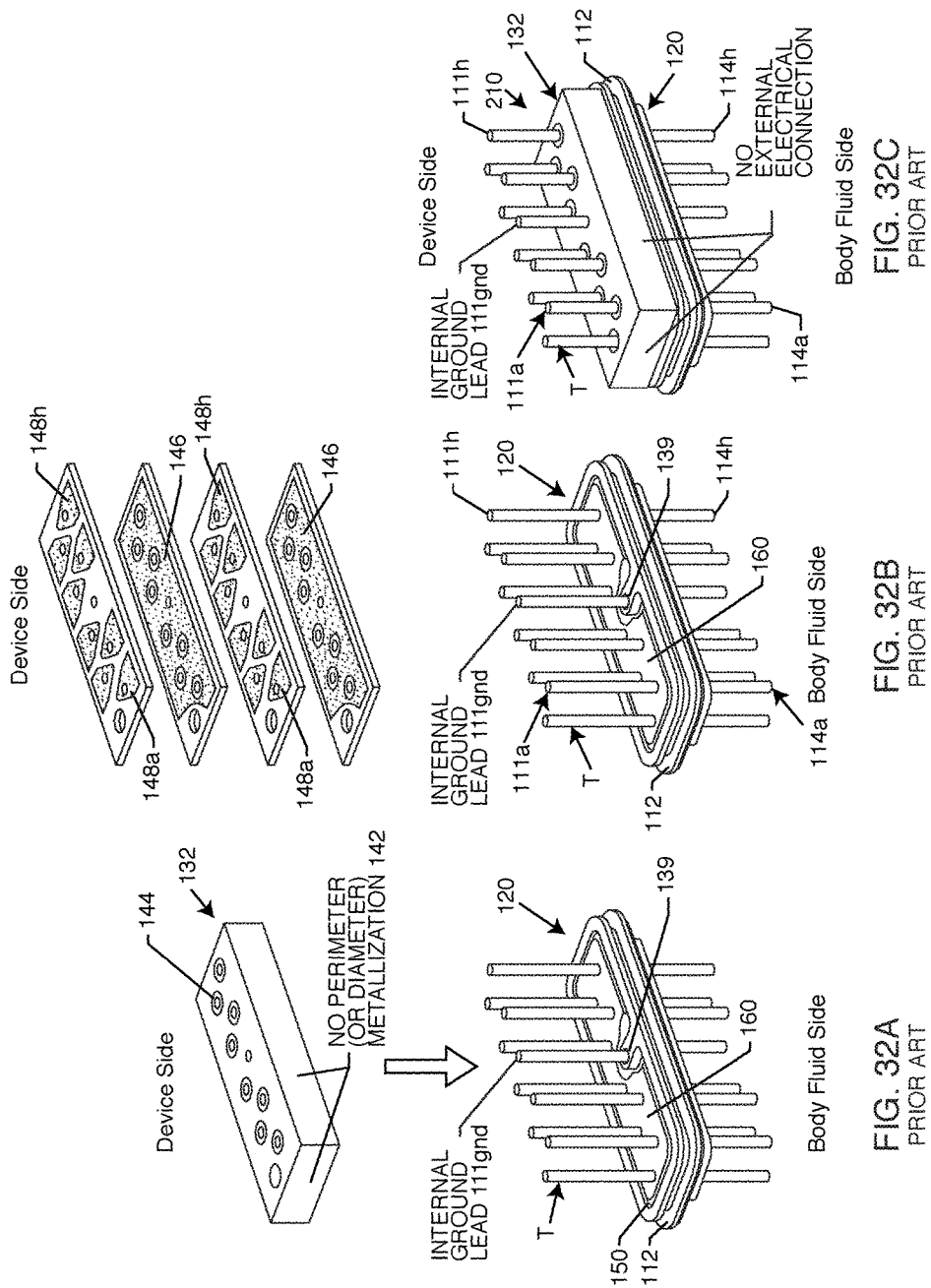

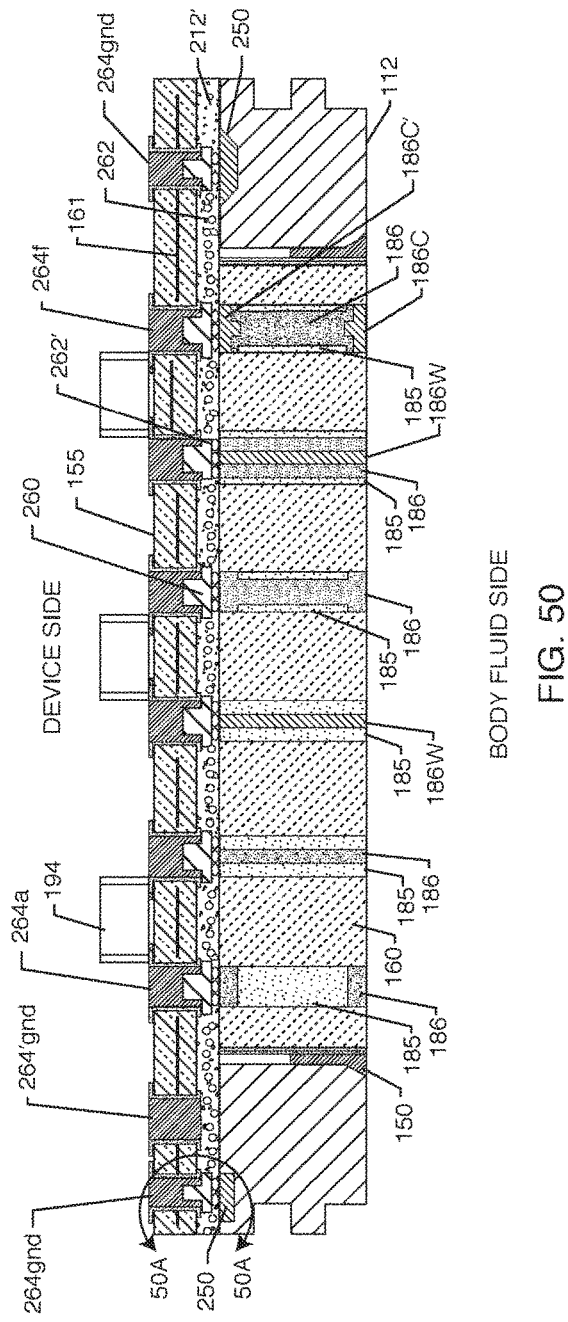
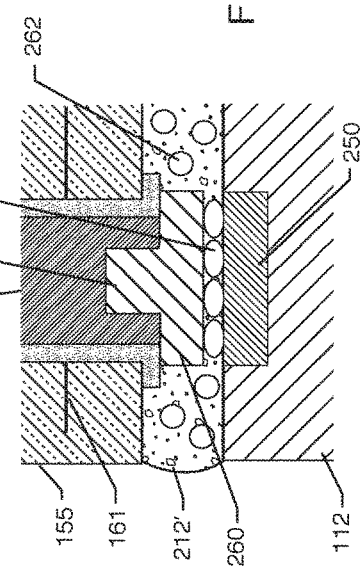
FIG. 50
FIG. 50A

METALLURGICALLY BONDED GOLD POCKET PAD FOR GROUNDING AN EMI FILTER TO A HERMETIC TERMINAL FOR AN ACTIVE IMPLANTABLE MEDICAL DEVICE

CROSS-REFERENCE TO RELATED APPLICATIONS

This continuation-in-part application claims priority to: U.S. provisional patent application Ser. No. 62/646,552, filed on Mar. 22, 2018, U.S. patent application Ser. No. 15/797,278, filed on Oct. 30, 2017, U.S. patent application Ser. No. 15/603,521, filed on May 24, 2017, and U.S. patent application Ser. No. 15/250,210, filed on Aug. 29, 2016, which claims priority to U.S. patent application Ser. No. 14/826,229, filed on Aug. 14, 2015, now U.S. Pat. No. 9,427,596, issued on Aug. 30, 2016, which claims priority to U.S. patent application Ser. No. 14/202,653, filed on Mar. 10, 2014, now U.S. Pat. No. 9,108,066, issued on Aug. 18, 2015, which claims priority to U.S. provisional application Ser. No. 61/841,419, filed on Jun. 30, 2013; the contents of which are fully incorporated herein with these references.

FIELD OF THE INVENTION

The present invention generally relates to active implantable medical devices and hermetic terminal subassemblies. More particularly, the present invention relates to a hermetic terminal for an active implantable medical device having a pocket formed in the ferrule to capture a gold preform that is reflowed at elevated temperatures (such as in a gold braze furnace) so that a reliable and oxide-resistant attachment to a capacitor can be made.

BACKGROUND OF THE INVENTION

FIG. 1 illustrates various types of active implantable and external medical devices 100 that are currently in use. FIG. 1 is a wire formed diagram of a generic human body showing a number of implanted medical devices. 100A is a family of external and implantable hearing devices which can include the group of hearing aids, cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of a seizure and also providing electrical stimulation to brain tissue to prevent the seizure from actually happening. The lead wires that come from a deep brain stimulator are often placed using real time imaging. Most commonly such lead wires are placed during real time MRI. 100C shows a cardiac pacemaker, which is well-known in the art, may have endocardial or epicardial leads. Implantable pacemakers may also be leadless. The family of cardiac pacemakers 100C includes the cardiac resynchronization therapy devices (CRT-D pacemakers) and leadless pacemakers. CRT-D pacemakers are unique in that, they pace both the right and left sides of the heart. The family also includes all types of implantable loop recorders or biologic monitors, such as cardiac monitors. 100D includes the family of left ventricular assist devices (LVAD's) and artificial hearts. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. 100F includes a variety of external or implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillator (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator, a Holter monitor with skin electrodes or even a ventricular assist device power pack. Referring once again to element 100C, the cardiac pacemaker could also be any type of biologic monitoring and/or data recording device. This would include loop recorders or the like. Referring once again to FIG. 1, 100I is described as an implantable defibrillator. It should be noted that these could be defibrillators with either endocardial or epicardial leads. This also includes a new family of subcutaneous defibrillators. ICDs, as used herein, include subcutaneous defibrillators and also CRT-D devices. CRT devices are cardiac resynchronization therapy devices that could also provide high-voltage defibrillation. In summary, as used herein, the term AIMD includes any device implanted in the human body that has at least one electronic component.

FIG. 2 illustrates a prior art cardiac pacemaker 100C showing a side view. The pacemaker electronics are housed in a hermetically sealed and conductive electromagnetic shield 102 (typically titanium). There is a header block assembly 104 generally made of thermal-setting non-conductive plastic, such as Tecothane®. This header block assembly 104 houses one or more connector assemblies generally in accordance with ISO Standards IS-1, IS-2, or more modern standards, such as IS4 or DF4. These header block connector port assemblies are shown as 106 and 106'. Implantable leadwires 110, 110' have proximal plugs 108, 108' and are designed to insert into and mate with these header block connector cavities 106 and 106', or, in devices that do not have header block assemblies built directly into the pulse generator itself.

As used herein, the term "lead" refers to an implantable lead containing a lead body and one or more internal lead conductors. A "lead conductor" refers to the conductor that is inside of an implanted lead body. The term "leadwire" or "lead wire" refers to wiring that is either inside of the active implantable medical device (AIMD) housing or inside of the AIMD header block assembly or both. Furthermore, as used herein, in general, the terms lead, leadwire and pin are all used interchangeably. Importantly, they are all electrical conductors. This is why, in the broad sense of the term, lead, leadwire or pin can all be used interchangeably since they are all conductors. The term "conductive pathway" can also be used to be synonymous with lead conductor, lead, leadwire or pin or even a circuit trace. As described herein, composite conductive sintered paste filled vias passing through an insulator in nonconductive relation with a ferrule electrically acts the same as leadwire, lead wire, or pin. These sintered paste filled vias may also incorporate co-fired solid leadwires. As used herein, the term paste generally refers to pastes, inks, gels, paints, cermets, and other such metal and/or metal/ceramic sinterable material combinations that can be flowable, injectable, pressed, pulled, pushed or otherwise movable into an orifice or via. Post-sintering, the solvents and binders are baked out and, after sintering, the paste becomes a densified solid with monolithic structure. Additionally, AIMD, as defined herein, includes electronic circuits disposed within the human body that have a primary or secondary battery, or have an alternative energy source, such as energy induced by motion, thermal or chemical effects or through external induction. As used herein, the term "header block" is the biocompatible material that attaches between the AIMD housing and the lead. The term "header block connector assembly" refers to the header block including the connector ports for the leads and the wiring connecting the lead connector ports to the hermetic terminal subassemblies which allow electrical connections to hermetically pass inside the device housing. It is also understood by those skilled in the art that the present invention can be applicable to active implantable medical devices that do not have a header block or header block connector assemblies such as pulse generators.

FIG. 3 illustrates a prior art unipolar feedthrough capacitor 132. A quad polar feedthrough capacitor 132 was previously illustrated in prior art FIG. 2. Referring to FIG. 3, one can see that there's an external metallization 142 and a passageway or feedthrough hole metallization 144. This metallization can be applied by electroplating or by applying a fritted glass, which is then fired. In one embodiment, the fritted glass may comprise a silver or palladium silver glass matrix. In any event, after application of the metallization layers 142 and 144, one can make electrical contact to the feedthrough capacitor either by soldering or thermal-setting conductive adhesives or the like. As shown, the feedthrough capacitor comprises active electrode plates 148 and ground electrode plates 146. The reason the electrode plates 146 are called ground electrode plates and as will be further explained herein, is because the perimeter or outside diameter metallization 142 is configured to be attached to a ferrule and in turn, to the conductive housing of an AIMD, which forms an equipotential surface for energy dissipation (aka ground). Referring once again to FIG. 2, one can see that the housing 116, for an active implantable medical device, is generally metallic (titanium). One can also see that the feedthrough capacitor 132 is attached to a hermetically sealed subassembly 120 of the AIMD, which acts as a equipotential surface (ground).

FIG. 3A is taken generally from section 3A-3A from FIG. 3. Shown in exploded view, are ceramic cover sheets 147, active electrodes 148 that are disposed on ceramic layers 149 and ground electrode plates 146 that are disposed on ceramic layers 149. These are stacked up with cover sheets on the opposite end 147 and then pressed and laminated. It will be appreciated that blank cover sheets 147 can be disposed between the active layers 148 and the ground layers 146 thereby, increasing the dielectric thickness and increasing the voltage rating of the device. The electrode layers 148 and 146 are typically applied by silk-screening or equivalent waterfall processes.

FIG. 4 is a cross-sectional view showing the unipolar capacitor 132 of FIG. 3 mounted to a ferrule 112 of a hermetic seal subassembly 120 for an AIMD. As can be seen, the ground metallization 142 of the feedthrough capacitor 132 is electrically connected 152 to the ferrule 112 of the hermetic seal. The hermetic seal is accomplished generally by gold brazing between an alumina insulator 160. There is an outside diameter gold braze 150 between the insulator and the ferrule 112. There is also a gold braze 162 between leadwires 114, 111 and the inside diameter of an insulator 160 passageway 134 as illustrated. In order for gold braze material 150, 162 to wet to the insulator surfaces 160, there must first be an adhesion layer 153 and then a wetting layer 151, as illustrated. In one embodiment, the adhesion layer can be a sputtered layer of titanium, followed by a sputtered layer of molybdenum or niobium (the wetting layer). In some manufacturing agent operations, the adhesion and wetting layers can be combined into a single layer. Throughout the present invention, sometimes in order to simplify, the adhesion layer 153 and wetting layer 151 are not shown or at least not described. But it will be understood that anywhere that a gold braze is described herein to an insulator 160, that an adhesion/wetting layer is required.

As defined herein, what is referred to as the insulator is generally disposed between or inside a ferrule opening and has either lead conductors or conductive passageways or vias that pass through the hermetic terminal subassembly 120. The ceramic capacitor 130 also uses insulative materials, which are dielectrics. As previously described in FIG. 3A, these dielectric sheets 147,149 are referred to as dielectrics although it is appreciated that they are also insulative. In summary, as used herein, insulators are the insulators that are gold brazed to a ferrule of the AIMD, whereas capacitor dielectric insulators are referred to as dielectric layers.

Referring once again to FIG. 4, one can see that the ferrule 112 of the hermetic seal has been laser welded 154 into the overall housing 116 of the AIMD. This is very important in that the feedthrough capacitor ground metallization 142 becomes part of the overall electromagnetic shield of the AIMD housing. This forms in the industry what is known as a Faraday cage and provides an effective electromagnetic interference shield and energy dissipating surface. Referring back to FIG. 4, lead 114 on the body fluid side is generally connected to implanted leadwires and electrodes (not shown). Referring back to FIG. 2 for a prior art pacemaker, one can see these leadwires 107 and 107' that are connected to electrodes 109 that are located within the human heart. Again, referring to FIG. 2, undesirably, electromagnetic interference (EMI) can be coupled to these implanted leads and in turn, to the interior of the AIMD housing. It has been shown in numerous articles that EMI can disrupt the proper operation of the AIMD, such as a cardiac pacemaker and lead to improper therapy or even complete inhibition of therapy. Inhibition of therapy, for a cardiac pacemaker, can be immediately life-threatening to a pacemaker dependent patient.

Referring once again to FIG. 4, electromagnetic interference signals therefore, may be conducted along leadwire 114 to terminal 1 of the feedthrough capacitor. It is the purpose of the feedthrough capacitor 132 to divert unwanted high-frequency EMI signals from the leadwire 114, 111 so that by the time the signals reach terminal 2 (the AIMD electronics or device side), that the electromagnetic interference has been greatly attenuated or diverted through the feedthrough capacitor, harmlessly to the AIMD housing 116. This is further appreciated by looking at the schematic diagram of FIG. 4A. Electromagnetic interference signals enter terminal 1 of the 3-terminal feedthrough capacitor and are diverted harmlessly to the ground terminal 3 (116) before they can reach the device side 111, terminal 2.

The feedthrough capacitors 132, when properly installed, acts electrically as a continuous part of the titanium shield 116, which houses the active implantable medical device (AIMD). The feedthrough capacitor is a 3-terminal coaxial device whose internal electrode plates "plug the hole" and both reflect and absorb EMI fields. The feedthrough capacitor is novel in that, it is a broadband low pass filter, which allows desirable frequencies (like pacing pulses) to pass. Because it is a unique 3-terminal coaxial device, it provides effective attenuation to undesired signals (EMI) over a very broad band (10 MHz to 10 GHz frequency range). When designed and installed properly, feedthrough capacitors are very low inductance devices, which do not series resonate. It is very important that feedthrough capacitors be installed in such a way that undesirable resistances, for example, due to titanium oxides, cannot occur in the ground connection.

FIG. 5 is very similar to the schematic of FIG. 4A, except in this case, there is an oxide $R_{oxide}$, as illustrated. This oxide comes from undesirable oxidation of the ferrule 112 previously illustrated in FIG. 4. The electrical connection material 152 illustrated in FIG. 4, is connected to a titanium surface of the ferrule 112. As will be explained, titanium can undesirably form oxides, which become resistive and reduce the effectivity of the feedthrough capacitor 132.

FIG. 6A is taken from FIG. 21 of U.S. Pat. No. 5,333,095, the contents of which are incorporated herein fully by reference. Referring once again to FIG. 6A, one can see that there is a feedthrough capacitor 132 that is mounted onto a ferrule 112 of a hermetic seal subassembly 120. In this case, the diameter of the bipolar feedthrough capacitor (in this case, two passageways instead of one) greatly overhangs the ferrule 112. In this assembly, the steps are first, that the ferrule 112 (without the presence of the feedthrough capacitor 132) is first captured by two AIMD can halves 116, 116'. These are captured as a sandwich and then laser weld is performed between the ferrule 112 and the can halves 116, 116'. The feedthrough capacitor 132 has been subsequently added and an electrical connection has been formed between the feedthrough capacitor ground metallization 142 and to the exposed areas of the AIMD housing 116, 116'. In other words, in this case, there is no direct electrical connection between the feedthrough capacitor ground metallization 142 and the ferrule 112. However, as previously described in FIG. 5, FIG. 6B illustrates the schematic of the bipolar feedthrough capacitor of FIG. 6A. Again, undesirably, an oxide $R_{oxide}$ appears between the bipolar feedthrough capacitor and ground. As will be explained, this can seriously degrade filter performance.

FIG. 7A illustrates a quad polar feedthrough capacitor (meaning four passageways). It will be appreciated that any number of feedthrough holes 134, 144 can be produced. As previously described for the unipolar capacitor of FIG. 3, the quad polar capacitor of FIG. 4, has a ground metallization 142 and four passageways, each having their own active metallization 144. As used herein, the term active means an electrically active lead or passageway as opposed to a grounded connection. Active passageways may conduct therapeutic pacing pulses, biological sensing signals or even high-voltage therapeutic shocks. For a neurostimulator application, active passageways may include AC, pulse, triangular or many other different types of waveforms; for example, for a spinal cord stimulator to create paresthesia.

FIG. 7B is taken generally from FIG. 7B-7B from FIG. 7A, which illustrates the quad polar feedthrough capacitor in cross-section. One can see that there are ground electrode plates 146, which are disposed through the feedthrough capacitor structure and connected to the ground metallization 142. One can also appreciate that each of the feedthrough holes 134 has its own set of active electrodes 148 that are disposed and overlapping or sandwich-type construction between the ground electrode plates 146. It is the overlapping of the active and ground electrode plates in the dielectric that create the individual feedthrough capacitors. Each of the four feedthrough capacitors are associated with its own passageway metallization 144.

FIG. 8 is an exploded view of the unipolar capacitor previously illustrated in FIGS. 7A and 7B. As for the unipolar capacitor of FIG. 3A, there are cover sheets 147 and then an active layer showing four active electrodes 148 that are each individually associated with one of the four passageways. As one can see, the ground electrode layer 146 extends in non-conductive relationship with the active passageways to the feedthrough capacitors outside diameter. As before, these are stacked up in interleave relationship to form a quad polar feedthrough capacitor.

FIG. 9 is the schematic drawing of the feedthrough capacitor of FIG. 8, but in this case, this is after the feedthrough capacitor has been installed to a hermetic seal ferrule and insulator with pins, as previously described in FIGS. 2, 4 and 6A. It is assumed that the feedthrough capacitor outside diameter metallization 142 has been connected directly to either the titanium ferrule 112 or the AIMD housing 116. In both cases, the ferrule and/or the housing would be of titanium and would be subject to oxidation. Accordingly, in the schematic drawing of FIG. 9, one can see that there is an undesirable $R_{oxide}$ shown between each of the feedthrough capacitors 132 and ground 116 (AIMD housing). Referring once again to FIG. 9, one can see that each of the feedthrough capacitors 132 is labeled with terminals 1, 2 and 3. At DC or direct current, there is no difference between terminals 1 and 2 as that is a solid through-pin or leadwire or passageway. However, at RF frequencies, the feedthrough capacitor 132 substantially attenuates frequencies coming from the body fluid side from terminal 1 into the inside of the AIMD housing or device side to terminal 2. As previously stated, these undesirable EMI signals that are entering at terminal 1, are diverted by capacitive reactance through the feedthrough capacitor to ground terminal 3.

FIG. 10A is taken from FIG. 1 of U.S. Pat. No. 5,867,361 also known as the Wolf Patent, the contents of which are incorporated herein fully be reference. Referring to FIG. 10A, one can see that Wolf has a feedthrough capacitor 132 that is connected to a ferrule structure 112. This electrical connection between the ferrule and the capacitor is accomplished by an electrically conductive adhesive 125 as indicated. Then, electrically conductive adhesive 123 connects the capacitor to the device side wire bond pad 121. Wolf contemplates a gold braze area 131, which is the small triangular shape shown in cross-section. Wolf teaches away from a solid through-pin throughout his patent. As one can see, Wolf has a pin 133 disposed on the body fluid side. This pin 133 is discontinuous and is attached by gold braze 127 to insulator structure 160. The insulator is hermetically sealed and mechanically attached to the ferrule by another gold braze 129. In other words, there are three gold brazes described by the Wolf invention. On the device side, there is a wire bond pad 121, which is taught to be discontinuous from lead segment 133. A major deficiency of the Wolf invention is that, the triangle or gold braze area 131 cannot possibly stay in place during the high-temperature gold brazing operation, which typically occurs in a gold braze furnace. It is well known to those skilled in the art that the feedthrough capacitor 132 cannot be present during such high-temperature brazing operations. Not only would the capacitor structure itself be harmed, but its terminations 142 and 144 (not shown in Wolf but described) would be significantly damaged during such high-temperature gold braze operation.

Accordingly, FIG. 10B illustrates the gold brazing operation before the feedthrough capacitor 132 of Wolf is added. As one can see, there is a gold braze preform 131 which is placed (and would generally be a round or O-ring type of cross-section prior to high-temperature application). There are also other gold braze preforms 127 and 129. These are idealistic shapes or even fanciful shapes. As illustrated in FIG. 10C, at high-temperature, once these three gold brazes become molten, they will not stay in place because there is nothing to retain them. In other words, when liquid, gravitational forces will pull 131 generally down into the area as illustrated in FIG. 10C and away from the electrical attachment area 125. A thin layer of gold braze 131 would be left behind, but those skilled in the art realize that thin layers of gold do not provide a significant barrier against oxides. It is commonly known, for example, in the plating of various types of leadwires that first a nickel barrier is laid down and then a final gold layer is laid down. The nickel layer is a barrier layer, such that oxides will not penetrate through it and then the thin layer of gold on top of the nickel provides an oxide-resistant wetting layer for solders and the like.

Referring back to FIG. 10C, one will also see that gold braze 127 cannot possibly retain the shape as shown in FIG. 10A or 10B. Again, once it becomes liquid, due to gravitational forces, it will slump down as indicated in FIG. 10C. In summary, the major deficiency of the Wolf invention to prevent the undesirable oxides $R_{oxide}$, as illustrated in FIG. 6B and FIG. 9, is that Wolf's gold braze GB3 is never retained and therefore, cannot form a reliable low resistance connection between the feedthrough capacitor 132 ground metallization and the ferrule 112.

FIG. 11 illustrates a prior art rectangular feedthrough capacitor 132, which has the same number of poles (4, quadpolar) as previously illustrated in FIG. 7A. This illustrates that feedthrough capacitors can be round (sometimes called discoidal), rectangular or even any other shape. As previously mentioned, the feedthrough capacitor can be quad polar, as illustrated, or any other number of feedthrough holes 144. Referring once again to FIG. 11, the ground metallization 142 is shown being brought out to both of the long sides of the feedthrough capacitor 132. This is best understood by referring to FIG. 14, which is taken generally from section 14-14 from FIG. 11. This illustrates the ground electrode plates and the fact that they are only exposed along the capacitor's long sides where metallization 142 can be applied. Also shown as FIG. 13, which is taken generally from section 13-13 from FIG. 11, illustrating four active electrodes 148. Each of these active electrodes is associated with one of the active terminal pins 111, 114. The feedthrough capacitor, as illustrated in FIG. 11, is shown ready for installation on top of a hermetic seal subassembly 120 that's illustrated in FIG. 12. Referring to FIG. 12, one can see that there is a metallic ferrule, which is typically of titanium, an insulator, which is typically of alumina and four pins or leadwires 111, 114. A hermetic and mechanical seal is effective between each of the pins 111, 114 and the insulator 160 by gold brazes 162. Also, the rectangular perimeter of the alumina insulator 160 is shown gold brazed 150 to the ferrule 112.

FIG. 15 illustrates the feedthrough capacitor 111 installed to the hermetic seal assembly 120, as previously described in FIGS. 11 and 12. As can be seen, there is an electrical connection material 152, which connects from the capacitor's ground metallization 142 directly to the ferrule 112.

FIG. 16 is taken generally from section 16-16 from FIG. 15. In this section, one can see that there is a gold braze 150 that forms a mechanical and hermetic seal between the insulator 160 and ferrule 112. There is also a hermetic seal gold braze 162 between the insulator 160 and leadwire 111, 114. In this case, the feedthrough capacitor 132 is generally larger in diameter than the gold braze hermetic seal area 150. In this case, one can see the electrical attachment material 152 connecting between the capacitor 132 ground metallization 142 into the ferrule. Layer 164 illustrates a highly undesirable oxide layer on the titanium surface of ferrule 112. Oxide layer 164 would appear all over the surfaces of the titanium ferrule 112 but is shown disposed only between the electrical attachment material 152 and the ferrule for simplicity. Referring once again to FIGS. 15 and 16, one can see that the ferrule 112 has an h-flange type shape 163. This is for capturing and subsequent laser welding of AIMD housing halves 116.

FIGS. 11 through 20 herein were all taken from FIGS. 11 through 20 of U.S. Pat. No. 9,427,596, the contents of which are incorporated herein fully by reference. The '596 patent includes a detailed technical description of the capacitor's equivalent series resistance, the importance of parasitic resistance (ohmic loss) and the problem with oxides of titanium.

FIG. 17 is a schematic diagram illustrating the undesirable presence of $R_{oxide}$ in the ground path of the quad polar feedthrough capacitor. This $R_{oxide}$ results from the oxide layer 164 previously described in FIG. 16.

FIG. 18 shows the use of novel gold braze bond pads 165 that are one embodiment of a novel feature of the '596 patent. This is best understood by referring to FIG. 19 showing that the feedthrough capacitor 132 ground metallization 142 is electrically attached 152 by a thermal-setting conductive adhesive or a solder or the like directly to this gold bond pad area 165. It is well known that gold is a very noble material and does not oxidize. When sufficiently thick, a layer of gold will effectively block titanium oxides from interfering with the high-frequency electrical connection material 152. This is best understood by referring to FIG. 20, which is taken from section 20-20 from FIG. 19. In the cross-section, one can see the electrical connection material 152 that effects a very low impedance and low resistant electrical connection between the feedthrough capacitor ground metallization 142 and the gold braze pad area 165. During gold brazing, the gold braze pad 165 forms a continuous part of the hermetic seal 150 that effects a mechanical and hermetic joint to the insulator 160. In other words, an essential feature of the '596 patent, is that the low impedance, low resistance ground attach area is continuous with and one of the same width, as the same hermetic seal 150 that forms the hermetic seal gold braze.

FIG. 20A is taken from section 20A-20A from FIG. 19. FIG. 20A shows a serious deficiency in the central design concept of the '596 patent. That is, the gold braze 165 is not contained in such a way that it cannot be affected by gravitational forces during high-temperature gold braze furnace operations. As previously mentioned, during high-temperature gold brazing operations, the gold becomes molten or even liquid and due to gravitational forces, can flow out of a defined pocket area as previously illustrated in pocket area 165 in FIG. 20. In other words, it has a tendency to run down, as shown as 165' in FIG. 28. Again, as with the deficiency in Wolf, this does leave behind a thin layer of gold, however, in order to overcome this, an excessive amount of gold must be used, and one must rely on reduced contact area for the electrical connection material 152', as illustrated. By carefully controlling the fit-up tolerances between the alumina insulator 160 and the inside diameter of the ferrule 112, one can minimize the gold braze gravitational rundown 165'. However, this makes for a more expensive process and the need to hold the individual pieces to very tight tolerances.

Referring once again to FIG. 20A, one can see that there is a thin layer of gold 165T that is left behind. The problem is that this uncontrolled thin layer may or may not be oxide-resistant. As previously described, when gold becomes too thin, oxides can penetrate right through the relatively porous gold surface. Referring once again to FIGS. 11 through 20 herein, there are also taken from FIGS. 14 through 22 of U.S. Pat. No. 6,765,779, the contents of which are also incorporated herein fully by reference. The '779 patent includes extensive detail on undesirable formation of titanium oxides and a capacitor's equivalent series resistance, including a description of both dielectric loss tangent and ohmic losses.

FIGS. 21 and 22 herein are taken from FIGS. 23 and 24 of the '779 patent. FIG. 21 illustrates that the electrical connection material 152 contacts between, in this case, a round quad polar capacitor's ground metallization 142 and the gold braze area of the hermetic seal 165. This is best understood by referring to section 22-22 from FIG. 21, which is illustrated in FIG. 22. Referring to FIG. 22, one can clearly see that the electrical connection material 152, which can be of thermal-setting conductive adhesive or a solder or the like, makes a low resistance/impedance (free of titanium oxides) connection between the capacitor ground metallization 142 and at least a substantial portion of the gold braze pad area 165, which also forms the hermetic seal between the ferrule 112 and insulator 160. This forms an oxide-resistant low impedance and low resistance electrical connection that would be robust at high-frequencies so that the feedthrough capacitor 132 can properly divert unwanted high-frequency EMI energy. As defined herein, an EMI filter hermetically sealed assembly for an active implantable medical device, will be herein designated as assembly 210. The '779 Patent has enjoyed great commercial success and has proven to be highly reliable. Manufacturing processes of the '779 Patent does require tight dimensional tolerances between the ferrule inside diameter and the alumina insulator outside diameter or perimeter. In addition, the oxide-resistant pads as described in the '779 Patent require a significant amount of extra gold to be used in the process which is thereby increasingly expensive.

FIG. 22A is taken from section 22A-22A from FIG. 21 and illustrates what happens to the gold braze 165 during high-temperature gold braze furnace reflow operations. Due to gravity, since there is nothing to physically constrain the gold, when molten or liquid, it has a tendency to flow down in the area 165', as illustrated. This leaves behind a much smaller area of gold 165T for electrical attachment 152' to the feedthrough capacitor ground metallization 142. Referring once again to FIGS. 22 and 22A, a step ST has been added in the ferrule in an attempt to slow down and prevent the flow of the gold braze material 165T. This is somewhat effective but requires that a great deal more gold 165 must be used before this column is filled up, such that a suitable electrical connection 162' can be accomplished between the feedthrough capacitor ground metallization 142 and the gold braze surface 165T.

FIG. 23 is an electrical schematic taken from FIGS. 20 through 22A wherein the $R_{oxide}$ is no longer present.

FIG. 24 illustrates filter performance otherwise known as attenuation or insertion loss curves vs frequency. An ideal feedthrough capacitor C,132 attenuation curve is shown. One can see that it has a slight self-resonance above 1 GHz and then continues to function. Accordingly, it becomes a broadband 3-terminal filter as previously described. As can be seen, the ideal feedthrough capacitor has over 30 dB of attenuation at all frequencies above 450 MHz. This frequency range is important because that's the range at which cell phones operate. Cell phones are of particular concern to active implantable medical devices because they are small and can be brought into very close proximity to a medical implant. For example, one concern is for a pacemaker patient where the cell phone may be placed in a shirt pocket directly over the implant. This would couple maximum energy to implanted leads. Referring once again to the insertion loss attenuation curves of FIG. 24, one can see what happens when the feedthrough capacitor has undesirable resistive oxide $R_{oxide}$ in its ground electrical path. The oxide degrades the attenuation or filter performance such that you end up with a curve, which provides less than 30 dB of attenuation at frequencies above 450 MHz. This seriously degraded filter performance is of great concern because if a closely held emitter, such as a cellular telephone, interferes with, for example, a pacemaker sense circuit, it can undesirably cause the pacemaker to inhibit. Inhibit means that it would fail to provide life-saving therapeutic pulses. One might ask, why are pacemakers designed to inhibit? Well, there are two reasons: Many patients who suffer from bradycardia (a very low heart rate) are not bradycardic all-day long. In other words, they can come in and out of bradycardic (life-threatening) condition. Therefore, demand pacemakers were developed such that when a patient's normal sinus rhythm returns, the pacemaker will inhibit. This is to not only save battery life, but also prevents a condition called rate competition. This is where you wouldn't want the pacemaker to provide a pulse that is out of sync or competitive with a patient's intrinsic rhythm. However, this does lead to electromagnetic interference danger. If EMI is undesirably detected as a normal cardiac pulse, it can cause the device to inhibit, which is immediately life-threatening for a pacemaker dependent patient.

Accordingly, there is a need to provide an oxide-resistant electrical connection between the filter capacitor ground termination and the hermetic seal ferrule that embodies the present invention, which is a gold pocket pad, and wherein, the gold pocket pad reliably forms a thick enough metallurgically bonded layer to form an oxide-resistant surface to which a filter capacitor ground electrical connection can be made. As carefully described, none of the prior art provides a defined pocket (swimming pool) to capture the gold pocket preform in such a way that it cannot undesirably flow during high-temperature operations such as during hermetic seal gold brazing.

SUMMARY OF THE INVENTION

An exemplary embodiment of the present invention is shown best in FIG. 30 where a feedthrough subassembly (210) is attachable to an active implantable medical device (100). The feedthrough subassembly comprises: (a) a metallic ferrule (112) configured to be installed in an opening (115) of a housing (116) of the active implantable medical device (100), the ferrule comprising: (i) a conductive ferrule body (112) separating a body fluid side opposite a device side; (ii) at least one surface (113) disposed on the device side; and (iii) a ferrule opening (121) passing through the at least one surface (113) and extending between and through to the body fluid side and the device side; (b) an insulator body (160) hermetically sealing the ferrule opening (121) of the ferrule (112) by a first gold braze (150), the insulator body (160) having at least one via hole (167) disposed through the insulator body (160) between the body fluid side and the device side; (c) at least one conductor (111, 114, 117, 185, 186, 186W) disposed through and hermetically sealed to the at least one via hole (167); (d) at least one pocket (248) formed in the at least one surface (113) of the ferrule (112) disposed on the device side; and (e) a gold pocket pad (250) disposed within the at least one pocket (248); (f) wherein the first gold braze (150) and the gold pocket pad (250) are not physically touching one another. Alternatively, the insulator body may hermetically seal the ferrule opening of the conductive ferrule body by at least one of a first gold braze ceramic seal, a glass seal or a glass-ceramic seal. Accordingly, the insulator body has at least one hermetically sealed conductive pathway disposed through the insulator body between the body fluid side and the device side, the conductive pathway being in non-conductive relationship with the conductive ferrule body.

As defined herein, the gold pocket pad embodies one or more pockets that are formed on the device side of the ferrule surface. These pockets are each loaded with a gold preform (or equivalently oxide-resistant material), and the preform is reflowed at a temperature above the gold melting point. The gold preform may be a substantially pure gold solid material, gold powder, an alloy of at least 50% gold, gold nano-particles, or coiled fine gold wire. The preform may also be of platinum, palladium and any alloys thereof. The preform may be any material that can be metallurgically bonded to titanium while, at the same time, burning through or penetrating any oxides of titanium that may be present, and ultimately result in a substantially oxide-resistant capacitor ground connection pad. Oxide-resistant is herein defined as the ability to resist surface reactions that increase connection electrical resistance, introduce unstable connection resistance change or disrupts electrical connection conductivity. As used throughout this specification we will refer to loaded pocket pads simply as gold pocket pads, but it will be understood that this term is inclusive of all of the above material loading options. The pocket is essential in that it creates a contained structure (like a swimming pool) such that the preform layer may be relatively thin (compared to any prior art) and will not undesirably flow away, outflow, seep or bleed to other areas or surfaces. In one embodiment the thickness of the gold pocket preform may be a minimum of 1 mil thick (0.001 inches). In a different embodiment (to facilitate preform handling including robotic placement into the pockets) preforms may be on the order of 5 to 10 mils minimum thickness.

In other exemplary embodiments, the feedthrough subassembly may include a filter capacitor disposed on the device side, the filter capacitor comprising at least one of a feedthrough filter capacitor, a chip capacitor, an MLCC, an X2Y attenuator, an internally grounded feedthrough capacitor, a hybrid internally grounded feedthrough capacitor or a chip capacitor. When the chip capacitor, the MLCC or the X2Y attenuator is mounted on a circuit board the circuit board may be disposed adjacent to the ferrule and/or the insulator body.

In other exemplary embodiments, the feedthrough subassembly may include a feedthrough filter capacitor (132) disposed on the device side, the feedthrough filter capacitor (132) comprising: i) at least one active electrode plate (148) disposed parallel and spaced from at least one ground electrode plate (146), wherein the plates (148,146) are disposed within a capacitor dielectric substrate (147,149); ii) a first passageway (134) disposed through the capacitor dielectric substrate (147,149) and disposed perpendicular to the plates (148,146); iii) a capacitor active (internal) metallization (144) disposed within the first passageway (134) electrically connected to the at least one active electrode plate (148) and in non-conductive relation with the at least one ground electrode plate (146); iv) a capacitor ground (external) metallization (142) disposed on an outside surface of the capacitor dielectric substrate (147,149) and electrically connected to the at least one ground electrode plate (146) and in non-conductive relation with the at least one active electrode plate (148); v) wherein the at least one conductor (111, 114, 117, 185, 186, 186W) is electrically connected to the capacitor active metallization (144); and including an electrical connection material (152) electrically connecting the capacitor ground metallization (142) to the gold pocket pad (250) disposed within the at least one pocket (248).

The first gold braze (150) and gold pocket pad (250) may be formed at the same time in a gold braze reflow operation or the first gold braze (150) and gold pocket pad (250) may be formed at different times. The first gold braze (150) and gold pocket pad (250) may comprise the same overall metallic composition or may comprise different overall metallic compositions.

The electrical connection material (152) may comprise a thermal-setting conductive adhesive or a solder.

The insulator body (160) may comprise alumina ceramic. The alumina insulator body (160) may be at least partially disposed within the ferrule opening (121). The metallic ferrule (112) may comprise titanium.

The gold pocket pad (250) disposed within the at least one pocket (248) may not include a second material (metal addition) disposed at least partially over the gold pocket pad, wherein the second material is a different metallic material in comparison to the gold pocket pad.

An overhanging capacitor is best seen in FIGS. 31 and 37 wherein a first capacitor perimeter surface (252) of the capacitor extends beyond a first ferrule perimeter surface (256) of the ferrule, and wherein a second capacitor perimeter surface (254) of the capacitor does not extend beyond a second ferrule perimeter surface (258) of the ferrule. The capacitor ground metallization (142) may be disposed at least on the second capacitor perimeter surface of the capacitor (254). The at least one pocket 248 may be located adjacent to the second ferrule perimeter surface (254). The first capacitor perimeter surface (254), the second capacitor perimeter surface (254), the first ferrule perimeter surface (258) and the second ferrule perimeter surface (258) may be perpendicular to the at least one surface (113) of the metallic ferrule (112). The first capacitor perimeter surface (252) may be perpendicular to the second capacitor perimeter surface (254) and wherein the first ferrule perimeter surface (256) may be perpendicular to the second ferrule perimeter surface (258).

Referring to the left hand side of FIG. 30, the at least one conductor comprises: i) a first conductive leadwire (114) having a first conductive leadwire first end (114') at least partially disposed within the at least one via hole (167) and having a first conductive leadwire second end (114") disposed past the insulator body (160) on the body fluid side; ii) a second conductive leadwire (117) having a second conductive leadwire first end (117') at least partially disposed within the at least one via hole (167) and having a second conductive leadwire second end (117") disposed past the insulator body (160) on the device side and at least partially disposed within the first passageway (134) of the feedthrough filter capacitor (132); iii) wherein the first conductive leadwire first end (114') is disposed near, at or adjacent to the second conductive leadwire first end (117');

iv) and wherein the first conductive leadwire (114) is not the same material as the second conductive leadwire (117).

A second gold braze (162) may electrically connect the first conductive leadwire (114) to the second conductive leadwire (117).

The at least one conductor may further comprise: i) a third conductive leadwire (111) having a third conductive leadwire first end (111') at least partially disposed within the first passageway (134) of the feedthrough filter capacitor (132); ii) wherein the third conductive leadwire first end (111') is disposed near, at or adjacent to the second conductive leadwire second end (117'); iii) wherein a third conductive leadwire second end (111") is disposed past the filter feedthrough capacitor (132) on the device side; iv) and wherein the third conductive leadwire (111) is not the same material as the first conductive leadwire (114) or the second conductive leadwire (117).

A second electrical connection material (156) may electrically connect the second conductive leadwire (117) to the third conductive leadwire (111).

Referring to the right hand side of FIG. 30, the at least one conductor may comprise: i) a first conductive leadwire (114) disposed through the at least one via hole (167) and having a first conductive leadwire first end (114') disposed past the insulator body (160) on the device side and at least partially disposed within the first passageway (134) of the feedthrough filter capacitor (132) and having a first conductive leadwire second end (114") disposed past the insulator body (160) on the body fluid side; ii) a second conductive leadwire (111) having a second conductive leadwire first end (111') at least partially disposed within the first passageway (134) of the feedthrough filter capacitor (132) and having a second conductive leadwire second end (111") disposed past the feedthrough filter capacitor (132) on the device side; iii) wherein the first conductive leadwire first end (114') is disposed near, at or adjacent to the second conductive leadwire first end (111'); iv) and wherein the first conductive leadwire (114) is not the same material as the second conductive leadwire (111).

A second electrical connection material (156) may electrically connect the first conductive leadwire to the second conductive leadwire.

Referring to the right hand side of FIG. 29A, the feedthrough subassembly has at least one conductive pathway which comprises: i) a first conductive leadwire (114) having a first conductive leadwire first end at least partially disposed within the insulator body and having a first conductive leadwire second end disposed past the insulator body on the body fluid side; and ii) a second conductive leadwire (111) having a second conductive leadwire first end at least partially disposed within the insulator body and having a second conductive leadwire second end disposed past the insulator body and through the first passageway of the feedthrough filter capacitor. As can be seen in FIG. 29A, the first conductive leadwire first end is disposed at or adjacent to the second conductive leadwire first end. Also, the first conductive leadwire is not the same material as the second conductive leadwire. However, the leadwires (114) and (111) can be welded (145) before insertion to ease manufacture and insure a reliable connection. Furthermore, the braze material (162) also captures and electrically connects the leadwires (114) and (111) while also providing the hermetic seal.

Referring to FIGS. 41 and 47, the at least one conductor may comprise a composite fill (185,186) disposed within the at least one via hole (167) extending from a first composite fill end (189') to a second composite fill end (189"), wherein the first composite fill end (189') may be disposed at or near the device side of the insulator body (160), and wherein the second composite fill end (189") is disposed at or near the body fluid side of the insulator body (160).

The composite fill may comprise: i) a ceramic reinforced metal composite (185) comprising alumina and platinum; and ii) a substantially pure platinum fill (186); iii) wherein the alumina insulator body (160) and the composite fill (185,186) are co-fired.

The composite fill may comprise: i) a ceramic reinforced metal composite (185) comprising alumina and platinum; and ii) a metallic wire (186W); iii) wherein the alumina insulator body (160) and the composite fill (185,186W) are co-fired.

Referring to FIG. 41, the ferrule (112) may include a peninsula (139) extending within the ferrule opening (121), wherein the at least one pocket (248) is formed in the at least one surface (113) of the ferrule peninsula (139).

An internally grounded feedthrough filter capacitor (132') may be disposed on the device side, the internally grounded feedthrough filter capacitor (132') comprising: i) at least one active electrode plate (148) disposed parallel and spaced from at least one ground electrode plate (146), wherein the plates are disposed within a capacitor dielectric substrate (147,149); ii) a first passageway (134) disposed through the capacitor dielectric substrate (147,149) perpendicular to the plates; iii) a (first) capacitor active conductor (119') disposed within the first passageway (134) electrically connected to the at least one active electrode plate (148) and in non-conductive relation with the at least one ground electrode plate (146); iv) a second passageway (134) disposed through the capacitor dielectric substrate (147,149) perpendicular to the plates; v) a (second) capacitor ground conductor (119") disposed within the second passageway (134) electrically connected to the at least one ground electrode plate (146) and in non-conductive relation with the at least one active electrode plate (148); vi) including an electrical connection material (202) electrically connecting the (second) capacitor ground conductor (119") to the gold pocket pad (250) disposed within the at least one pocket (248).

The internally grounded feedthrough filter capacitor (132') may not have an external metallization disposed on an outside surface of the capacitor dielectric substrate (147, 149).

Referring to FIGS. 36 and 38 the ferrule may include a bridge (141) extending across the ferrule opening (121), wherein the at least one pocket (248) is formed in the at least one surface (113) of the ferrule bridge (141).

An internally grounded feedthrough filter capacitor (132') may be disposed on the device side, the internally grounded feedthrough filter capacitor (132') comprising: i) at least one active electrode plate (148) disposed parallel and spaced from at least one ground electrode plate (146), wherein the plates are disposed within a capacitor dielectric substrate (147,149); ii) a first passageway (134) disposed through the capacitor dielectric substrate (147,149) perpendicular to the plates; iii) a (first) capacitor active conductor (119') disposed within the first passageway (134) electrically connected to the at least one active electrode plate (148) and in non-conductive relation with the at least one ground electrode plate (146); iv) a second passageway (134) disposed through the capacitor dielectric substrate (147,149) perpendicular to the plates; v) a (second) capacitor ground conductor (119") disposed within the second passageway (134) electrically connected to the at least one ground electrode plate (146) and in non-conductive relation with the at least one active electrode plate (148); vi) including an electrical connection material (202) electrically connecting the (second) capacitor ground conductor (119") to the gold pocket pad (250) disposed within the at least one pocket (248).

The internally grounded feedthrough filter capacitor (132') may not have an external metallization disposed on an outside surface of the capacitor dielectric substrate (147, 149).

Referring to FIG. 36 the feedthrough subassembly may include a second pocket formed in the at least one surface of the ferrule and a second gold pocket pad disposed within the second pocket. The first pocket pad and the second pocket pad may be disposed at opposite ends of the ferrule. A hybrid internally grounded feedthrough filter capacitor is then disposed on the device side, the hybrid internally grounded feedthrough filter capacitor comprising: i) at least one active electrode plate disposed parallel and spaced from at least one ground electrode plate, wherein the plates are disposed within a capacitor dielectric substrate; ii) a first passageway disposed through the capacitor dielectric substrate perpendicular to the plates; iii) a capacitor active conductor disposed within the first passageway electrically connected to the at least one active electrode plate and in non-conductive relation with the at least one ground electrode plate; iv) a second passageway disposed through the capacitor dielectric substrate perpendicular to the plates; v) a capacitor ground conductor disposed within the second passageway electrically connected to the at least one ground electrode plate and in non-conductive relation with the at least one active electrode plate, wherein the capacitor ground conductor is electrically connected to the ferrule; vi) a first ground metallization disposed on at least a portion of a first outside surface of the capacitor dielectric substrate and electrically connected to the at least one ground electrode plate; vii) a second ground metallization disposed on at least a portion of a second outside surface of the capacitor dielectric substrate and electrically connected to the at least one ground electrode plate. A first electrical connection material electrically connects the gold pocket pad to the first ground metallization. A second electrical connection material electrically connects the second gold pocket pad to the second ground metallization. As seen in FIG. 36, a very low inductance is achieved because the grounding path can go through the center grounding pin 111gnd or can go to either end of the capacitor through to the gold pocket pads 250.

Referring to FIGS. 42-46, a chip capacitor (194) may be disposed on the device side, the chip capacitor comprising: i) at least one active electrode plate (148) disposed parallel and spaced from at least one ground electrode plate (146), wherein the plates are disposed within a capacitor dielectric substrate (147,149); ii) a first capacitor metallization (144) disposed on one end of the chip capacitor (194) and electrically connected to the at least one active electrode plate (148) and in non-conductive relation with the at least one ground electrode plate (146); iii) a second capacitor metallization (142) disposed on another end of the chip capacitor (194) and electrically connected to the at least one ground electrode plate (146) and in non-conductive relation with the at least one active electrode plate (148).

A first electrical connection material (156) may electrically couple the first capacitor metallization (144) to the conductor (111,114). A second electrical connection material (152) may electrically couple the second capacitor metallization (142) to the gold pocket pad (250) disposed in the at least one pocket (248) of the ferrule (112).

The chip capacitor (194) may be attached to the insulator body (160). The chip capacitor (194) may be attached to a circuit board (155), wherein the circuit board (155) is attached to the insulator body (160).

The circuit board (155) may comprise an electrically conductive ground plate (161), wherein the first capacitor metallization (144) is in electrical communication with the conductor (111,114). Furthermore, the ground plate (161) may be in electrical communication with the second capacitor metallization (142) and the gold pocket pad (250) which is disposed in the at least one pocket (248) of the ferrule (112).

An anisotropic conductive film (ACF, 212') may be disposed between the circuit board (155) and the insulator (160). Furthermore, the circuit board (155) may include at least one electrically conductive proud feature (260) extending at least a portion beyond the circuit board. The electrically conductive proud feature is disposed over the gold pocket pad (250) and is in electrical communication with the gold pocket pad (250) by the anisotropic conductive film (212') and in electrical communication with the second capacitor metallization (142) of the chip capacitor (194). The first capacitor metallization (144) of the chip capacitor (194) may be in electrical communication with the conductor (111,114).

In other exemplary embodiments, an adhesion layer (153) may be attached to the insulator body (160) and a wetting layer (151) may be attached to the adhesion layer. The first gold braze (150) is then physically disposed between the wetting layer (151) and the metallic ferrule (112). The adhesion layer (153) may comprise titanium and the wetting layer (151) may comprise molybdenum or niobium. Furthermore, the adhesion (153) and wetting layer (151) may be formed as one layer.

BRIEF DESCRIPTION OF THE DRAWINGS

The accompanying drawings illustrate the invention. In such drawings:

FIG. 10A is taken from FIG. 1 of U.S. Pat. No. 5,867,361 also known as the Wolf Patent;

FIG. 10B illustrates the gold brazing operation before the feedthrough capacitor of Wolf is added;

FIG. 10C is taken from section 10C-10C of FIG. 10B and illustrates at high-temperature the three gold brazes becoming molten and moving as they will not stay in place because there is nothing to retain them;

FIG. 11 illustrates a prior art rectangular feedthrough capacitor, which has the same number of poles (4, quadpolar) as previously illustrated in FIG. 7A;

FIG. 12 illustrates the hermetic seal subassembly ready to receive the capacitor of FIG. 11;

FIG. 13 is taken generally from section 13-13 from FIG. 11 showing the active electrode plates;

FIG. 14 is taken generally from section 14-14 from FIG. 11 showing the ground electrode plate;

FIG. 32A illustrates an internally grounded feedthrough capacitor exploded away and ready for installation on internally grounded hermetic seal assembly.

FIG. 32B is similar to FIG. 32A showing the electrode plate structure of the capacitor;

FIG. 32C is similar to FIG. 32A now showing the capacitor mounted;

FIG. 50 is similar to FIG. 49 now showing the use of proud features for use with an anisotropic conductive film; and FIG. 50A is an enlarged sectional view taken along lines 50A-50A from FIG. 50.

DETAILED DESCRIPTION OF THE PREFERRED EMBODIMENTS

Figure 25:
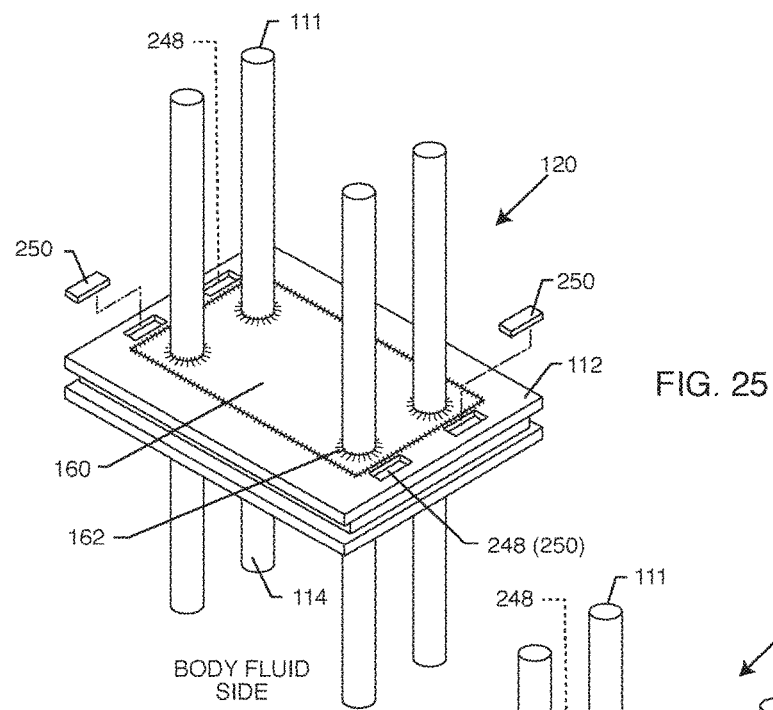
FIG. 25 is similar to FIG. 48 of U.S. Pat. No. 9,427,596 but now shows only a gold braze disposed with the ferrule pocket.
Figure 26:
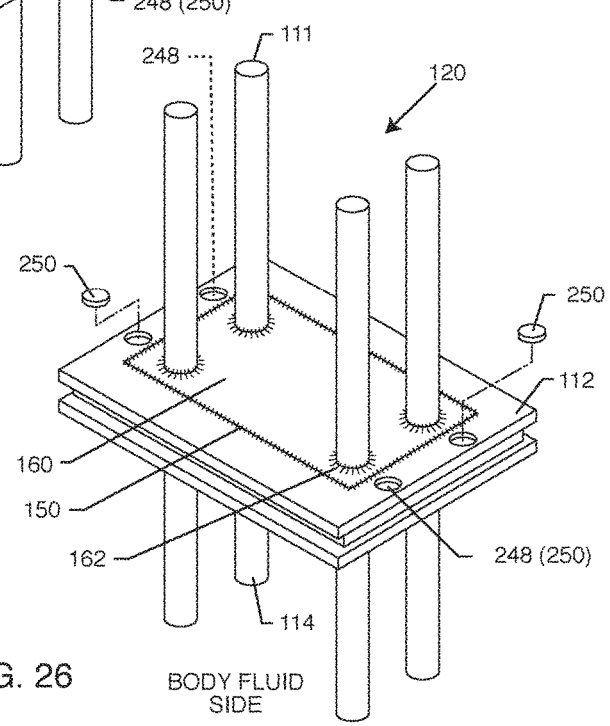
FIG. 26 is similar to FIG. 49 of U.S. Pat. No. 9,427,596 but now shows only a gold braze disposed with the ferrule pocket.
Figure 27:
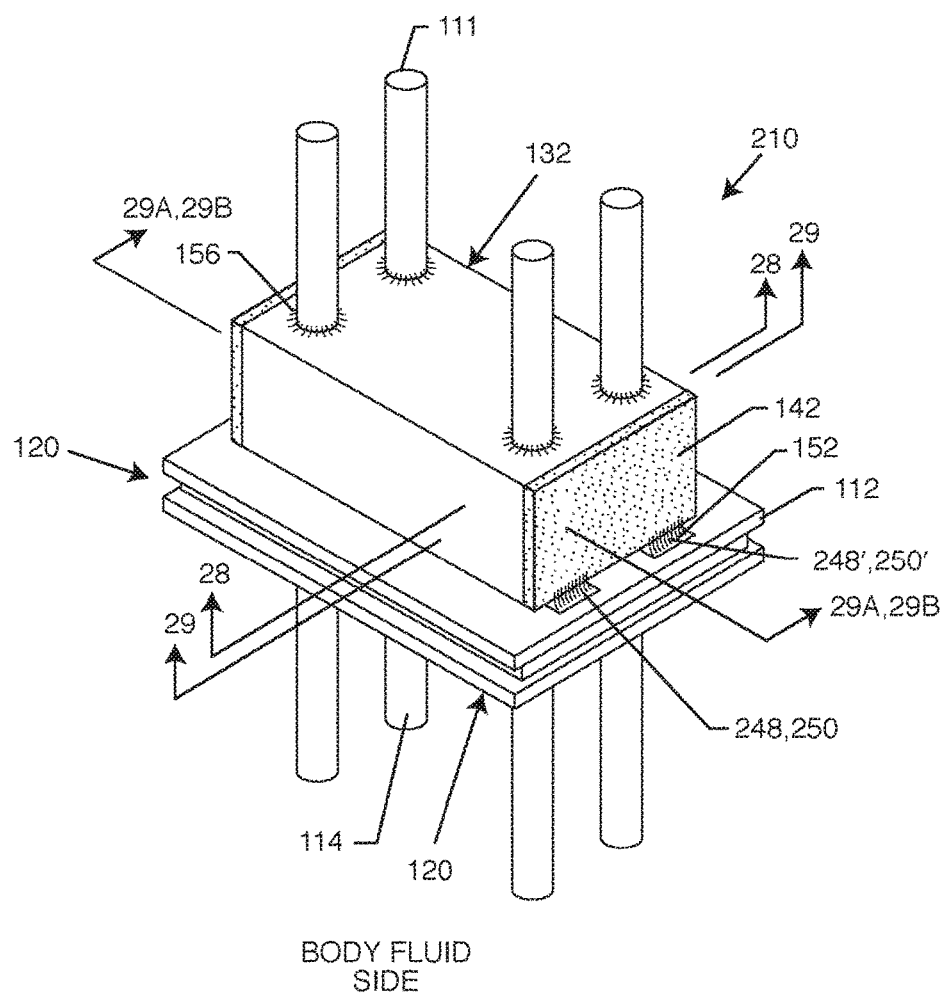
FIG. 27 is similar to FIG. 50 of U.S. Pat. No. 9,427,596 but now shows only a gold braze disposed with the ferrule pocket.
Figure 48:
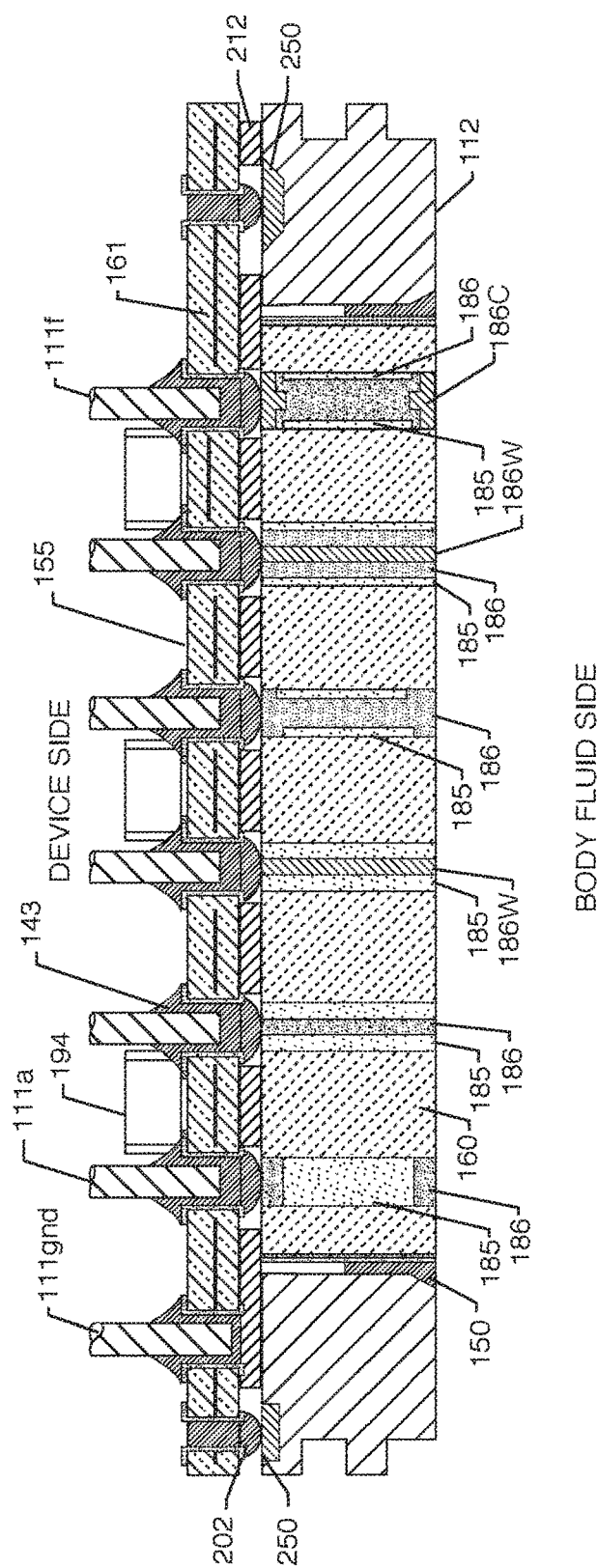
FIG. 48 is similar to FIG. 47 now showing the use of a solder bump for electrical connection.
Figure 49:
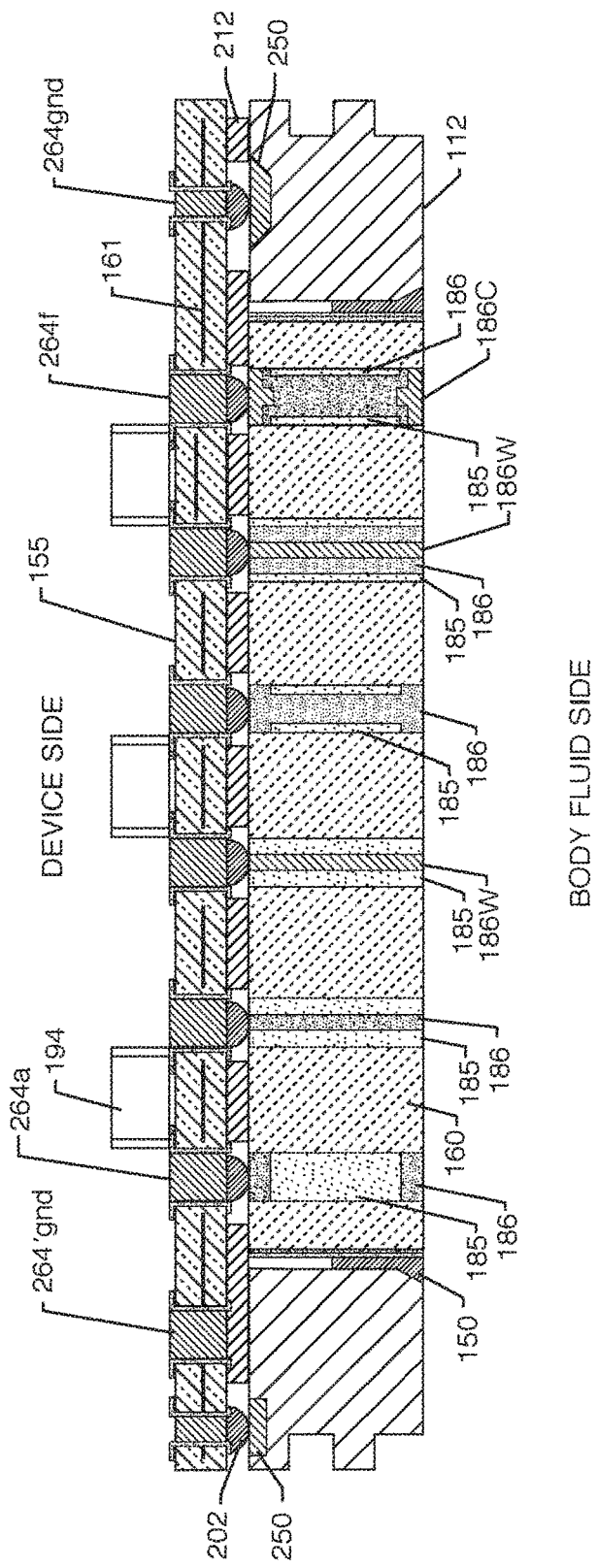
FIG. 49 is similar to FIGS. 47-48 now showing vias on the circuit board using conductive fills with solder bumps for making electrical connections.

FIGS. 25, 26 and 27 are very similar to FIGS. 48, 49 and 50 from U.S. Pat. No. 9,427,596 of which the present application is a continuation-in-part. Accordingly, U.S. Pat. No. 9,427,596 is fully incorporated herein by reference and by continuity. Referring to FIG. 48 of the '596 patent, one can see that there are pocket areas 248 (i.e. recess, indentation, divot, cup, channel) defined in the ferrule 216 (now 112) that receive a gold braze preform 250 and a thin layer of platinum or equivalent material 250b. During high-temperature gold braze reflow, in the '596 patent, the thin layer of platinum or equivalent material 250 becomes a metal addition in accordance with the '596 patent. In the present invention, this thin layer of platinum or equivalent material 250b has been eliminated. There is still a pocket that is formed 248, which can be relatively shallow since it defines a controlled thickness of a gold preform 250. During gold braze high-temperature furnace reflow, gold preform 250 cannot escape from the pocket area 248 due to gravitational forces. This is because it is fully contained or walled or dammed on the bottom and on all four sides like a swimming pool. Accordingly, gold preform 250 differs from the prior art in that the gold preform of the present invention does not braze two metals (the platinum metal addition to the titanium ferrule); rather, the gold preform is captured in the pocket in such a way that it cannot undesirably flow during high-temperature operations (such as during hermetic seal gold brazing) thereby forming a reliable and oxide-resistant pocket pad so that a reliable (free of titanium oxides) electrical attachment to a capacitor can be made. This allows the gold preform 250 to be just thick enough to prevent any oxide of titanium from coming through or penetrating the gold. For example, 50 microns of gold might be so thin that an oxide may penetrate it easily. Accordingly, 0.005 inches of gold is sufficient to block oxides of titanium. However, a gold preform that thin would be very difficult to handle in manufacturing, so in the present invention, gold preforms 250 (prior to brazing) could be on the order of 1 mil to 10 mils for ease of handling.

Gold preforms, as used and defined herein, can be substantially pure gold, but can also be alloys containing gold, alloys containing platinum, alloys containing palladium, alloys containing iridium, alloys containing germanium and also even nano-type structures. In other words, gold pocket pads 250, as described herein, can be any material that can be brazed to titanium or metallurgically bonded to titanium that will provide an oxide-resistant and low conductivity attachment surface. Gold preform area 250 could also consist of various types of conductive carbons.

FIG. 26 is very similar to FIG. 25, except that the pocket areas 248 are round instead of rectangular and the gold preforms 250 are cylindrical instead of rectangular solids.

FIG. 27 illustrates a rectangular feedthrough capacitor 132 mounted to the hermetic seal ferrule assembly 120 of FIG. 25. One can see that there are electrical connections 152 that can be a thermal-setting conductive adhesive, a solder or the like that makes an oxide-resistant and low impedance connection between the capacitor's ground metallization 142 and the gold braze filled pocket 248, 250. In this case, there are four attachment areas, which high-frequency simulation using PSpice has indicated, are adequate such that the feedthrough capacitor 132 will desirably divert undesirable EMI over a very broad range of frequencies. By using a small amount of electrical thermal-setting conductive adhesive 152, one also saves a significant amount of material cost. This is because conductive polyimides or epoxies 152 are generally full of silver, which is an expensive material. Also by spacing the pockets 248, as shown, one also greatly limits the amount of gold used 250, in this case, just to four pocket areas.

Referring once again to FIG. 27, it will be appreciated that the discrete pocket areas 248, 250 and 248', 250' also have two other pockets on the other end of the feedthrough capacitor (that are not visible in this isometric view). It will also be appreciated that the two end pockets on each end 248, 248' and their corresponding gold fills 250 and 250' may be extended to be continuous. It will also be appreciated that these pockets could be disposed along the long side of the feedthrough capacitor instead of the ends, as illustrated. In an alternative embodiment, the pocket 248 could go all the way around the perimeter of the feedthrough capacitor forming a pocket into the ferrule and then filled with gold, such that the electrical attachment material 152 could be disposed completely around the perimeter between the feedthrough capacitor metallization and the ferrule gold-filled pocket 250.

Figure 28:
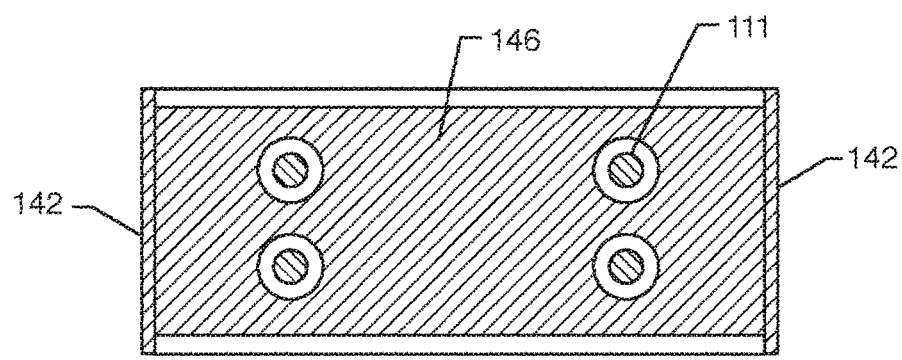
FIG. 28 is taken generally from section 28-28 from FIG. 27 and illustrates the ground electrode plates of feedthrough capacitor.

FIG. 28 is taken generally from section 28-28 from FIG. 27 and illustrates the ground electrode plates 146 of feedthrough capacitor 132. As one can see, the ground electrode 146 is exposed on both of the short ends of the rectangular feedthrough capacitor where the ground metallization 142 is connected to it.

Figure 29:
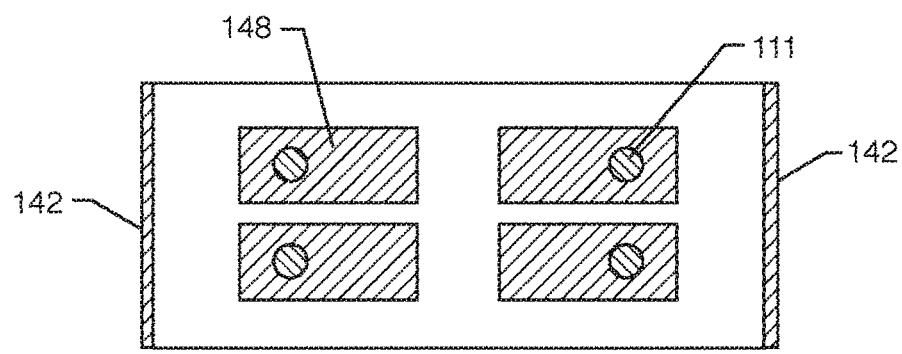
FIG. 29 is taken generally from section 29-29 from FIG. 27 and illustrates the feedthrough capacitor's four active areas.

FIG. 29 is taken generally from section 29-29 from FIG. 27 and illustrates the feedthrough capacitor's four active areas 148. In accordance with all feedthrough capacitors, these active areas 148 are electrically isolated from each other and each one of them are electrically connected or conducted to a respective terminal pin or lead wire 111, as shown.

Referring once again to FIG. 28, it will be appreciated that the metallizations 142 shown on both ends, need not be placed across the entire end. In other words, metallization 142 will be electrically effective if it only contacts a portion of the ground electrode plate 146.

Figure 29A:
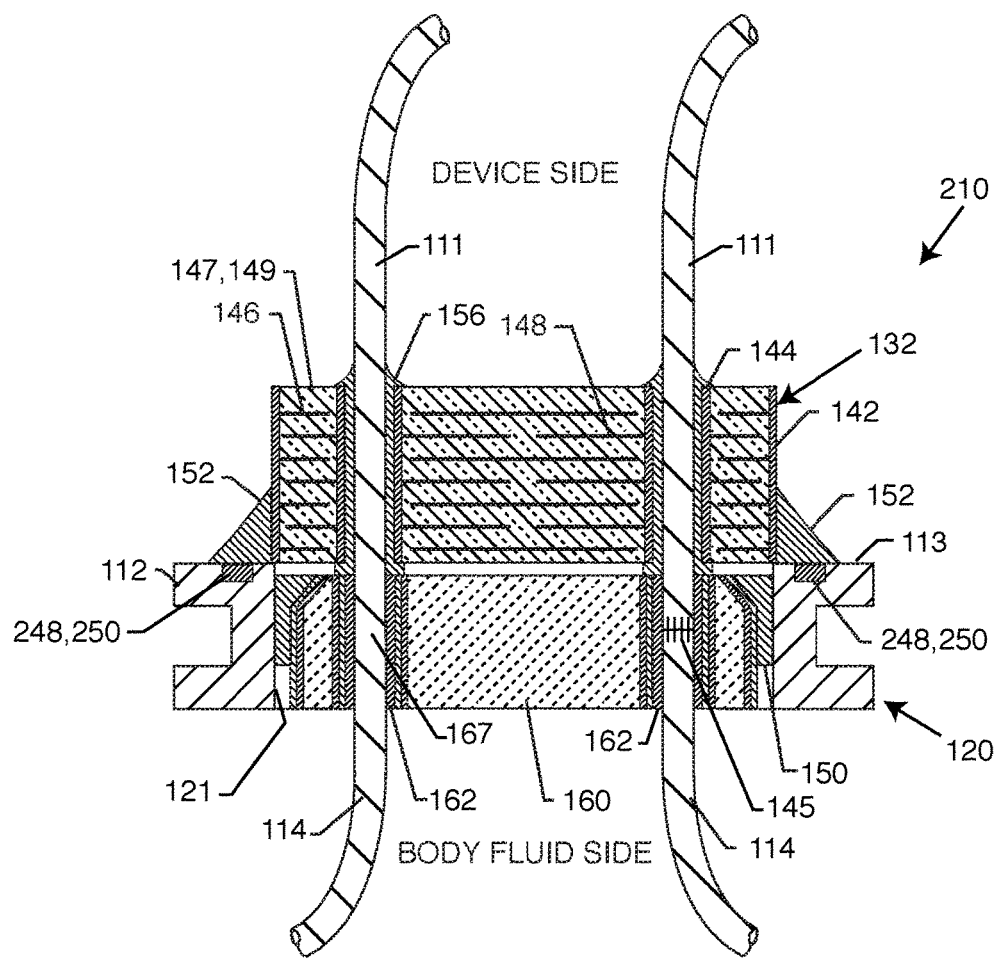
FIG. 29A is taken generally from section 29A-29A from FIG. 27 and illustrates the feedthrough capacitor with gold pocket pad attachments shown in cross-section.

FIG. 29A is taken from section 29A-29A from FIG. 27 and illustrates both the feedthrough capacitor 132, the lead-wires 111 and the hermetic seal subassembly 120 shown in cross-section. In this cross-section, one can see the alumina ceramic insulator 160, which has been gold brazed 162 to leadwires 111 and also gold brazed 150 into a ferrule 112 opening. The feedthrough capacitor 132 ground metallization 142 is electrically connected to the gold bond pads 248, 250 of the present invention by either a thermal-setting conductive adhesive or a solder 152.

Referring again to FIG. 29A, one can see that the electrical attachment material 152, which can be of thermal-setting conductive adhesive or of solder, electrically contacts not only the gold pocket pad 248, 250, but some of the electrical attachment material 152 also contacts the top portion of the ferrule 113. This is generally acceptable because it has been found both through testing and high frequency modeling, that a low impedance electrical connection suitable for high frequency performance is achieved by contacting only a portion of non-oxidized ferrule surface, as shown.

Figure 1:
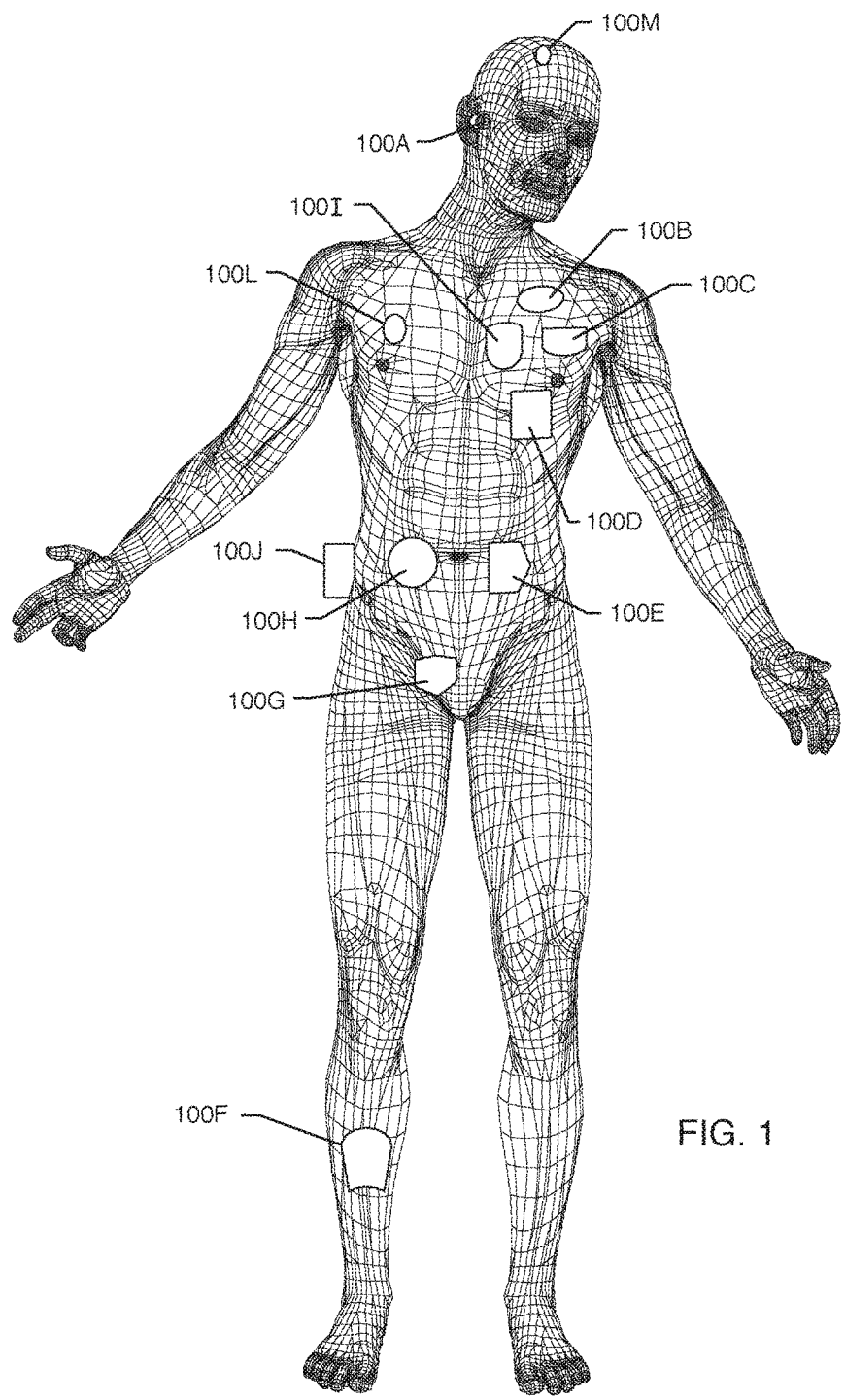
FIG. 1 is a wire-formed diagram of a generic human body showing a number of exemplary implantable medical devices.
Figure 2:
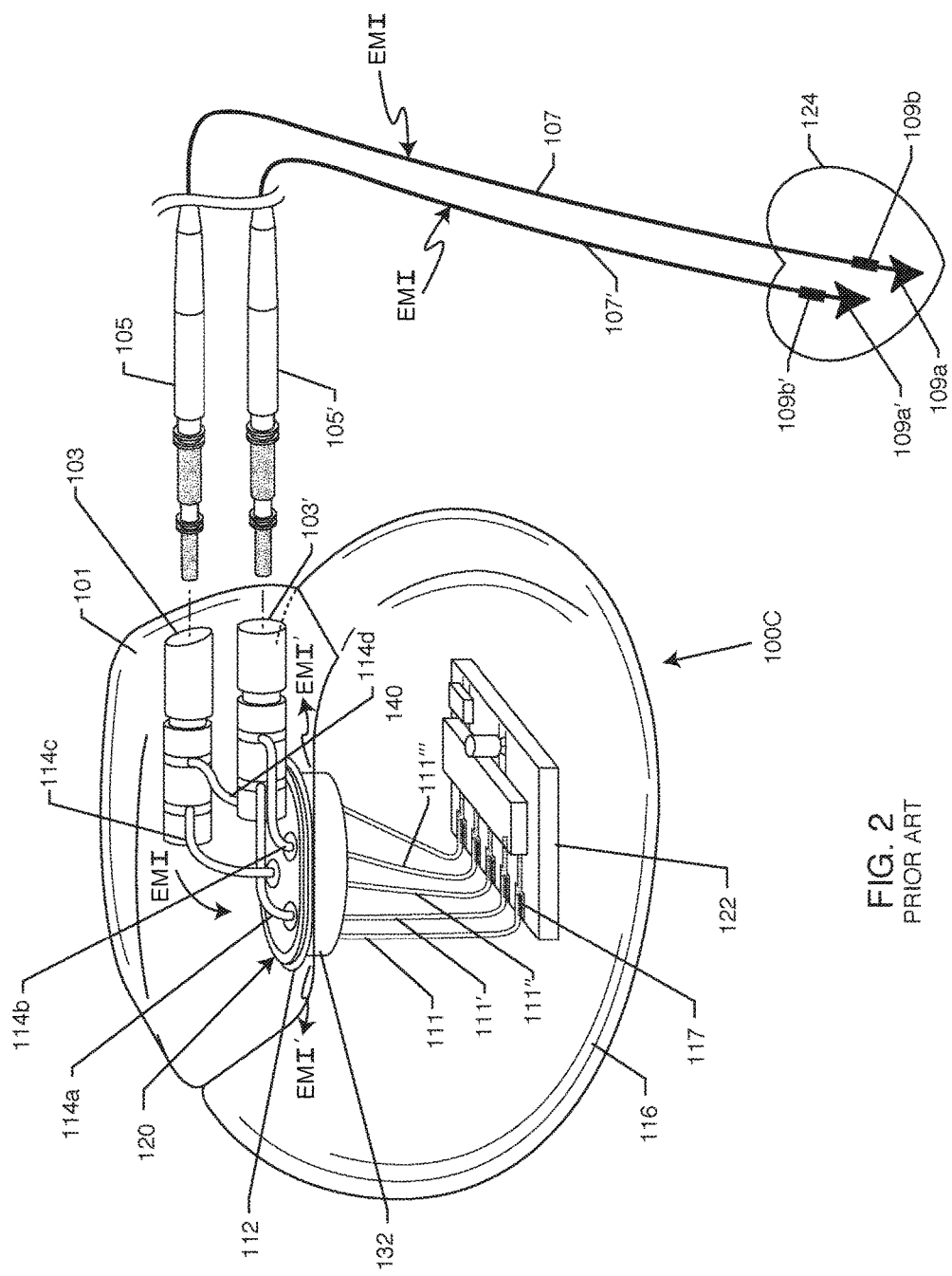
FIG. 2 is a side view of a prior art cardiac pacemaker.
Figures 3, 3A:
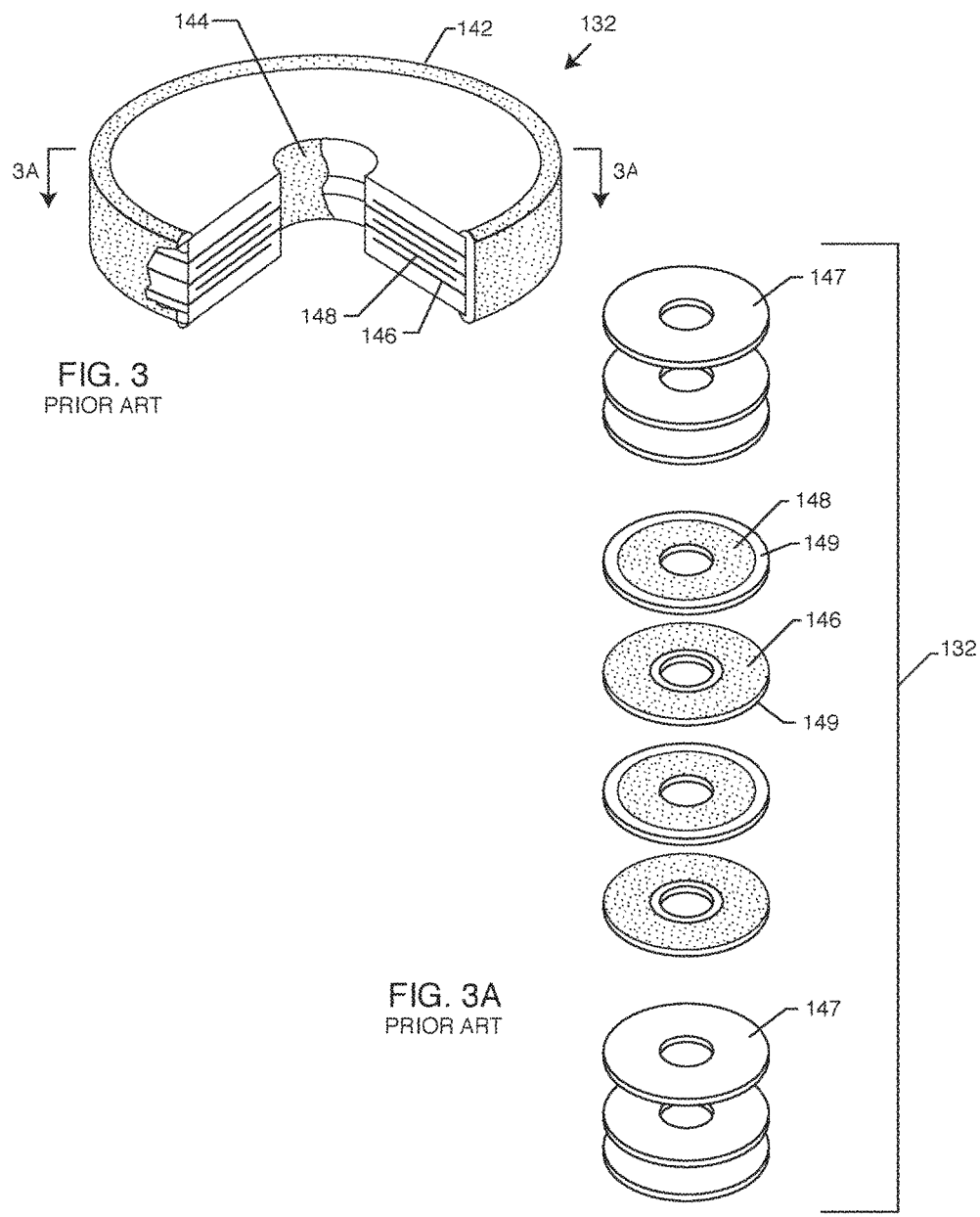
FIG. 3 is an isometric cut-away view of a prior art unipolar feedthrough capacitor.
FIG. 3A is an exploded isometric view of the unipolar capacitor of FIG. 3.
Figure 4:
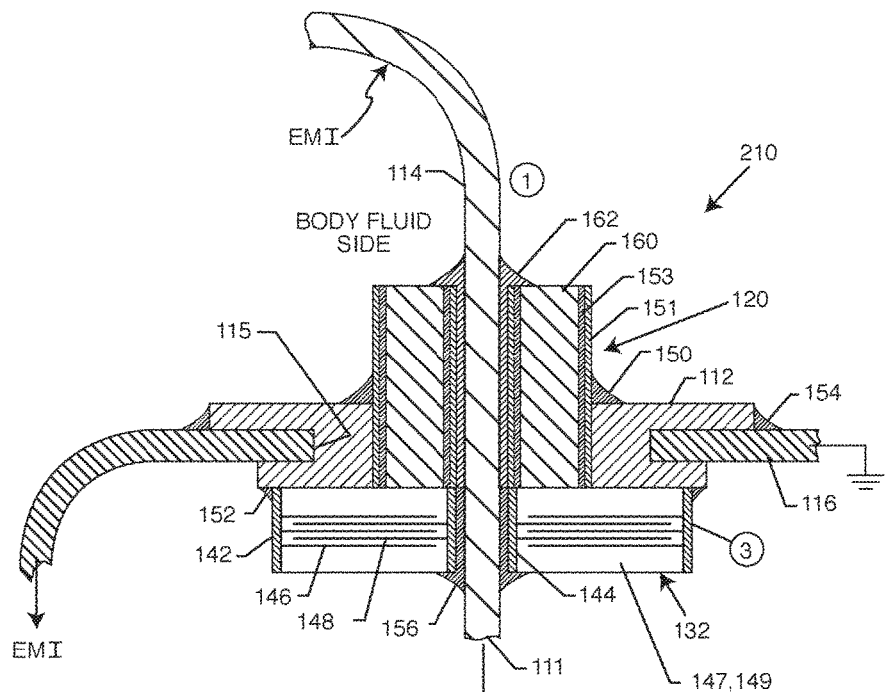
FIG. 4 is a sectional view of a prior art hermetic feedthrough terminal.
Figure 4A:
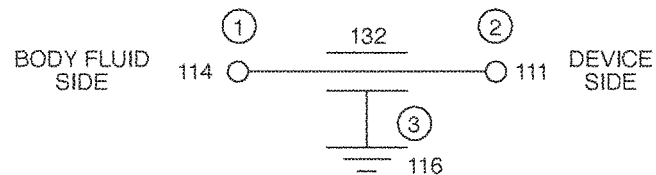
FIG. 4A is an electrical schematic of the structure of FIG. 4.
Figure 5:
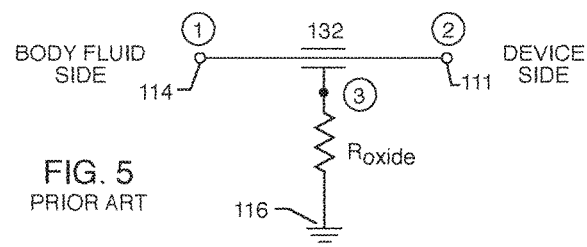
FIG. 5 is very similar to the schematic of FIG. 4A, except in this case, there is an oxide $R_{oxide}$.
Figure 6A:
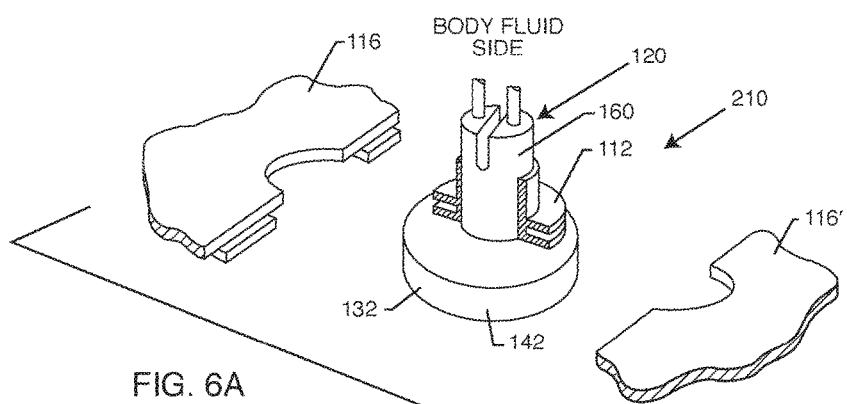
FIG. 6A is taken from FIG. 21 of U.S. Pat. No. 5,333,095 where one can see that there is a feedthrough capacitor that is mounted onto a ferrule of a hermetic seal subassembly.
Figure 6B:
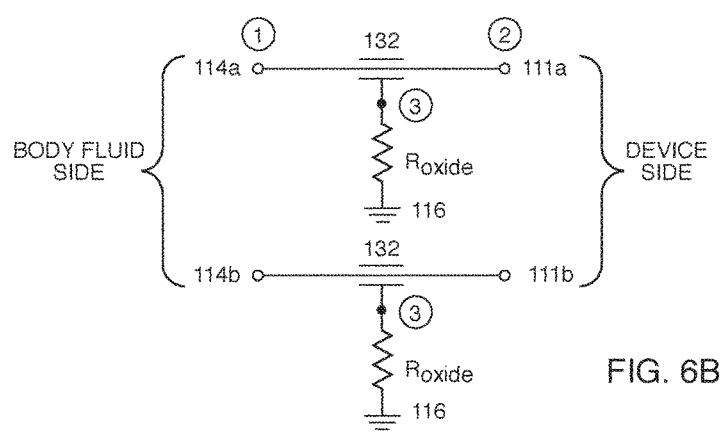
FIG. 6B illustrates the schematic of the bipolar feedthrough capacitor of FIG. 6A.
Figure 7A:
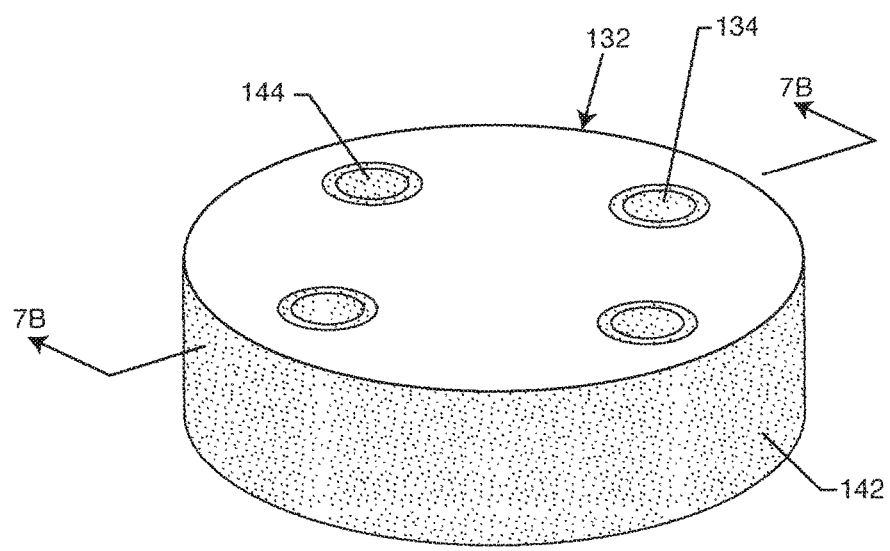
FIG. 7A illustrates a quad polar feedthrough capacitor.
Figure 7B:
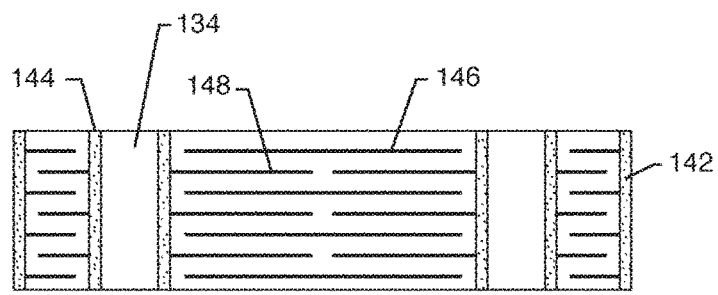
FIG. 7B is a sectional view taken generally from FIG. 7B-7B from FIG. 7A, which illustrates the quad polar feedthrough capacitor of FIG. 7A.
Figure 8:
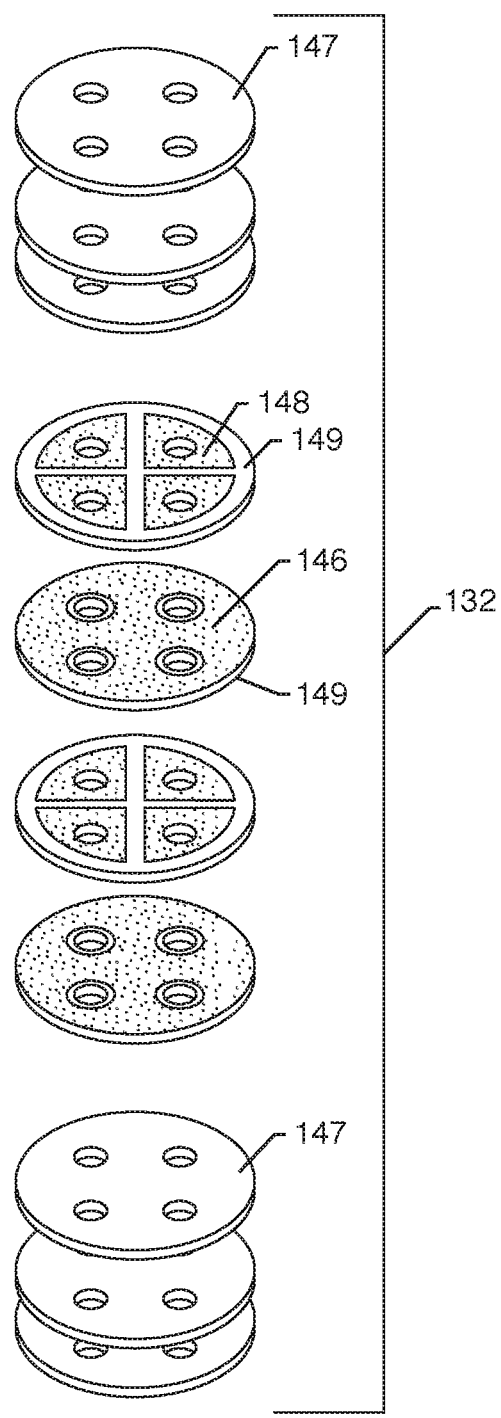
FIG. 8 is an exploded isometric view of the unipolar capacitor previously illustrated in FIGS. 7A and 7B.
Figure 9:
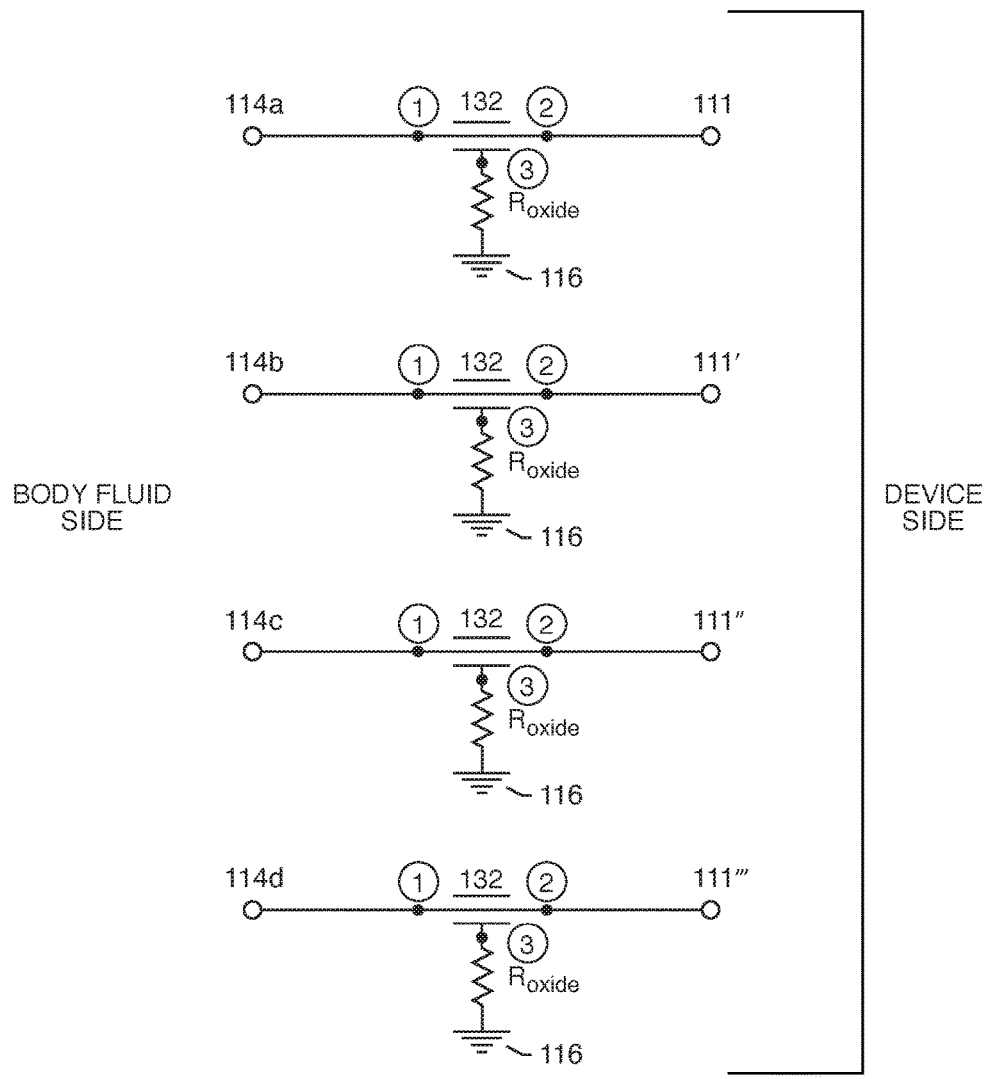
FIG. 9 is the schematic drawing of the feedthrough capacitor of FIG. 8, but in this case, this is after the feedthrough capacitor has been installed to a hermetic seal ferrule and insulator with pins.
Figure 15:
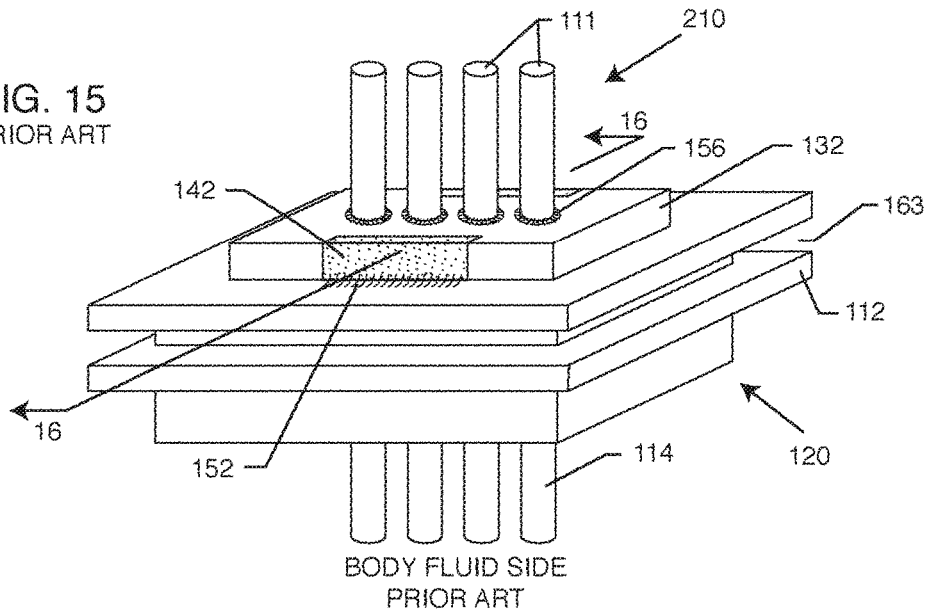
FIG. 15 illustrates the feedthrough capacitor installed to the hermetic seal assembly as previously described in FIGS. 11 and 12.
Figure 16:
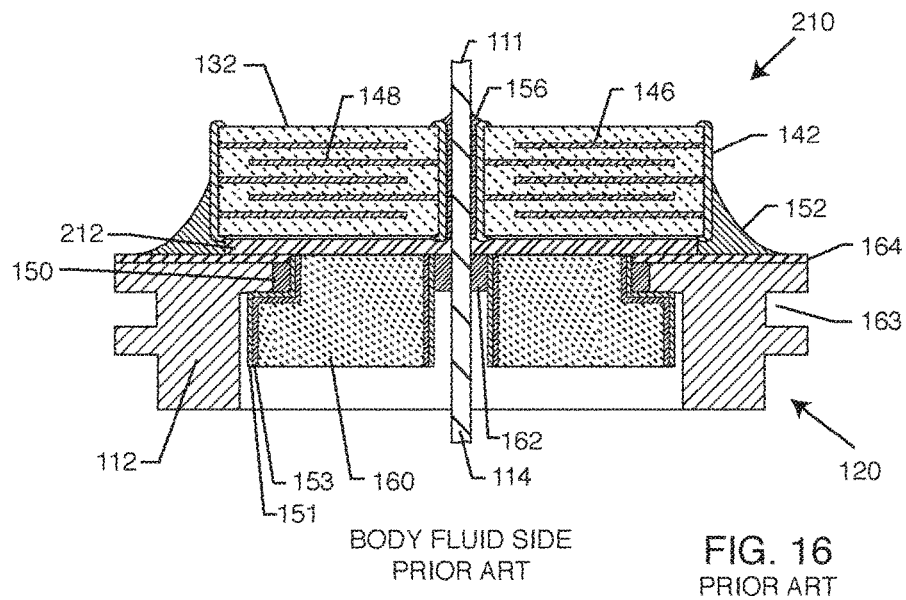
FIG. 16 is taken generally from section 16-16 from FIG. 15.
Figure 17:
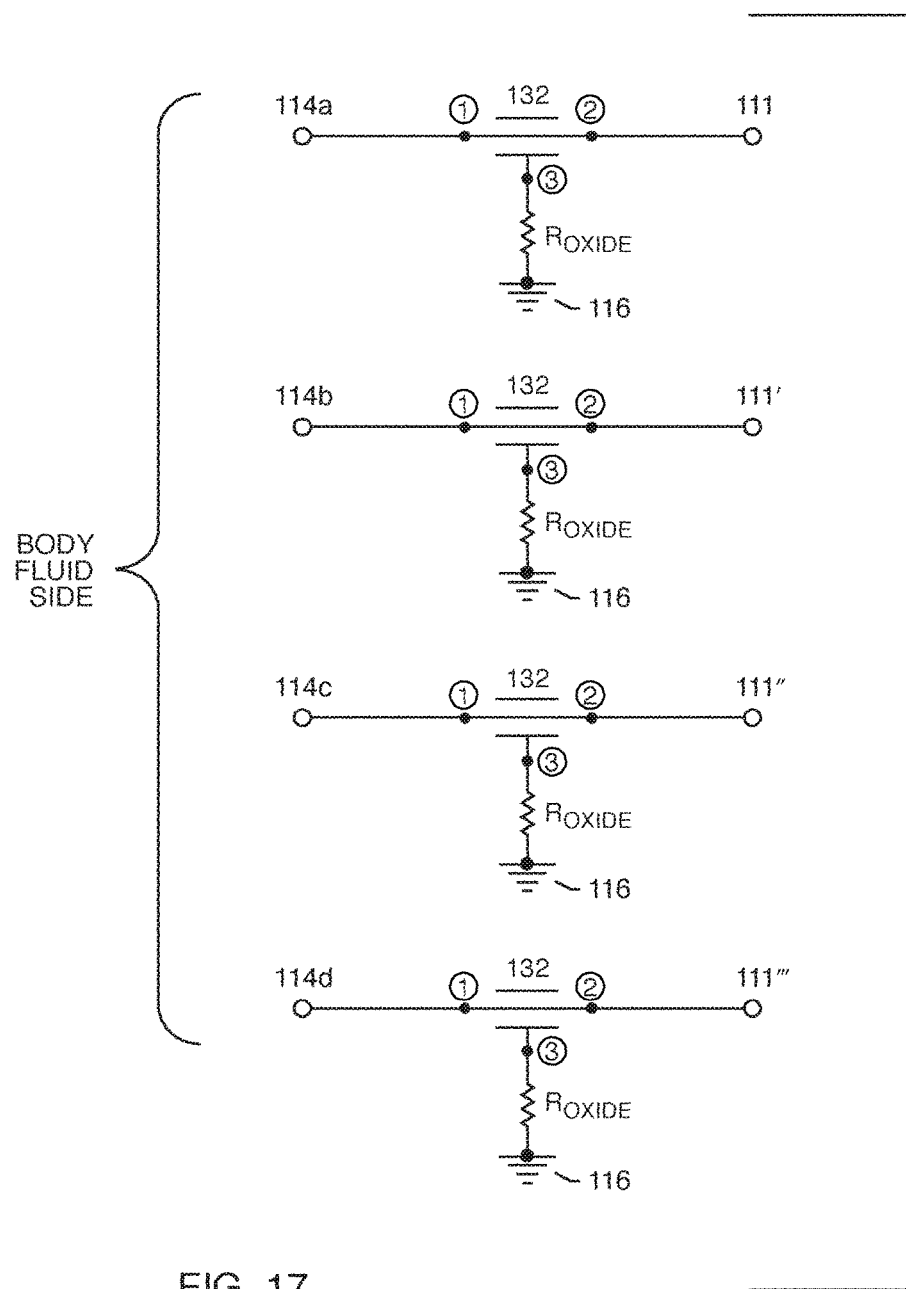
FIG. 17 is a schematic diagram illustrating the undesirable presence of an oxide in the ground path of the quad polar feedthrough capacitor.
Figure 18:
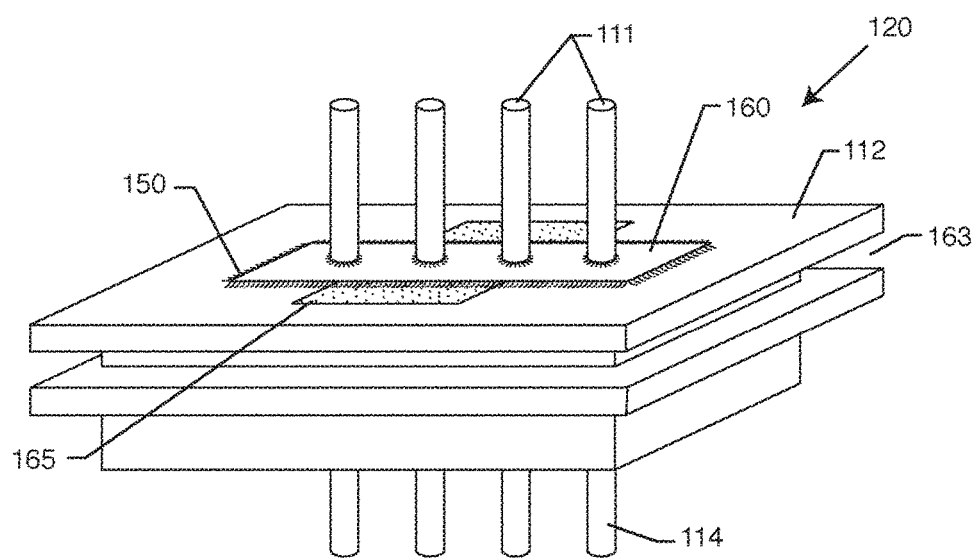
FIG. 18 shows the use of novel gold braze bond pads that are one embodiment of a novel feature of the '596 patent.
Figure 19:
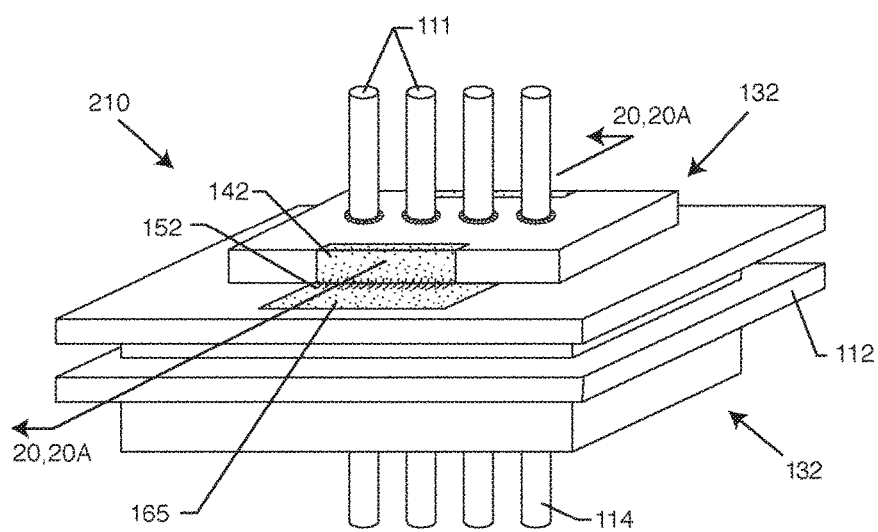
FIG. 19 shows that the feedthrough capacitor ground metallization is electrically attached by a thermal-setting conductive adhesive directly to the gold bond pad area.
Figure 20:
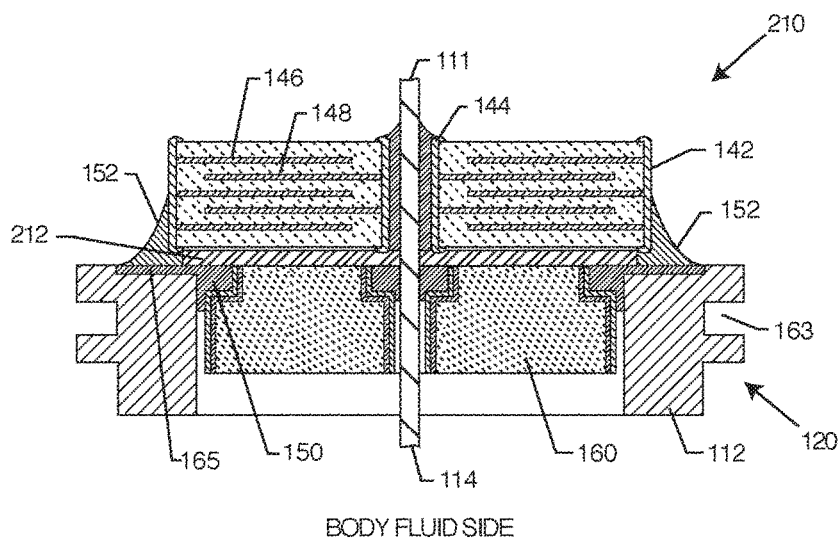
FIG. 20 is a sectional view taken from section 20-20 from FIG. 19.
Figure 20A:
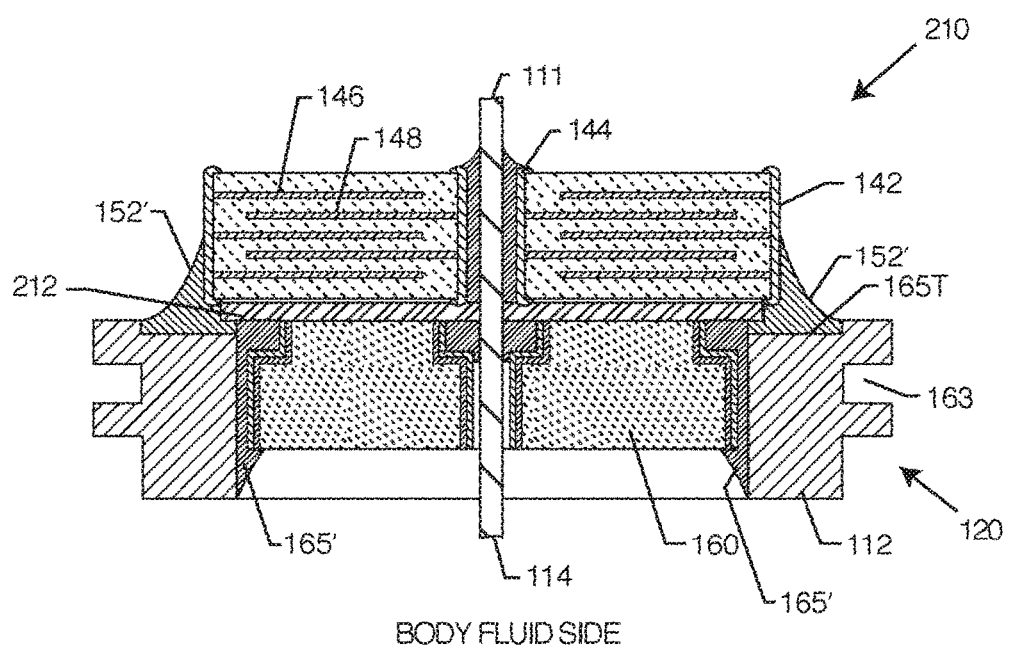
FIG. 20A is taken from section 20A-20A from FIG. 19 and shows a more realistic structure of what happens to the gold braze of the gold bond pad area.
Figure 21:
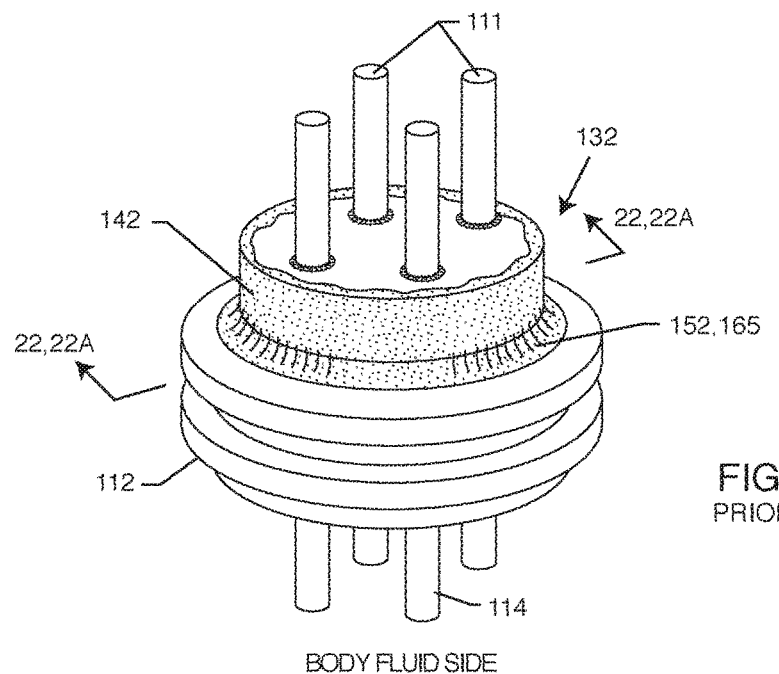
FIG. 21 is an isometric view taken from FIG. 23 of the '779 patent.
Figure 22:
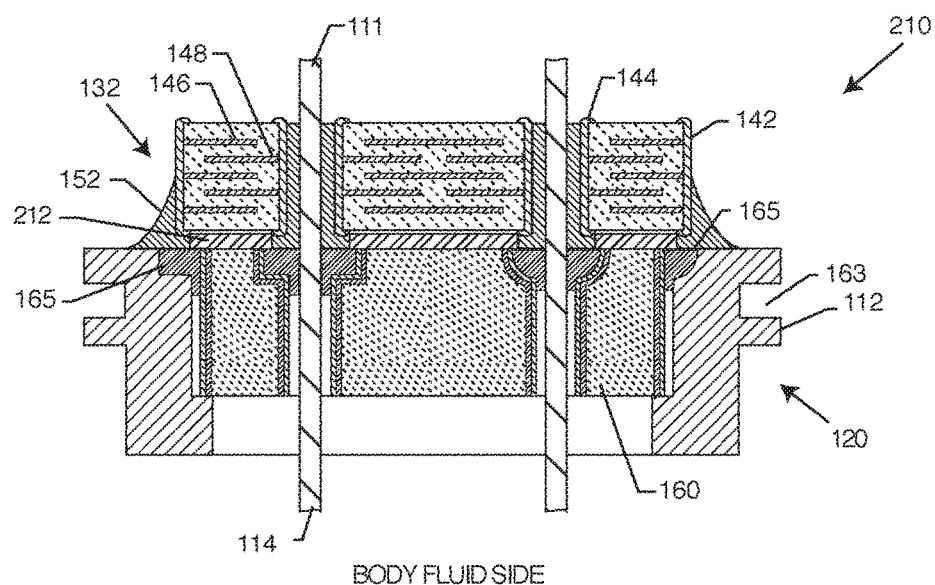
FIG. 22 is a sectional view of the structure of FIG. 21.
Figure 22A:
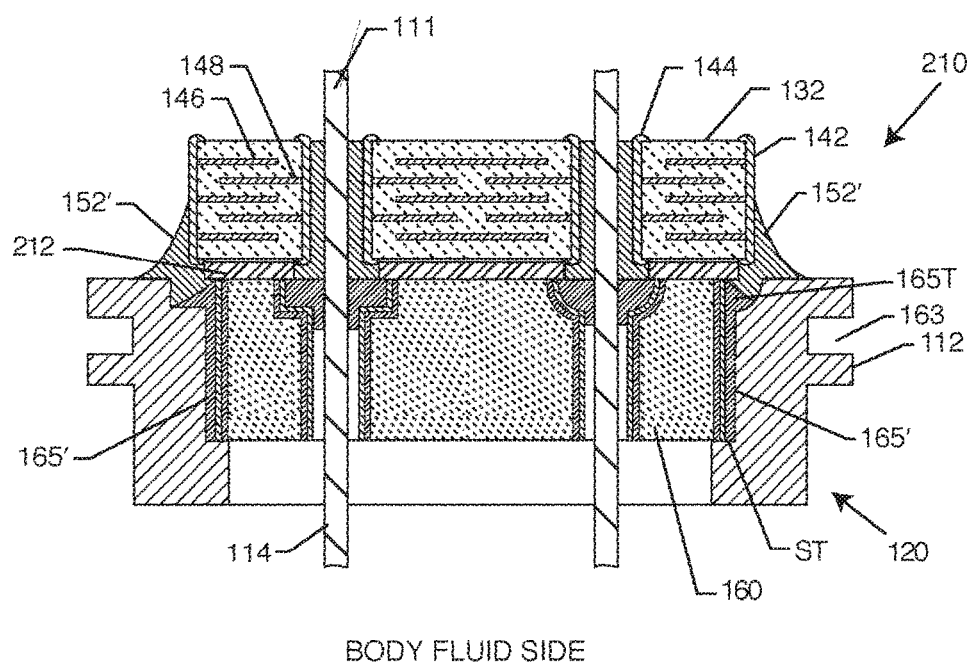
FIG. 22A is taken from section 22A-22A from FIG. 21 which is similar to FIG. 22, but now illustrates what really happens to the gold braze during high-temperature gold braze furnace reflow operations.
Figure 23:
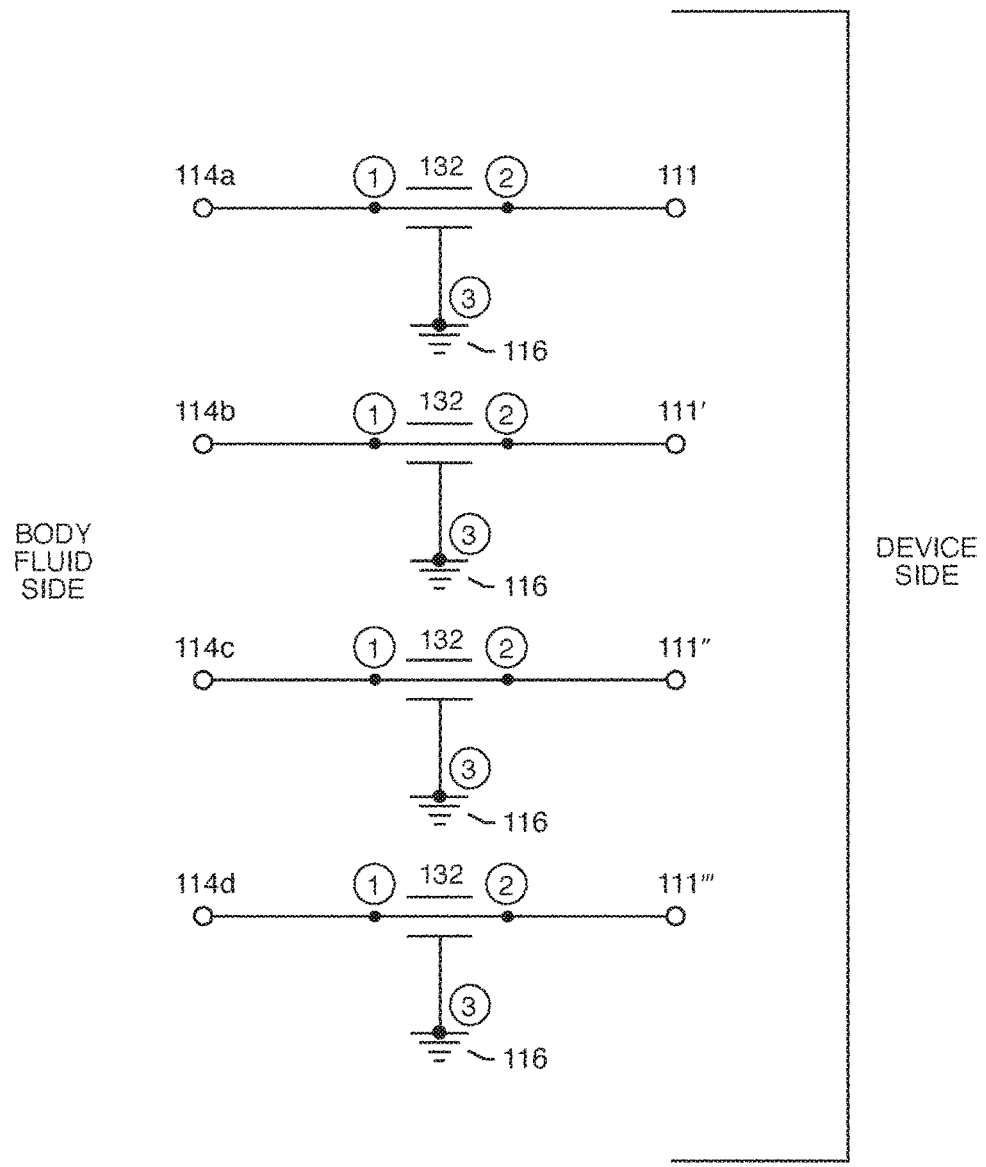
FIG. 23 is an electrical schematic taken from FIGS. 20 through 22A.
Figure 24:
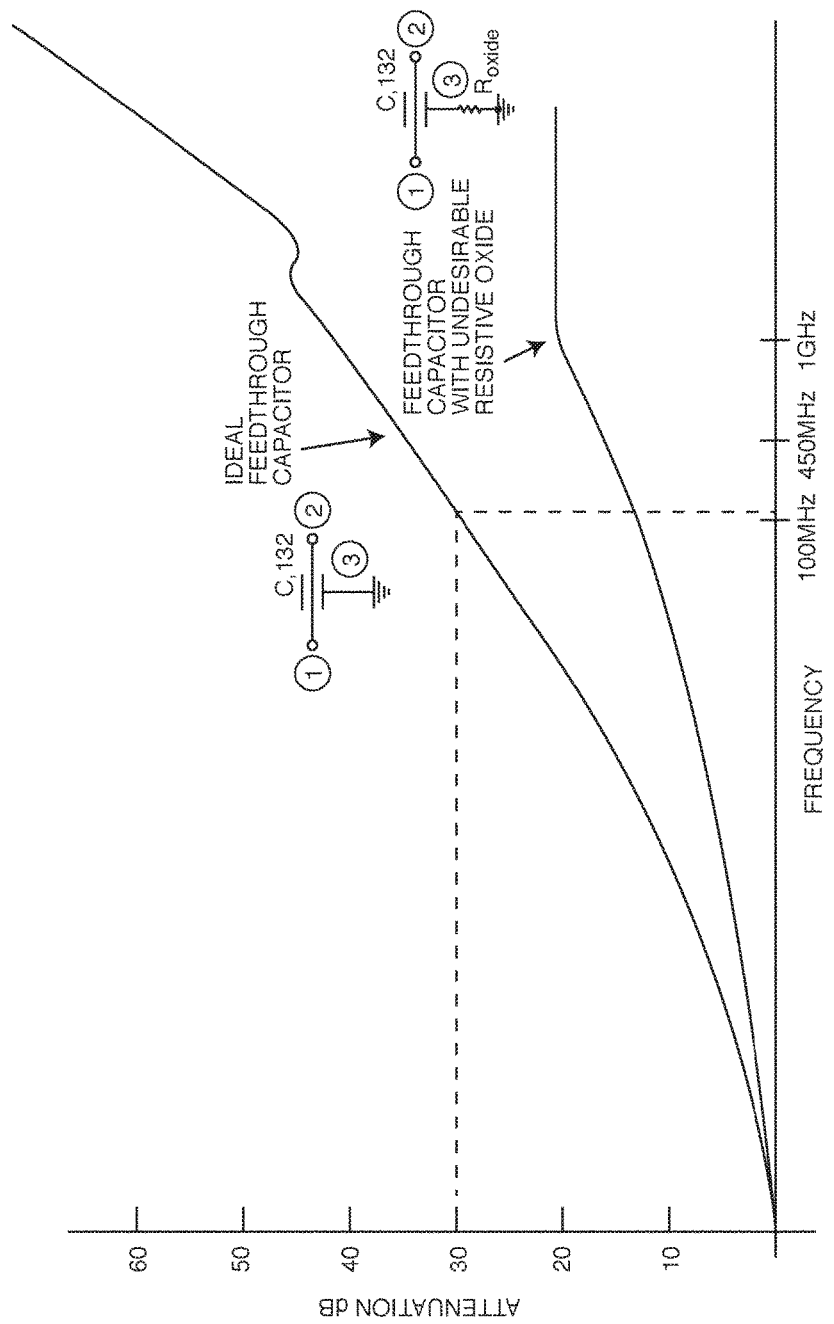
FIG. 24 illustrates filter performance otherwise known as attenuation or insertion loss curves versus frequency.

Referring back to prior art FIGS. 22 and 22A, there is an insulating washer 212 disposed between the feedthrough capacitor and at least one of the insulator 160 and ferrule 112. It will be appreciated that in FIGS. 29A, 29B and 30, these insulating washers are not shown for clarity, but in general, would be present. In some drawings, the insulation washer is illustrated. For example, in FIGS. 41 and 41A, the insulating washer is element 212.

Referring to the leadwire on the left-hand side in FIG. 29A, which is 111, 114, one can see that the leadwire is continuous from the device side all the way through the body fluid side. On the right-hand side of FIG. 29A, one can see that the leadwire is not continuous and has a joint located within the gold braze 162 of the hermetic seal 160. Optionally, these two leadwire segments have been pre-brazed together 145, as shown. In generally, on the right side, the body fluid wire leadwire 114 would be of a generally low-cost material, such as tantalum, niobium or even titanium. However, this material would be heavily oxidized. It is joined at location 145 to a palladium, a platinum, or a more expensive leadwire, which would be less prone to oxidation. As known in the industry, leadwires 111 on the device side, could also comprise platinum-iridium or palladium-iridium or other alloys. Because these materials are not as heavily oxidized as the body fluid side leads, a suitable electrical connection 156 can be accomplished between leadwires 111 and the active metallization 144 of the feedthrough capacitor 132. The novel joining of pins within the hermetic seal gold braze is more thoroughly described in U.S. patent application Ser. No. 15/603,521, the contents of which are incorporated herein fully by reference.

Figure 29B:
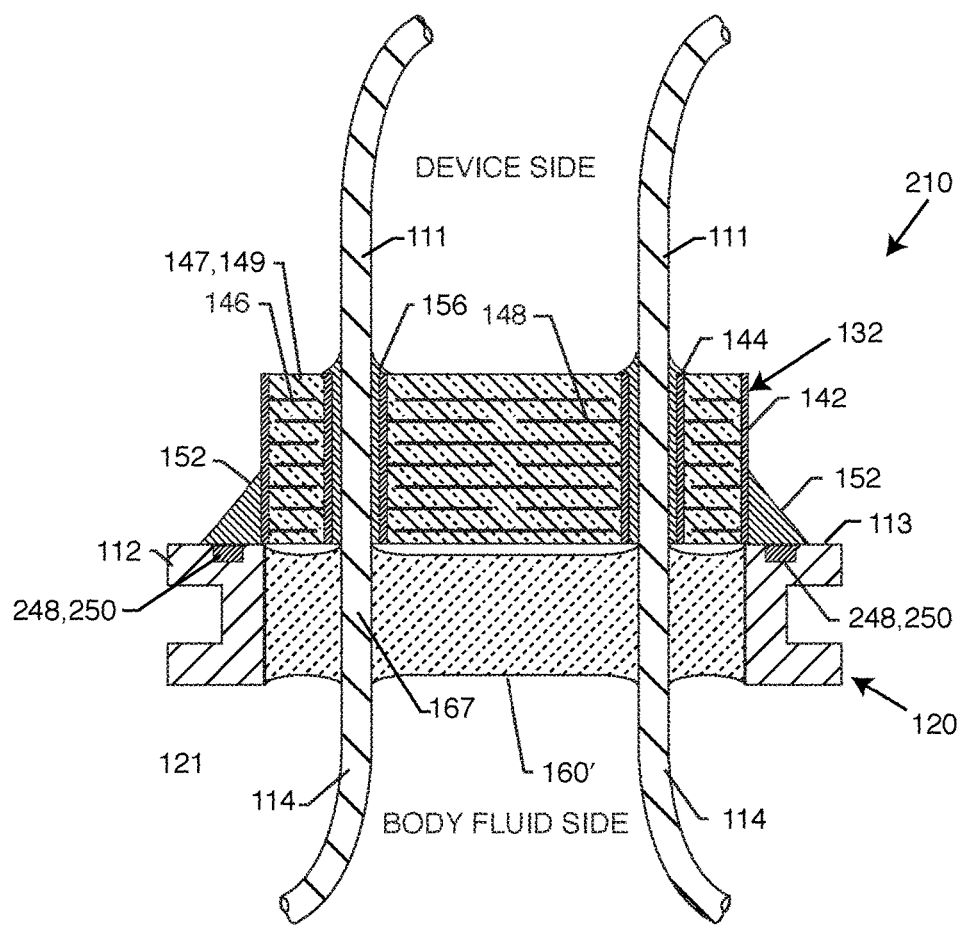
FIG. 29B is a sectional view taken generally from section 29B-29B from FIG. 27 and illustrates that the hermetic seal may be of glass.

FIG. 29B is taken from section 29B-29B from FIG. 27 and is very similar to the cross-section previously illustrated in FIG. 29A. In this case, the gold brazed alumina ceramic insulator 160 has been replaced by a glass seal 160'. This glass seal may be a compression glass, a fusion glass or a ceramic glass composite. In the case of glass seals, there is no gold braze required as the glass makes a hermetic seal directly to the ferrule and also to leadwires 114, 111, as indicated. In general, the glass seals start out as a pellet, including an outer diameter or perimeter designed to fit the ferrule opening, and also, one or more passageways to receive leadwires 114, 111. In a glass reflow operation, hermetic seals are formed between one of the types of glasses and both the ferrule and the leadwires, at the same time. It will be appreciated that this leaves a problem, in that, there is no gold to attach to in order to form an oxide-free resistance and low impedance electrical connection 152 between the capacitor ground metallization 142 and ferrule 112.

Referring once again to FIG. 29B, the ferrule would first be fabricated by machining sintered metal or other metal-forming processes. Then, this metal-forming operation would include forming of the pockets 248. The next step would be to place gold preforms in these pockets and raise them to an elevated temperature, such as a gold brazing temperature so that the gold will wet and form an oxide resistant metal attachment pad. Glass sealing is generally done in a much lower temperature than gold brazing operations. So once the ferrule and it's associated gold pockets 250 are formed, then the leads may be placed and the glass preform may be placed such that the hermetic seal between the glass, the leads and the ferrule is performed without reflowing or disturbing the previously manufactured gold braze pocket 250.

Figure 30:
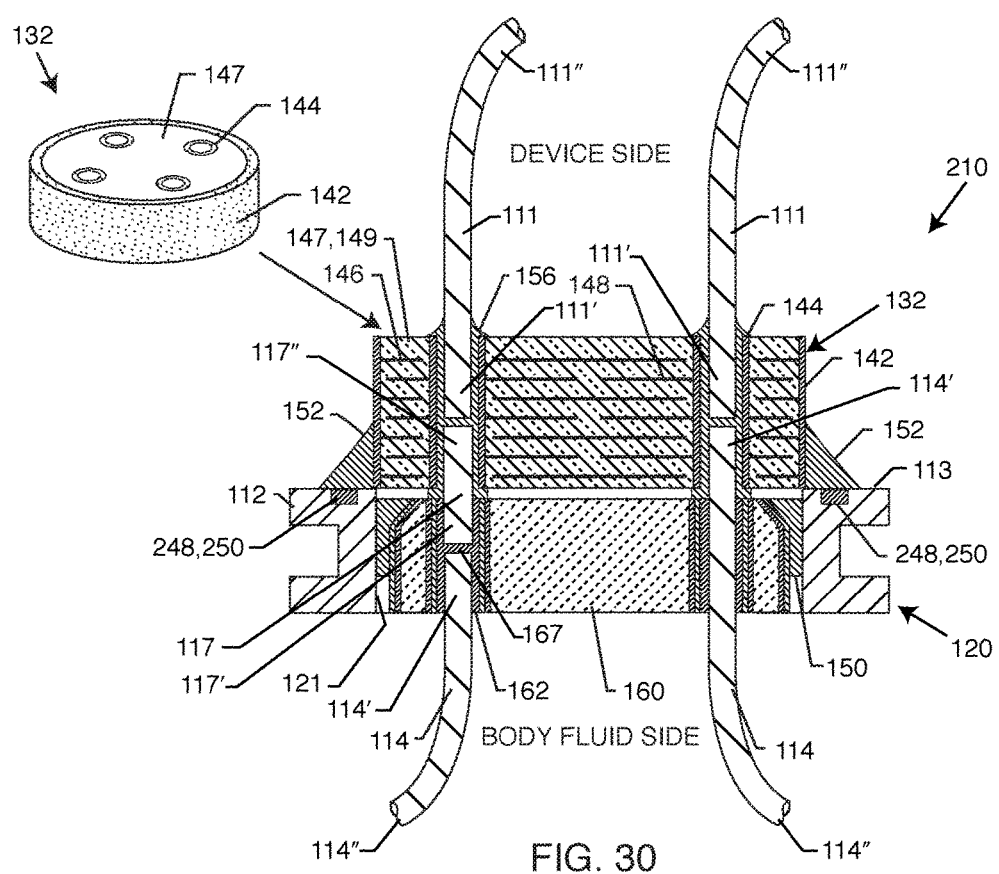
FIG. 30 is a sectional view illustrating a number of alternatives of the present invention.

FIG. 30 illustrates a number of alternatives of the present invention. On the left hand of the cross-section shown in FIG. 30, one can see that the body fluid side leadwire 114 is segmented by a leadwire segment 117. As will be shown, gold braze 162 mechanically and electrically joins the body fluid side leadwire 114 to the leadwire segment 117. This is important such that low cost leadwires 114, instead of pure platinum or palladium, can be used. This includes leadwires of tantalum, niobium and the like. Referring once again to FIG. 30, one can see that on the left, there is a low cost leadwire 111 that is disposed between the feedthrough capacitor and device electronics (not shown) that would generally be of copper or other low-cost material. An electrical connection material 156, which can comprise of solder, thermal-setting conductive adhesive or the like, is used to electrically and mechanically connect the low-cost device side leadwire to segment 117. Segment 117 would generally be of short platinum or palladium pin, such that it is readably connectable to the inside diameter metallization 144 of the feedthrough capacitor. Since it is relatively short, it would be of very low cost. One is referred to U.S. patent application Ser. No. 15/603,521, the contents of which are incorporated herein fully be reference, which fully describes the novel lead segment 117, which is co-brazed 162 to a body fluid side lead 114. Now referring to the right-hand side leadwire as illustrated in the cross-section of FIG. 30, one can see that the body fluid side leadwire 114 extends approximately half way up into the inside diameter area of the feedthrough capacitor 132. In this case, there is a low-cost leadwire 111 generally of copper or insulative copper or the like disposed from the feedthrough capacitor through hole or via to device electronic circuits (not shown). In this case, the body fluid side leadwire 114 would generally be of platinum, palladium or alloys of platinum or palladium containing iridium or the like. One is referred to U.S. patent application Ser. No. 15/844,683 for a more complete description. Referring to the embodiment illustrated on the right side of FIG. 30 and in accordance with the present invention, the feedthrough capacitor 132 outside diameter metallization 142 is electrically connected with an electrical connection material 152 at least in part to the novel gold brazed pockets and gold braze fill 248, 250. Importantly, this provides an oxide-resistant and very low impedance high-frequency electrical connection so that the feedthrough capacitor 132 can properly act as a broadband low pass filter. Now referring to FIG. 30A of U.S. patent Ser. No. 15/603,521, one will appreciate that the feedthrough capacitor 132 can be replaced by a circuit board. The leadwire segment 117 and the device side leadwire 111 would be co-joined in a via of the circuit board. Filtering would be accomplished by the mounting of MLCC or equivalent chip capacitors on the circuit board, as described in Ser. No. 15/603,521, the contents of which are incorporated herein fully be reference. It is understood from reading this disclosure that the present invention may be utilized with the use of different types of capacitors, including types mounted on circuit boards, including but not limited to chip capacitors, MLCC, stacked film capacitors or tantalum chip capacitors.

Figure 31:
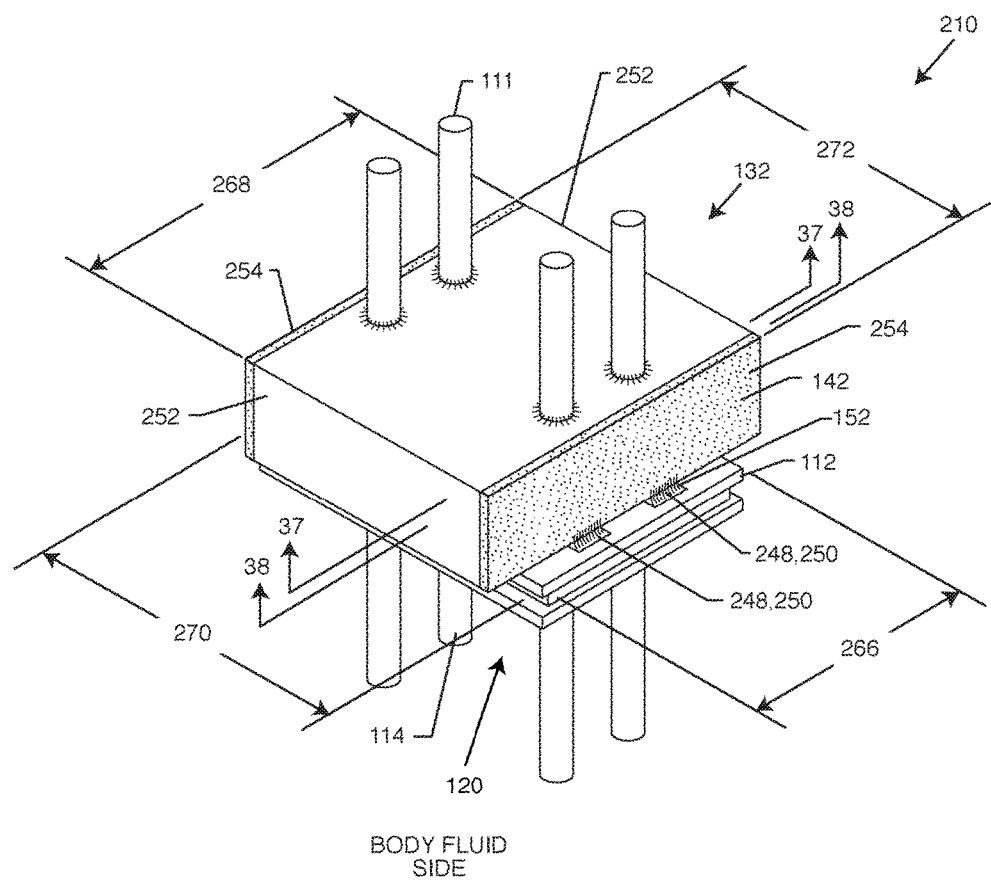
FIG. 31 is very similar to the feedthrough capacitor filter assembly from FIG. 27, except in this case, the feedthrough capacitor is substantially wider than the ferrule.

FIG. 31 is very similar to the feedthrough capacitor filter assembly 210 from FIG. 27, except in this case, the feedthrough capacitor 132 is substantially wider than the ferrule 112. The ferrule width, as illustrated, is designated as 266. The capacitor width is shown as 268 and is substantially wider than ferrule width 266. In the opposite axis, the length of the feedthrough capacitor 272 is sufficiently shorter than the ferrule width 270 such that the capacitor ground metallization 142 winds up at least partially over the novel pockets 248 and gold pocket pad 250. This enables the important high-frequency electrical connection 152, between the capacitor ground metallization 142 and gold braze areas 250. Referring back to FIG. 31, having the capability to have the feedthrough capacitor wider 268 than the ferrule 266 lends a tremendous amount of volumetric efficiency. In general, feedthrough capacitor active electrodes are a square law. This is because they are an area, either having a diameter, a square or a length and a width. By making the electrode areas wider, one greatly increases the effective capacitance area ECA and ends up with a much more highly volumetrically efficient feedthrough capacitor. In other words, a great deal more capacitance can be put into a relatively thin area, which is very important for AIMD internal construction. As previously described, the ferrule 112 is designed to be laser-welded into an opening of an AIMD housing 116 (not shown). During laser welding, the localized area of the ferrule 112 gets very hot. Importantly, the feedthrough capacitor 142 is only thermally connected to a relatively small electrical connection material 152 at both of its end, as illustrated. The part of the feedthrough capacitor that overhangs the ferrule, has no electrical connection material and is thereby, thermally "free to float." In other words, during laser welding, underneath the side of the feedthrough capacitor designated as 270, very little to no thermal stress is imparted to the relatively fragile ceramic capacitor 132. It will be appreciated that thermal-setting conductive adhesives and solders have a very high metal content so that they are highly electrically conductive. Along with high electrical conductivity typically comes relatively high thermal conductivity. Accordingly, as illustrated in FIG. 31, by minimizing the electrical connection area to a minimum, one also greatly reduces the thermal conductivity and the thermal stress to the feedthrough capacitor 132. Referring once again to FIG. 31, one can see that this novel construction allows the feedthrough capacitor 132 to be larger without increasing its height. This turns out to be critically important for two recently granted inventions. This includes U.S. Pat. Nos. 9,014,808 and 9,757,558, the contents of both of which are incorporated fully herein by reference. In particular, these inventions relate to novel low k dielectrics to be used as the primary EMI filter as described herein as the feedthrough capacitor or the MLCC capacitors, which are generally disposed at or near the point of entry of implanted leadwires into the housing of an AIMD. In the past, higher k dielectrics have been used for these filters resulting in very low electrode plate counts. This results in a high internal ohmic loss, which increases the capacitors equivalent series resistance.

Referring once again to FIG. 31, one can appreciate that the geometries can be reversed. That is, the capacitor can be terminated along the other two long sides, such that it overhangs the two ends of the ferrule. This can be important for patient comfort where it is important that the AIMD housings be relatively thin. This is because AIMD housings are designed to be implanted in a tissue pocket area. For example, for cardiac pacemakers are typically implanted in a pocket formed just above the pectoral muscle. Early model pacemakers were quite uncomfortable for patients because they were so thick. Modern pacemakers are much thinner and are much more comfortable for the patient. Accordingly, by reversing the geometry, as illustrated in FIG. 31, one can also keep the feedthrough capacitor relatively narrow, again for patient comfort.

The use of low k dielectrics is important today because implantable medical devices are increasingly implanted in humans that require MRI scans. MRI scanners involve a very intense and high amplitude RF field environment. For example, a 1.5 Tesla scanner produces a very powerful pulsed RF field at 64 MHz. Therefore, the feedthrough capacitor must be able to divert a very large amount of this RF current to the AIMD housing without itself overheating. Importantly, this means that the feedthrough capacitor's (or MLCC chip capacitor's) internal resistance or ESR be extremely low. Accordingly, the inventors are working to develop a new mid k dielectric of approximately 500 k in accordance with the U.S. Pat. No. 9,757,558 patent. Traditional dielectrics have been 2,000 to 2,600 k. So, the problem becomes one of how to get the same capacitance value without it undesirably increasing the height of the capacitor. Accordingly, the structure as illustrated in FIG. 31 or in FIG. 37 wherein, the feedthrough capacitor overhangs the ferrule is very important, such that the 500 k dielectric can be used thereby minimizing the capacitor's equivalent series resistance and allowing it to divert a very large amount of MRI energy that's coupled onto implanted leads while keeping the pocket temperature rise to a very minimum. What is the pocket? This is the area where the AIMD is inserted under the skin or muscle of a patient into which implanted leads are attached. The FDA is very concerned that not too much AIMD housing heating 116 occur in the pocket area. Excessive heating can lead to tissue necrosis and even potentially muscle and nerve damage. Accordingly, it's desirable to keep the pocket heating to 4 degrees or less. By minimizing the feedthrough capacitor's ESR, the temperature rise in the area of the AIMD housing is greatly reduced. Accordingly, the present invention enables the use of novel designs in accordance with the '558 invention. Referring once again to FIG. 31, one will note that the four leadwires 111 are all in close physical proximity to the gold pocket pads 248, 250. This becomes very important at high frequencies, such that minimal inductance develop across the feedthrough capacitors internal electrode plates. It is only necessary that a portion of these electrode plates be close to the pad locations 248, 250.

FIG. 32A illustrates an internally grounded feedthrough capacitor 132 exploded away and ready for installation on internally grounded hermetic seal assembly. The hermetic seal assembly, in this case, have 8 active pins (octopolar), 1 telemetry pin and 1 centrally located internal ground lead or pin 111gnd. The ground pin is electrically grounded to the ferrule through a peninsula structure 139. The internal ground lead or pin is either gold brazed or laser welded to this peninsula thereby forming a very low impedance and low resistance connection to the ferrule 112. A gold braze 150 hermetically seals the insulator to the ferrule 112. Gold brazes (not shown) mechanically and hermetically seal the leadwires to the insulator 160. Item T is an RF telemetry pin and must not be filtered since it needs to freely pass high-frequency programming signals from a remote programmer (not described). Accordingly, the hermetic feedthrough assembly of FIG. 32A has 8 active pins that can deliver therapeutic pacing pulses and/or sense biological signals, a telemetry pin, that might also be called an active pin, and a ground pin 111gnd. In FIG. 32B, one will notice that there is no active electrode plate 148a associated with the telemetry pin. Referring once again to FIG. 32A, the feedthrough capacitor 132 is novel and that no ground electrodes are brought to its perimeter or outside diameter surface and accordingly, there is no ground or perimeter metallization 142 at all.

U.S. Pat. No. 5,905,627 describes internally grounded capacitors, the contents of which are incorporated herein fully by reference. Also, describing internally grounded capacitors are U.S. Pat. Nos. 6,529,103 and 6,765,780, the contents of which are also incorporated fully herein by reference.

FIG. 32B shows the feedthrough capacitor 132 of FIG. 32A exploded, such that one can see its active electrode plates 148a and 148h and also its ground electrode plates 146. As shown, any number of these can be interleaved and sandwiched construction to achieve the desired capacitance value.

Figure 32D:
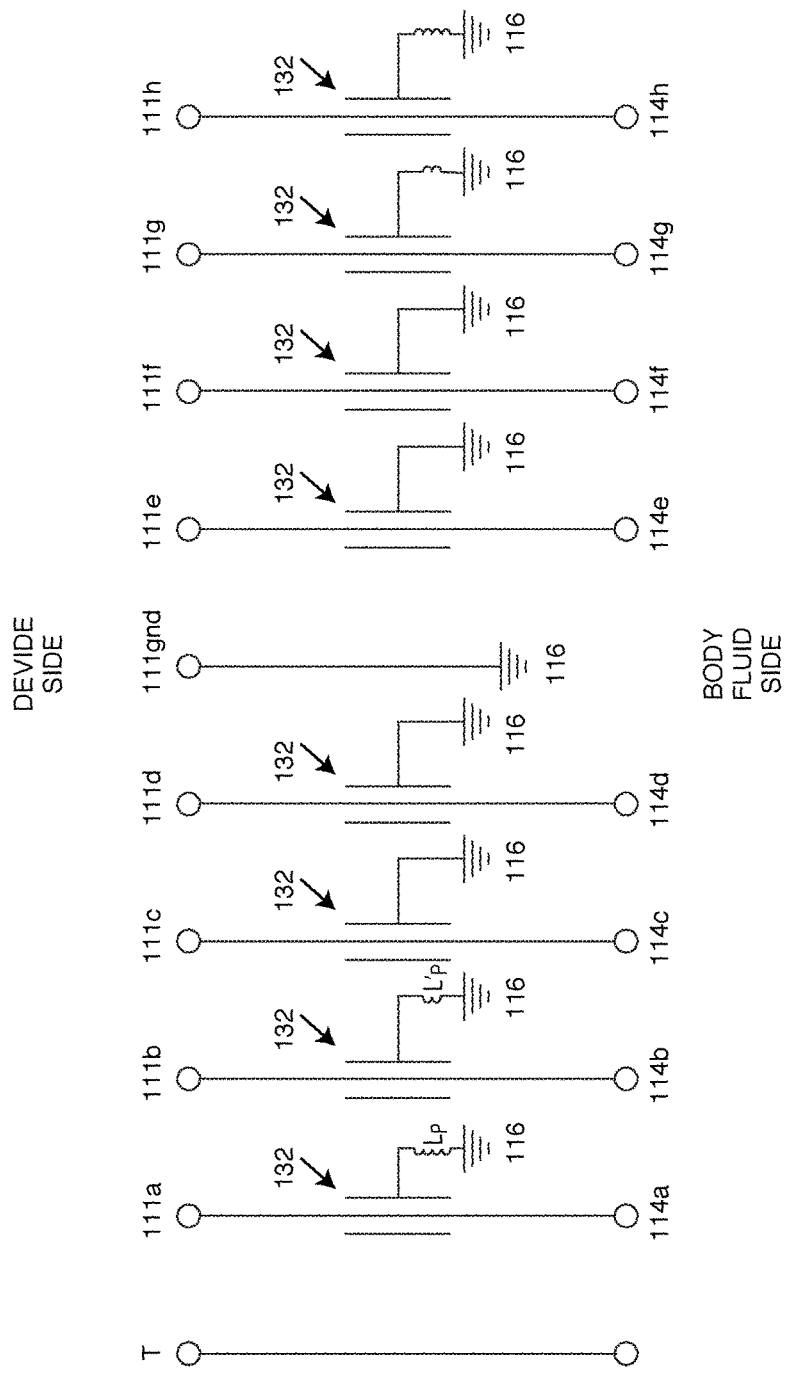
FIG. 32D illustrates that the pins 111c-f that are closest to the ground 111gnd have little to no (insignificant) parasitic inductance.

FIG. 32C shows the feedthrough capacitor 132 of FIG. 32A mounted to the hermetic seal terminal and ferrule 112. Since there is no external metallization on the feedthrough capacitor, there is no electrical connection required for the ferrule 112 at all. Internal ground lead 111gnd is generally of non-oxidized material, such as palladium or platinum or alloys thereof. Accordingly, a very low resistance connection is made from the capacitor ground electrode plate 148 and 146 through ground pin 111gnd and in turn, to ferrule 112. However, referring back to FIGS. 32A through 32C, there is a serious downside. This is because the active pins that are furthest from the ground pins, which would include active pins 148a and 148h are a very long distance away from the single ground 111gnd. Undesirably, inductance builds up across the ground electrode plates 146, such that this inductance undesirably ends up in series with a capacitor's ground electrical path. This parasitic inductance is highly undesirable since inductances at high-frequency will provide a conductive reactance in series with the feedthrough capacitor. This is very much analogous to an undesirable ohmic loss in this area. Schematic diagram, FIG. 32D, illustrates that the pins 111c-f that are closest to the ground 111gnd have little to no (insignificant) parasitic inductance. However, the outer most pins 111a, 111b, 111g and 111h do have this parasitic inductance LP and L'P, which can seriously degrade filter performance. The solution to this problem is attempted as shown in FIGS. 37 through 42 of U.S. Pat. No. 6,765,780, the contents of which are incorporated herein fully by reference.

Figure 33:
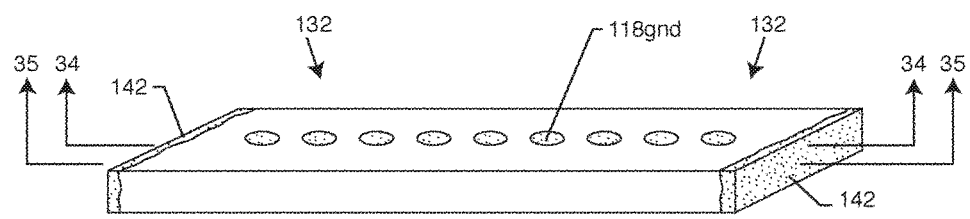
FIG. 33 is an isometric view of the internally grounded and externally grounded feedthrough capacitor taken from FIG. 30A of the '780 patent.
Figure 34:
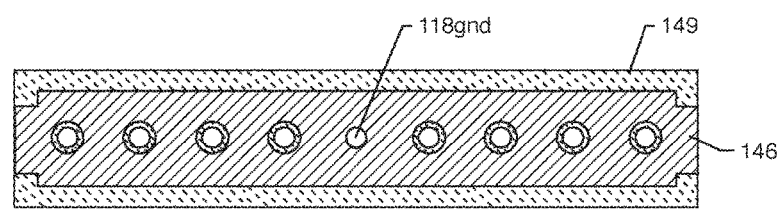
FIG. 34 is taken from section 34-34 from FIG. 33.

FIG. 33 herein is an isometric view of the internally grounded and externally grounded feedthrough capacitor taken from FIG. 30A of the '780 patent. This is best understood by referring to the cross-sectional view shown herein as FIG. 34, which is taken from section 34-34 from FIG. 33. This illustrates the ground electrode plate 146. As one can see, the ground electrode plate 146 is configured such that it will be in electrical contact with ground pin 118gnd. It is also brought out to the short ends (the left and right side of a rectangular feedthrough capacitor), such that a ground metallization 142 can be placed on both ends. The internally and externally grounded feedthrough capacitor, as illustrated in FIGS. 33 through 38 herein, are defined as hybrid internally grounded feedthrough capacitors. The word hybrid comes from the fact that they have an internal ground feedthrough passage as well as external metallizations 142. This multipoint or hybrid grounding system is important, such that each of the active passageways represented by pins 111 in FIGS. 37 and 38, all have a high degree of filter performance (insertion loss). This long and narrow feedthrough capacitor cannot be solely grounded by 118gnd only. This is because the outermost pins or the furthermost pins from 118gnd would have highly degraded insertion loss due to the inductance build up across the internal electrode plates. Accordingly, by also grounding the feedthrough capacitor across its ends, at metallization locations 142, a second and third low inductance path is created. Accordingly, all of the pins of the feedthrough capacitor will offer a high degree of filter performance.

Figure 35:
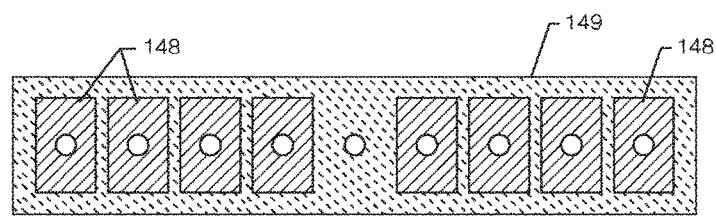
FIG. 35 is taken from section 35-35 from FIG. 33 and illustrates the eight active electrode plates.
Figure 42:
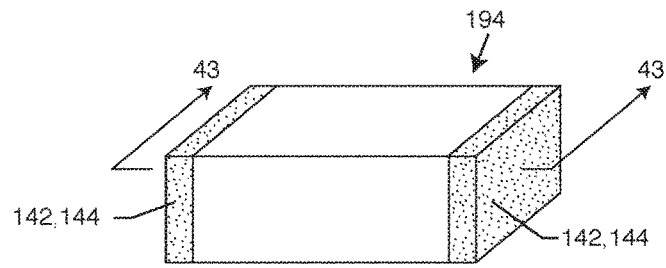
FIG. 42 illustrates an isometric view of a prior art chip capacitor also known as a multilayer ceramic capacitor or MLCC.

FIG. 35 is taken from section 35-35 from FIG. 33 and illustrates the 8 active electrode plates 148. FIG. 42 of the '780 invention shows the capacitor in cross-section with an electrical connection from the capacitor ground metallization 914 to gold braze pad areas 946, which in accordance with that invention, are a continuous part of the hermetic seal between the ferrule and the insulator 924. As previously described, a negative of this construction is that the gold braze 946 will flow due to gravitational forces during high-temperature gold braze furnace operations, when the gold becomes molten or liquid.

Figure 36:
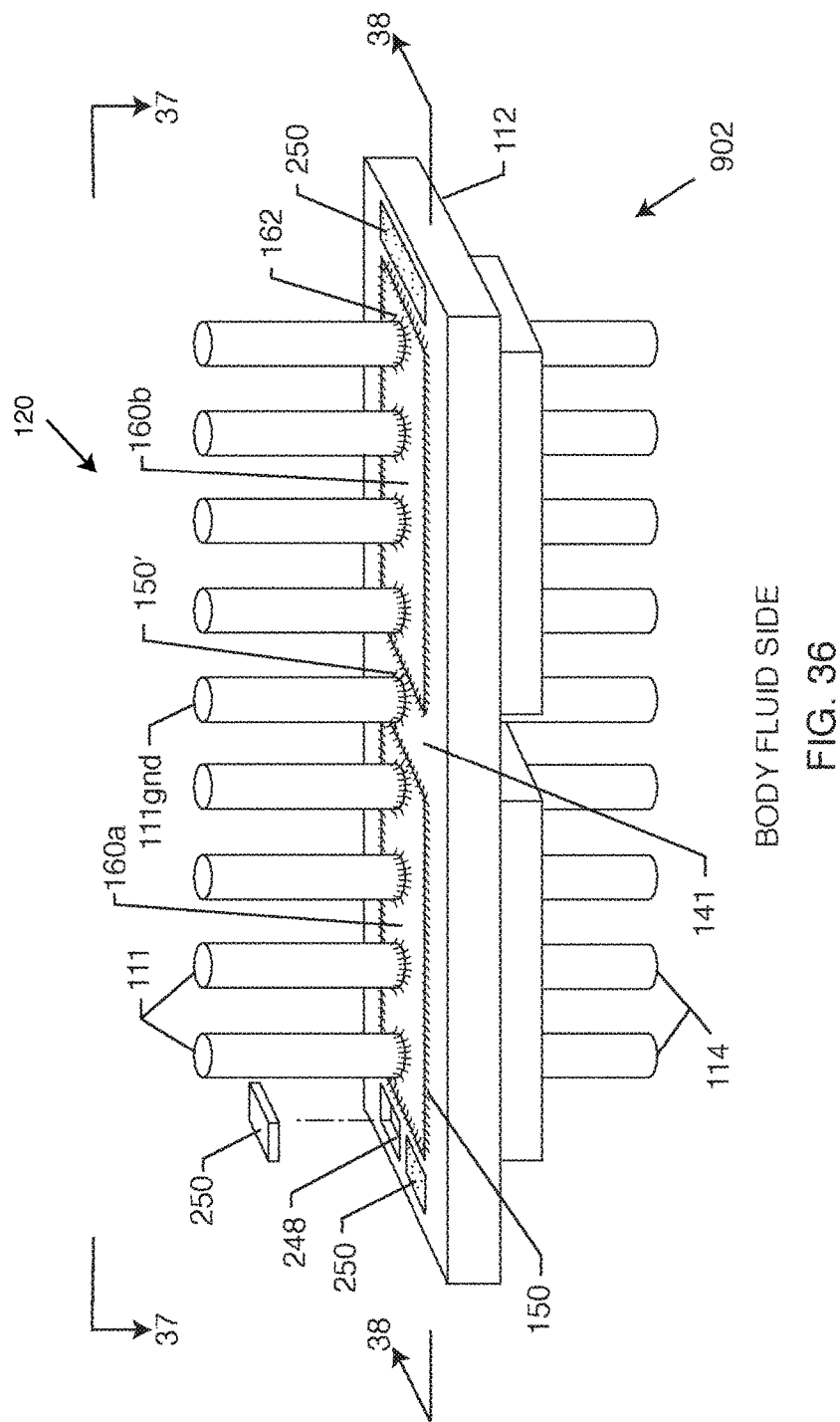
FIG. 36 illustrates the present invention wherein, FIG. 42 of the '780 invention has been modified in accordance with the present invention.

FIG. 36 illustrates the present invention wherein, FIG. 42 of the '780 invention has been modified in accordance with the present invention. That is, there are one or more pocket areas 248 formed that have solid bottoms and side walls (like a swimming pool) that fully contains the gold preform and contact area 250. As illustrated on the left side of FIG. 36, these pockets 248 can be discontinuous or as shown on the right side, they can be joined together and continuous. The resulting broadband and high-frequency performance of such an arrangement overcomes any problems with the previously described parasitic inductances. In other words, it is now assured that every one of the pins has proper high-frequency and broadband and filter performance (attenuation or insertion loss).

Figure 37:
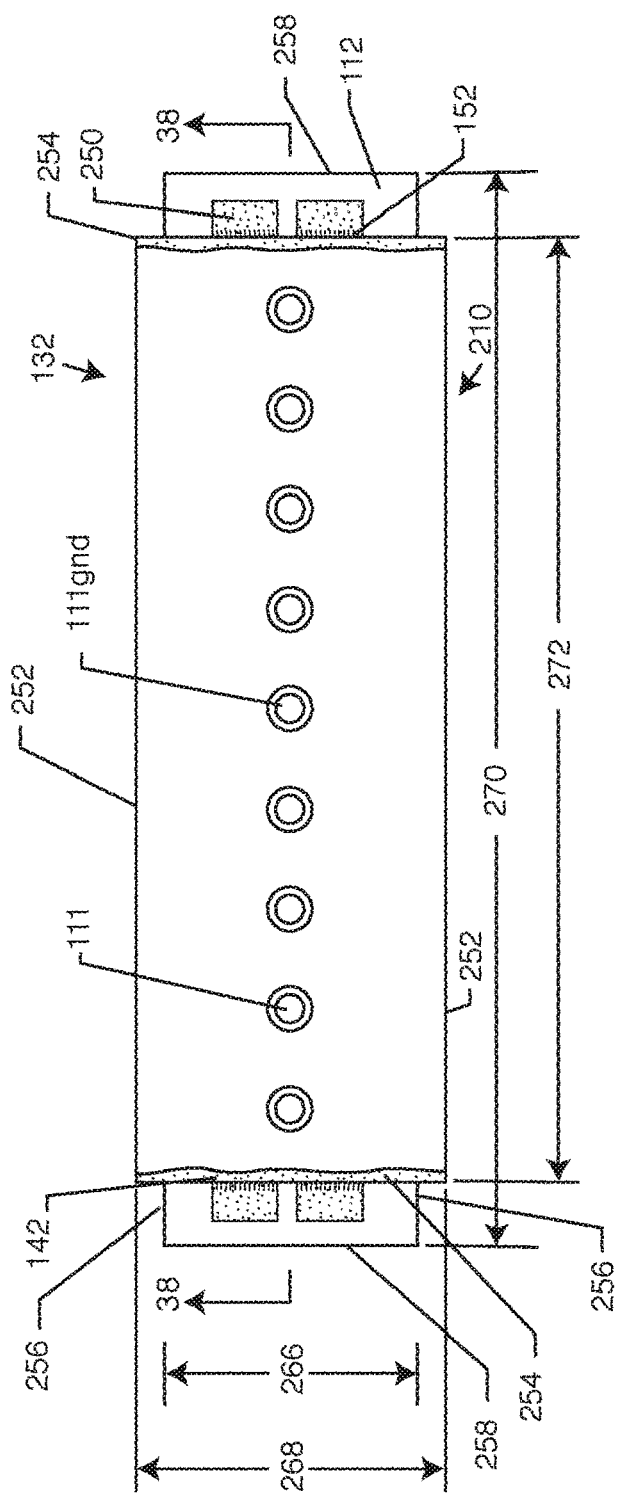
FIG. 37 illustrates the feedthrough capacitor of FIG. 33 mounted onto the hermetic terminal of FIG. 36, except that in this case, the rectangular feedthrough capacitor is wider than the ferrule.

FIG. 37 illustrates the feedthrough capacitor of FIG. 33 mounted onto the hermetic terminal of FIG. 36, except that in this case, the rectangular feedthrough capacitor is wider 268 than the ferrule 266. As previously described, this greatly improves volumetric efficiency. Referring back to FIG. 32A, it will be appreciated that one or more telemetry pins could also be added to the structure as illustrated in FIG. 37. In this case, the telemetry pin would not be associated with a capacitor active area. Referring back to FIG. 37, one can see that an advantage of this construction is the capacitor and the ferrule have both been kept relatively long and narrow so they will fit into an AIMD without unduly increasing its thickness. As previously described, this is very important so that the resulting AIMD be thin so that it is comfortable in a patient pocket. It will also be appreciated that instead of the inline pins, as illustrated in FIG. 37, the pins may be staggered, as previously illustrated in FIGS. 32A, 32B and 32C.

Figure 38:
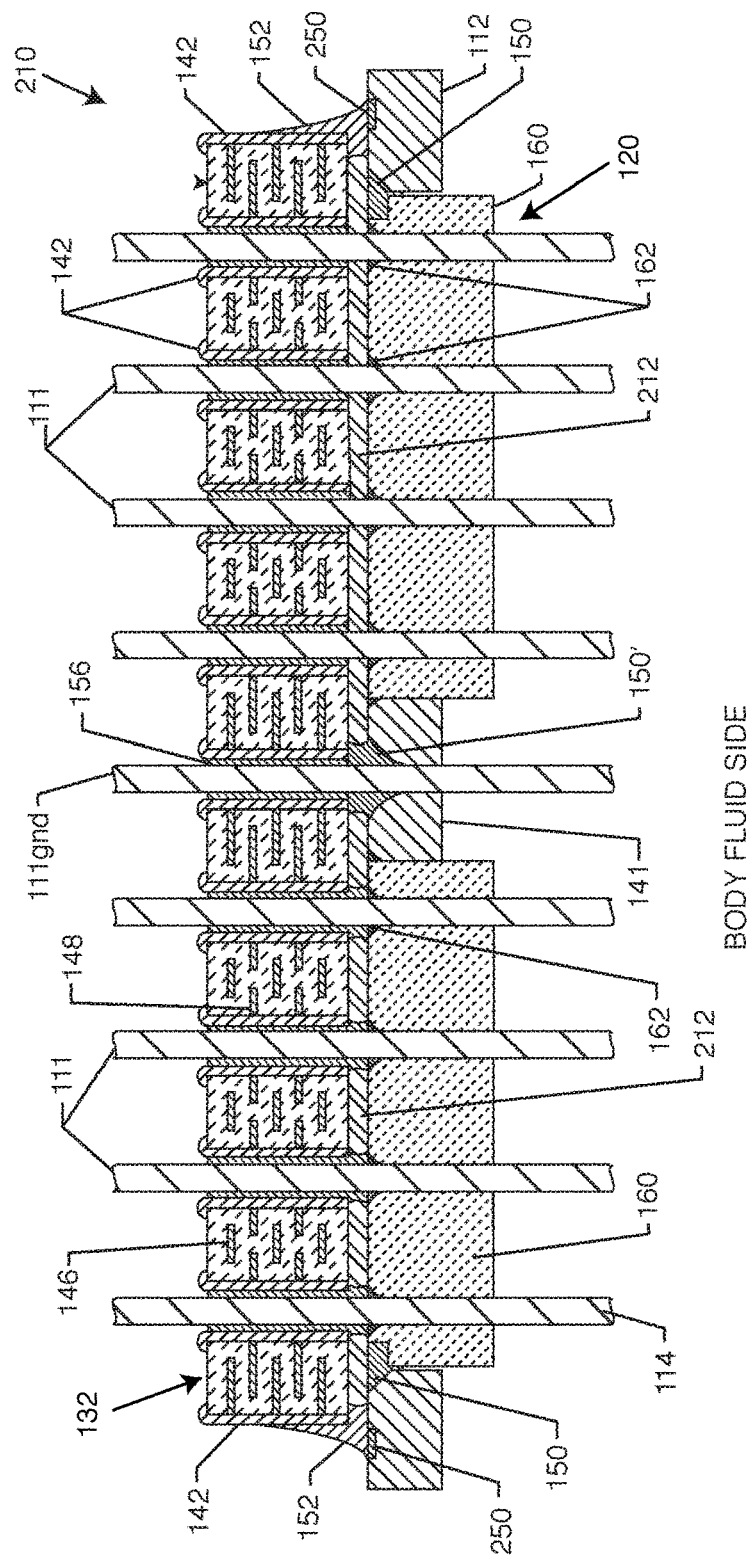
FIG. 38 is a sectional view taken from section 38-38 from FIG. 37.

FIG. 38 is a sectional view taken from section 38-38 from FIG. 37. The capacitor internal ground pin 111gnd is shown electrically connected to the capacitor internal ground metallization through electrical connection material 156. The capacitor ground metallization 142 on the right and the left-hand side, is shown electrically connected 152 to the novel pocket and gold braze areas 250 of the present invention. As one can appreciate, the end pins are no longer very far from ground and accordingly, do not have too much parasitic inductance. In other words, this hybrid internally grounded filter has greatly improved and reliable high-frequency performance.

Figure 39:
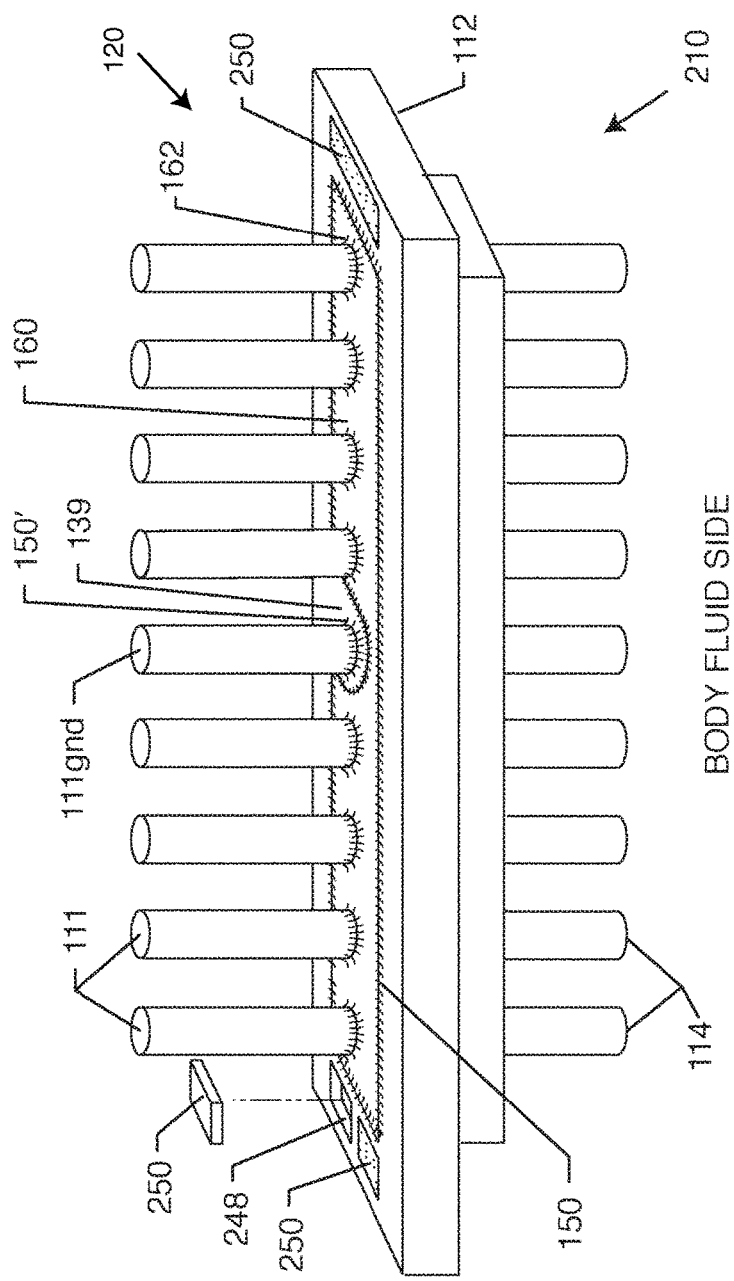
FIG. 39 is nearly identical to FIG. 36, except that the ground pin is part of a ferrule peninsula.

FIG. 39 is nearly identical to FIG. 36, except that the ground pin 118gnd is part of a ferrule peninsula 139. Another way of looking at this is that the insulators of FIG. 36 consist of two separate insulators 160a and 160b, which are individually gold brazed 150 to the ferrule 112. In contrast, the insulator 160 of FIG. 39 is a single insulator and a single and continuous gold braze 150 mechanically and hermetically connects the insulator 160 to the ferrule 112.

Figure 40:
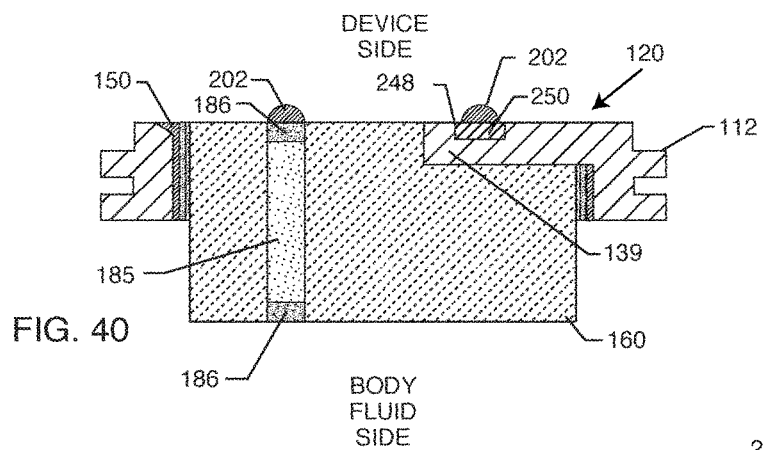
FIG. 40 illustrates a unique hermetic seal subassembly wherein, a passageway through the hermetic seal insulator has been filled with a sintered or co-fired conductive paste.
Figure 47:
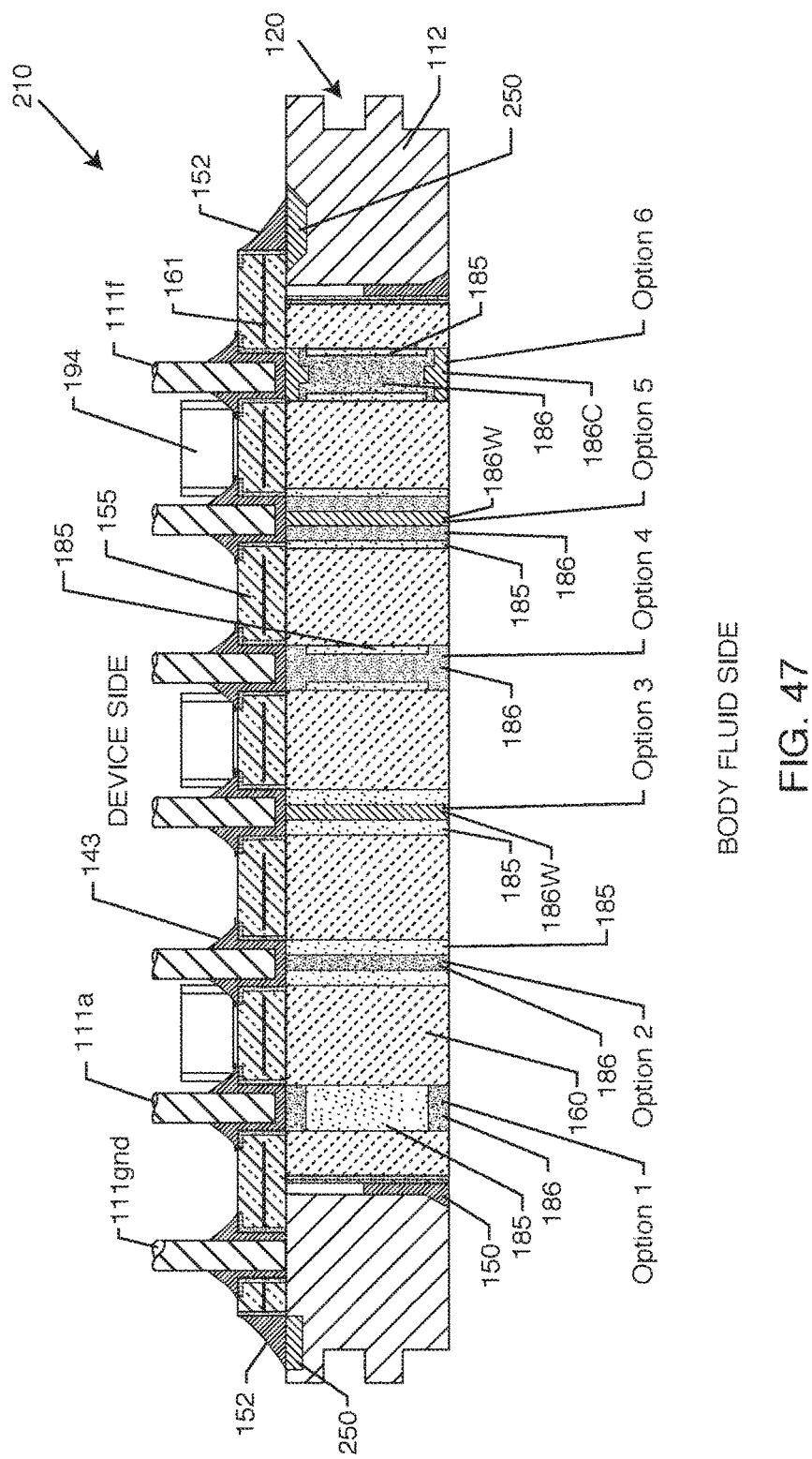
FIG. 47 illustrates a hermetic seal subassembly with various types of co-sintered and filled vias.

FIG. 40 illustrates a unique hermetic seal subassembly wherein, a passageway through the hermetic seal insulator 160 has been filled with a sintered or co-fired conductive paste. In the embodiment of FIG. 40 as illustrated, item 185 would comprise a CERMET or a CRMC (ceramic reinforced metal composite). The two end caps 186 would be of substantially pure platinum. However, there are many options and variations on this. It will be appreciated that the present invention applies to any type of filled passageway or via through an insulator that is co-sintered/co-fired. For example, the contents of patent application Ser. No. 15/797,278 are incorporated herein fully be reference. Also incorporated herein by reference are U.S. Pat. Nos. 8,653,384; 8,938,309; 9,233,253; 9,492,659; 9,511,220 and 9,889,306. It will also be appreciated that the present invention is applicable to any of the following U.S. Patents, including U.S. Pat. Nos. 5,333,095; 5,751,539; 5,896,267; 5,973,906; 5,978,204; 6,765,779 and the like, the contents of all of which are incorporated fully herein by reference. Referring now again to FIG. 40, one will appreciate that any of the options or embodiments described in U.S. patent application Ser. No. 15/797,278 can be embodied in a co-sintered filled via. Referring only to the filled via, FIG. 47 illustrates many of these options.

Figure 41:
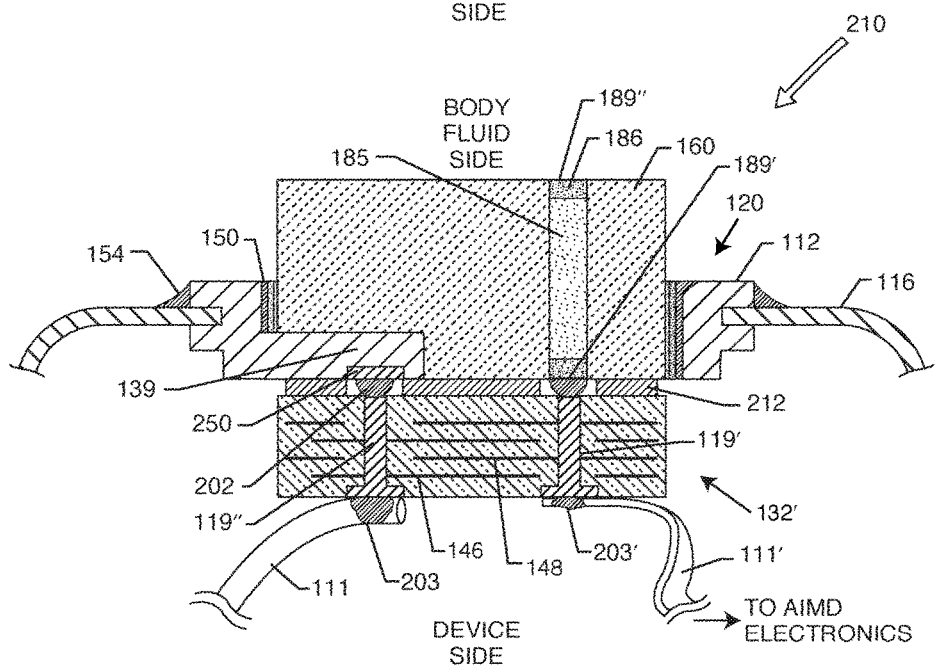
FIG. 41 illustrates an internally grounded feedthrough capacitor mounted to the novel hermetic terminal subassembly of FIG. 40.

FIG. 41 illustrates an internally grounded feedthrough capacitor 132' mounted to the novel hermetic terminal subassembly 120 of FIG. 40. Importantly, the capacitor is internally grounded, which is shown on the left side via hole wherein, the capacitor via hole is electrically connected 202 directly to the gold braze pocket 250, in accordance with the present invention. The gold braze pocket provides an oxide-resistant connection to the peninsula structure 139 of ferrule 112. This ferrule peninsula 139 was previously illustrated, for example, in FIG. 39 herein. The feedthrough capacitor 132 has BGA (ball grid array), solder dot or thermal-setting conductive adhesive dispensed areas 202, as illustrated. The feedthrough capacitor is mounted along with an insulative washer 212 as shown. The insulating washer 212 prevents undesirable migration of the BGA dots 202.

Referring once again to FIG. 41, one will also appreciate that the electrical connection 202 as illustrated, can instead be comprised of an anisotropic conductive film or ACF. ACF films are uniquely applicable to the present invention, particularly where high channel counts are required. Referring once again to FIG. 41, one can see on the device side that a solid filled via 119', 119" in the feedthrough capacitor, allows for a number of unique connection opportunities to AIMD electronics. For example, a ribbon lead 111' can be laser welded, brazed, thermal sonic, ultrasonic bonded or otherwise, welded to the solid filled via, which in this case has a nail head shape 119', 119". On the left-hand side is shown a round device side leadwire 111, which can be attached by any of the aforementioned methods, but also including soldering, thermal-setting conductive adhesives 203 and the like. It will also be appreciated that on the device side, a flex cable or circuit board may be mounted by this technique or more importantly, by use of ACF films.

Referring once again to FIG. 41, if one were to replace the insulating layer 212 and the conductive BGA dots 202 with an anisotropic conductive film, one would encounter the problem that neither of the conducting areas of the mating surfaces are proud. Even though ACF films could be used, in this case, it will be shown in subsequent drawings that having at least one of the conductive surfaces proud will enable the ACF conductive particles, in the contact area, to be desirably flattened (e.g. become spring-like) while at the same time, conductive particles embedded in the ACF film that are not disposed in the proud area, will remain round and surrounded by insulative material.

Figure 41A:
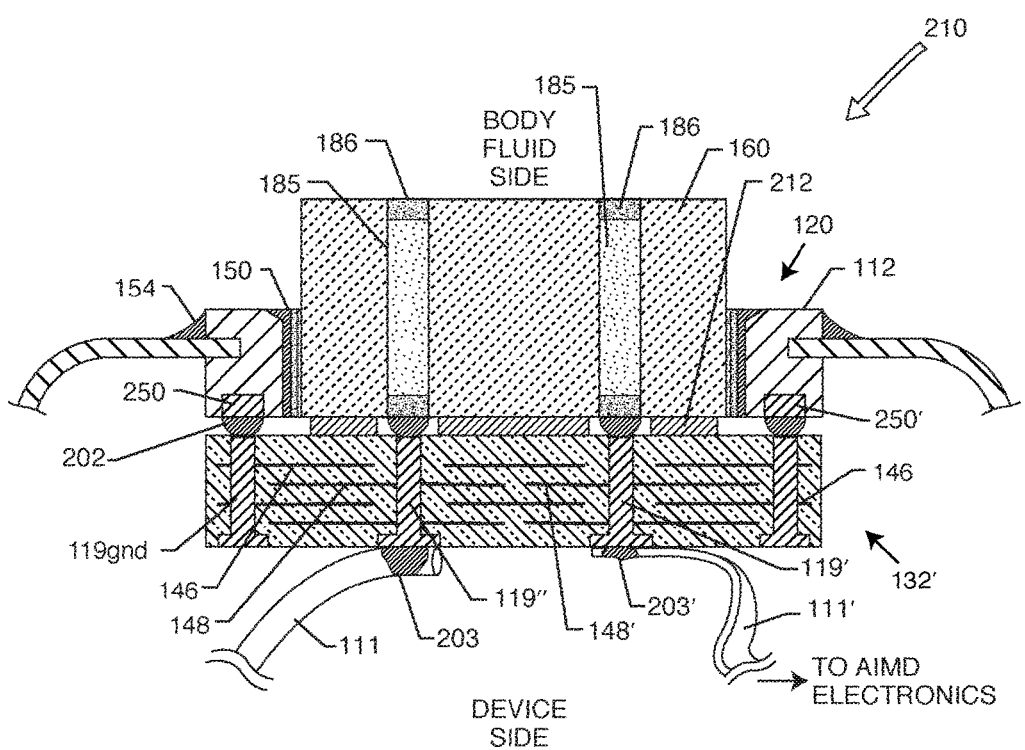
FIG. 41A illustrates an internally grounded feedthrough capacitor having an increased size that is connected at multiple locations to the ferrule using the gold filled pocket of the present invention.

FIG. 41A illustrates an embodiment of the internally grounded feedthrough capacitor 132', previously described in FIG. 41. In the cross section of the embodiment illustrated in FIG. 41A, the capacitor is shown to be significantly wider. The capacitor, in this case, is as wide as the adjacent ferrule 112. Referring once again to FIG. 41A, one will see that only two gold pocket pad areas 250 and 250' in accordance with the present invention. The two gold pocket pads 250 and 250' allow multipoint grounding of the capacitor's internal ground electrode plates 146. It will be appreciated that for long and rectangular capacitors there could be one, two or even a plurality of gold pocket pads 250, 250' . . . 250n provided in the ferrule. It will also be appreciated that the internally grounded feedthrough capacitor 132', as illustrated in FIG. 41A, could also overhang the ferrule 112, as previously discussed.

Referring once again to FIGS. 41 and 41A, one will see that the capacitor feedthrough holes, otherwise known as passageways or feedthrough capacitor via holes, are solid filled 119gnd, 119' or 119". The solid filled feedthrough capacitor vias 119' and 119" and the ground feedthrough capacitor passageways 119gnd are shown as having a solid conductive fill. Capacitor passages 119 and 119gnd may first be terminated 144, as previously described. Or, in many cases, the solid fill may make contact to either the active or ground electrode plates without a termination 144. In other words, a direct connection to the electrode. One is referred to U.S. Pat. No. 8,179,658, the contents of which are incorporated herein fully by reference.

Referring once again to FIG. 41A, one will appreciate that the internally grounded feedthrough capacitor 132' is disposed to the device side of the hermetic terminal. It, therefore, does not need to be biocompatible, non-toxic or even biostable. Accordingly, a number of different materials can be used for the solid conductive fill 119, 119gnd. This includes an entire family of thermal-setting conductive adhesives, such as conductive epoxies or conductive polyimides, a solder fill, a copper fill or any type of conductive metal paste. It is important that the fill material be highly conductive, particularly in the case for an active implantable medical device known as an implantable cardioverter defibrillator. A cardioverter defibrillator or ICD must conduct very high current pulses to the heart in order to properly cardiovert it and restore sinus rhythm. Accordingly, the resistivity or resistance of the via hole from top to bottom, for an ICD application, must not exceed on the order of about 2 milliohms. On the other hand, for typical low voltage applications, such as a cardiac pacemaker, the resistivity of the passageways could be as high as 8 to 10 milliohms. For a neurostimulator applications, for example, a retinal implant, which requires extremely low currents, the resistivity of the filled vias 119, 119gnd could be on the order of 10 to 100 milliohms. Alternatives to conductive BGA 202 attach include but are not limited to: electronic conductive adhesives, anisotropic-conductive film, anisotropic-conductive paste, conductive epoxy, conductive silicone, traditional soldering methods, and other compatible approaches.

Figure 41B:
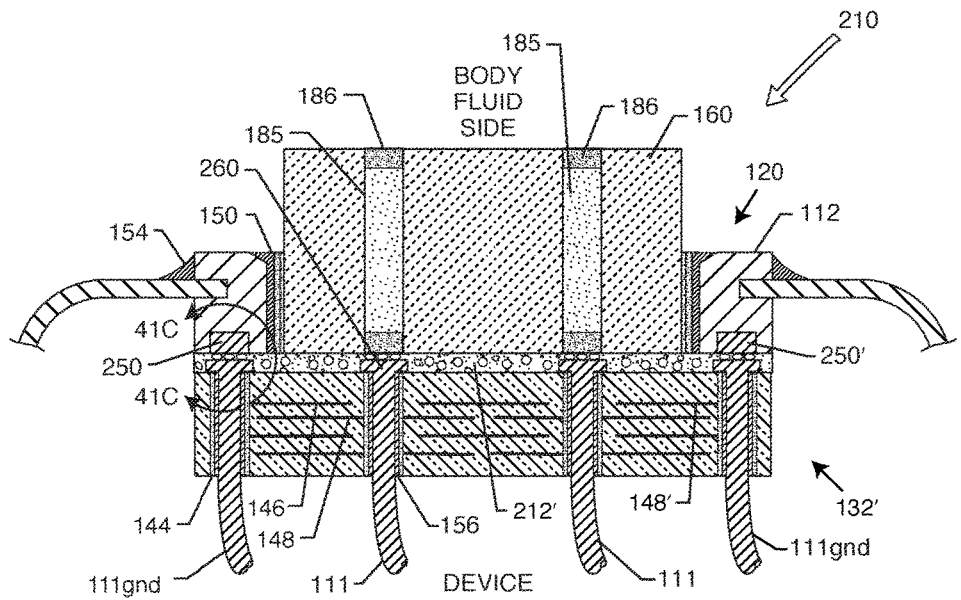
FIG. 41B is similar to FIG. 41A now showing an anisotropic conductive film for making electrical connection to the gold filled pocket of the present invention.

For example, referring once again to FIGS. 41 and 41A and looking forward to FIG. 41B, if one were to replace the insulating layer 212 and the conductive BGA dots 202 with an anisotropic conductive film (ACF, 212'), one could encounter attachment difficulty in that neither of the conducting areas of the mating surfaces are proud. Although ACFs could be used in this case, it will be shown in the following drawings, that having at least one of the conductive surfaces proud (protruding above the surface) will enable, in this case, compressible conductive particles embedded in the ACF to be desirably compressed (thereby behaving spring-like) in the electrical contact area, while at the same time, allowing the rest of the conductive particles embedded in the ACF that are not disposed in the proud area to remain uncompressed and therefore, retain roundness while surrounded by the insulative material. In this, this is how this specific ACF works: in the areas where the conductive particles 202' in the ACF are compressed, conduction occurs in the Z-axis. At the same time, where particles 262 are not compressed, they remain insulative thereby providing a high degree of insulation resistance between adjacent passageways between mating surfaces, such as but not limited to a hermetic feedthrough and a feedthrough capacitor or a hermetic feedthrough and a filter circuit board assembly. Compressibility in this example of the conductive particles embedded in the ACF offers two big advantages: (1) a compressible particle acts like a spring wherein a stress imparted on the particle embedded in the ACF results in extension of the particle, changing the shape of that particle from, for example, a sphere into an elongated ellipsoid; and (2) the contact resistance of the compressed particle is lower because the compressed particle has a bigger surface in contact with its mating surface. The inventors know of no prior art or case where a feedthrough capacitor for an active implantable medical device has been mounted to adjacent co-sintered passageways of a hermetic seal using ACF films. One major reason for this is the use of co-sintered passageways in the hermetic seal insulator 160 is relatively new. Most of the prior art has incorporated through leadwires, as shown in the prior art herein. As will be further illustrated, a novel modification of the structure of FIG. 41A, which will include proud mating surfaces, is a novel feature, which will enable the reliable use of ACF films.

FIG. 41B is a modification of FIG. 41A and, in this embodiment, the feedthrough capacitor passageways or via holes are metallized 144, as previously described for prior art feedthrough capacitors, a novel nail-headed 260' or co-formed low cost leadwire 111 or 111gnd is provided, and the insulating layer 212 is replaced with an ACF 212' wherein the medium in which the conductive spheres are embedded is of an insulative or non-conductive material. The co-forming of the leadwire 111 and 111gnd, results in a nail head shape (260) as illustrated. Manufacturing the capacitor subassembly is very easy. First, one manufactures the feedthrough capacitor 132' and then applies the passageway metallization 144. It will be appreciated that this passageway metallization 144 could be applied using a variety of methods, including various plating operations, application of silver or palladium silver glass frits, sputtering and the like. After the feedthrough capacitor 132' has been manufactured, then the nail-head leadwires 111 and 111gnd are inserted. A solder pre-form could first be slipped onto the nail-headed leadwire and then the leadwire could be inserted through the feedthrough capacitor passageway. At this point, the feedthrough capacitor with the nail-headed leadwires oriented downward for gravitational purpose, would be placed on a fixture, which would allow it to pass through a tunnel soldering oven or onto a flat fixture, which could be soldered using batch oven processes. At this point, the solder pre-form melts thereby forming both a mechanical and electrical connection from the leadwire and its contiguous nail-head structure and the inside diameter metallization 144 of the feedthrough capacitor. The solder 156 is reflowed, thereby making an electrical connection to leadwires 111 or 111gnd and the capacitor metallization 144. This attachment also serves as an electrical connection by way of the capacitor metallization 144, which is in turn, electrically connected to the capacitor's internal active 148 or ground electrode plates 146. It is significant that in this embodiment, the nail head is positioned at least partially proud of the capacitor surface, meaning that the nail head 260, to some extent, sticks up or protrudes above the surface of the feedthrough capacitor. Having the nail head proud of the feedthrough capacitor surface facilitates crucial mating between the feedthrough capacitor and the ground gold pocket pads 250, 250' and the feedthrough capacitor 132' and the conductive sintered vias 185, 186 that pass through the insulator structure 160. An ACF wherein the medium in which conductive spheres are disposed is insulative is used in place of the insulator 212 shown in FIGS. 41 and 41A. These conductive spheres 262 may be rigid, such as gold-plated nickel spheres or they may be gold-plated polymer spheres, which may be readily deformed during pressure and curing operations. In the present application, since the sintered alumina 160 and the sintered platinum caps 186 are relatively rigid, it may be desirable for the spheres that are embedded in the ACF to be capable of deforming, such as would a sphere made using a conductive polymer. One typical way to make these conductive spheres is to gold plate a polymer that is readily compressible. As previously stated, compressibility offers the advantage that the sphere behaves like a spring wherein the sphere or spheres embedded within the adhesive deforms under compression thereby changing shape into more of an ellipsoid 262' and thereby lowers electrical contact resistance. The combination of the proud nail head and an ACF comprising compressible spheres 262 assures a highly conductive and reliable mating surface between the two conductive surfaces to be joined.

Figure 41C:
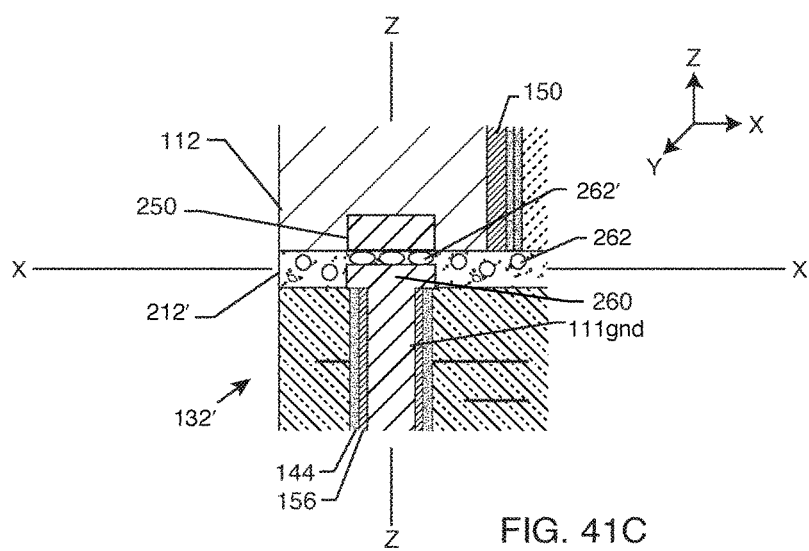
FIG. 41C is an enlarged view of the section 41C-41C taken from FIG. 41B.

Referring once again to FIG. 41B, the importance of the nail head structure 260 becomes readily apparent. This is best understood by referring to FIG. 41C. which is taken from section 41C-41C from FIG. 41B. One can see that in FIG. 41C, the ACF 212' has been compressed and then cured at an elevated temperature. The conductive spheres 262, which are randomly located in the ACF, remain round, except in the area where the proud conductive nail head 260 is located. In the area wherein the nail head is proud, the spheres 262' that are aligned in the region of the proud nail head become compressed and are changed from round spheres to ellipsoid shapes; and they remain compressed until the curing operation is completed. Notably, the conductive spheres 262 that are not in a proud nail head area do not compress and remain round. This is very important as the spacing between the uncompressed round conductive spheres is preserved so that the insulation resistance in the X and Y axes remains as designed and is not compromised. In other words, one achieves the conductivity desired in the Z-direction while minimizing any risk of developing a short circuit between any of the spheres in the XY plane. Accordingly, the use of an ACF only allows electrical contact and conduction in the Z-direction where the proud surfaces 260 occur. Moreover, no alignment of the ACF is required to achieve the desired Z-axis conductivity. It is important, however, that the nail head proud structures 260 be sufficiently aligned with either the gold pocket pad dots 250 or the sintered conductive vias of the insulator 185, 186, as shown. It will be appreciated that process controls are required, and that the ACF selected have the correct thickness, particle 262 sizes, number and distribution, including proper height and volume, to adequately allow proper conductivity between the proud nail-head structure 260 and its mating surface, which comprises at least one conductive passageway through the alumina insulator of the AIMD hermetic terminal subassembly.

Referring once again to FIG. 41C, one will appreciate that the conductive spheres 262 could comprise a solid nickel sphere that is also then plated by gold to make it highly conductive. As previously stated, rigid conductive spheres 262 will not deform during compression of the proud surface 260 against the gold pocket pad area 250 or the sintered vias 185, 186 of insulator 160. Some degree of deformation may be desirable, hence an embodiment having conductive spheres 262 comprising a core material that is compressible. Referring once again to FIG. 41C, one will appreciate that the gold pocket pads of the present invention 250, generally comprise a highly pure gold, such as 99% pure gold or greater. Interestingly, pure golds are not used in the jewelry industry because they are too soft and too yellow. Bright golds are shinier and have a greater hardness. This becomes a great advantage of the present invention by using pure gold as it is highly resistant to oxidation. Importantly, highly pure golds are relatively soft and malleable. Accordingly, the use of rigid conductive particles 262 and the ACF film (that will not deform under compression and curing) can be useful in that, they will be pressed into the relatively soft gold surface and create a relatively large and highly electrically conductive mating surface area. Compressible materials may be polymers, composites, meshes, screens, braids, foamed materials, custom fiber or wire forms, pressed powders, pressed material clumps, either as formed or infiltrated with either an elastomeric, semi-rigid or rigid material prior to coating. These balls or conductive spheres 262 would typically be spheres (round), but could also comprise any type of cross-section, including elliptical, elongated, rectangular, triangular, square, cubic, trapezoidal, tabular, irregular, dendritic, flake, platelet, fiber, tubular, angular, symmetric, and asymmetric. They may all be the same or multimodal. Typically, when the conductive spheres 262 comprise a compressible core, it is appreciated that at least one outer layer may be applied. In the case of more than one outer layer, each layer may have specific physical and chemical properties commensurate with the application. The layers may be applied by plating, coating, dipping, sputtering and similarly applied methods. For example, in applications requiring high levels of conductivity as would be required for pulsing therapy delivery, a first plated layer of nickel may be applied and then a second layer of gold may be applied to achieve the level of conductivity necessary to sustain the pulse. In certain applications wherein current carrying capabilities are low (such as in most neurostimulators), the nickel layer could be omitted. In applications where biocompatibility is a requirement, gold or other highly conductive biocompatible materials, such as platinum or palladium, may be used.

Referring once again to FIG. 41B, it will also be appreciated that the use of ACF need not be combined with the gold pocket pads 250 of the present invention. In other words, the ACF principles of use, as disclosed herein, could be applied to any of the following U.S. patent application Ser. Nos. including: Ser. Nos. 15/797,278; 15/863,194; 15/603,521; 15/844,683, and U.S. provisional application Ser. No. 62/420,164; the contents of all of which are incorporated herein fully by reference. The ACF principles of use are also fully applicable to U.S. Pat. No. 9,511,220; U.S. patent application Ser. No. 13/742,781, now U.S. Pat. No. 8,938,309; U.S. provisional application Ser. Nos. 61/587,029; 61/587,287 and 61/587,373, the contents of all of which are also fully incorporated herein by reference. It will also be appreciated that the methods taught herein as to how to incorporate ACFs for attachment to a feedthrough capacitor to a hermetic terminal subassembly having co-sintered vias would also be applicable to U.S. Pat. Nos. 5,782,891: 5,855,995, 6,660,116; 9,610,452; and 8,494,635, the contents of all of which are also or additional incorporated herein by reference.

FIG. 42 illustrates an isometric view of a prior art chip capacitor also known as a multilayer ceramic capacitor or MLCC. As shown, the capacitor 194 comprises a dielectric body with metallizations 142, 144 on either end. The reason the active metallization 142 and the ground metallization 144 are shown disposed on either side is that there is no polarity to such a capacitor and it can be reversed. In other words, grounding only occurs when one side of the MLCC chip capacitor is connected to a ferrule 112. It is understood from reading this disclosure that the present invention may be utilized with the use of different types of capacitors, including types mounted on circuit boards, including but not limited to chip capacitors, MLCC, stacked film capacitors or tantalum chip capacitors.

Figure 43:
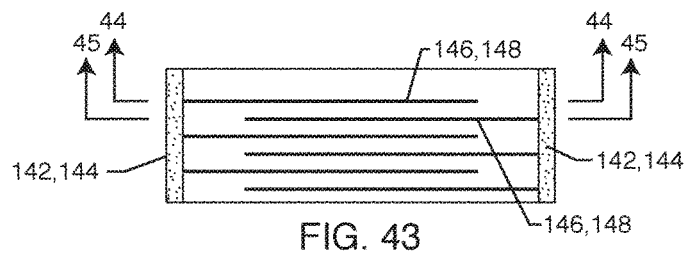
FIG. 43 is a sectional view taken from section 43-43 from FIG. 42.

FIG. 43 is a sectional view taken from section 43-43 from FIG. 42. Shown in section are two sets of electrode plates 146, 148. Again, these are numbered as 146, 148 indicating that either one can be active or the other set can be ground. Such capacitors are known as 2-terminal chip capacitors. They are not coaxial and are not effective broadband filters up to very high frequency, such as a 3-terminal feedthrough capacitor. This is because they do have internal inductance and will at some frequency, self-resonate. However, when they are disposed physically very close to the point of leadwire ingress into an AIMD housing, they can still be effective EMI filters.

Figure 44:
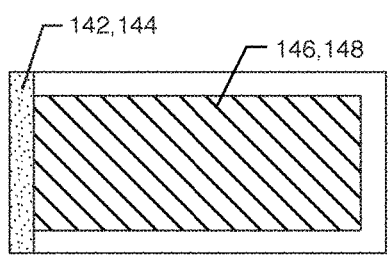
FIG. 44 is taken from section 44-44 from FIG. 43.
Figure 45:
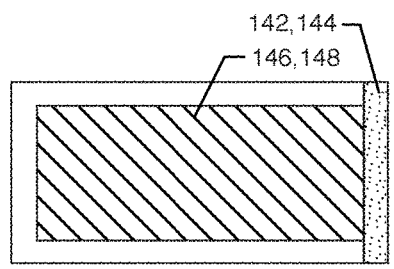
FIG. 45 is taken from section 45-45 from FIG. 43.

FIGS. 44 and 45 are taken from sections 44-44 and 45-45 from FIG. 43. These illustrate the right and left-hand electrode plate sets of the MLCC or chip capacitor 194. The overlap of these two electrode areas form what is known as the effective capacitance area or ECA.

Figure 46:
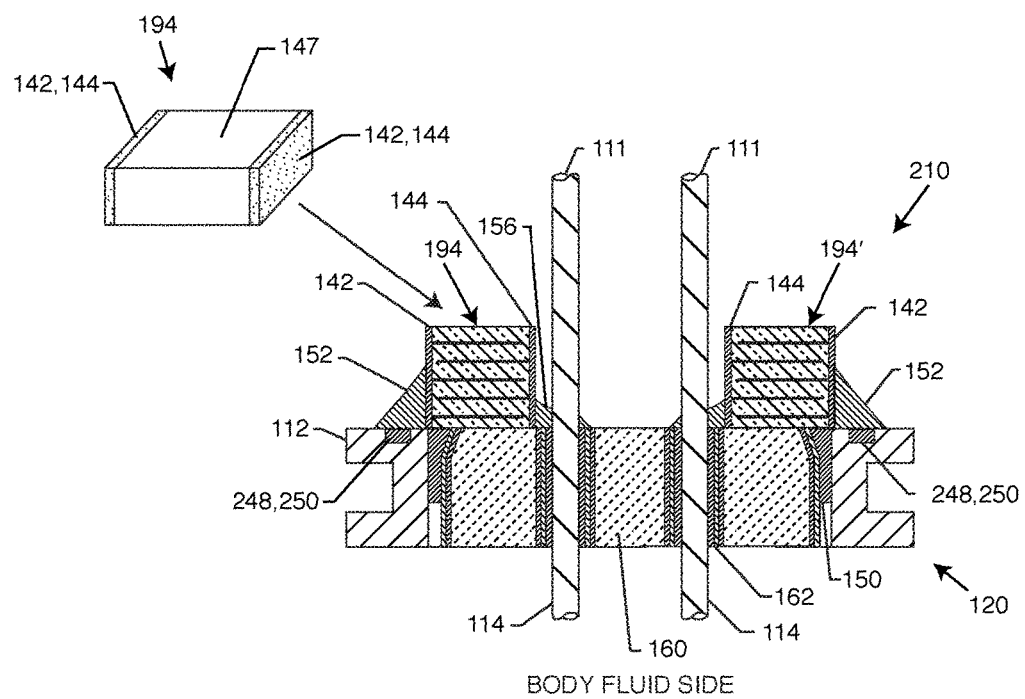
FIG. 46 shows the chip capacitor or MLCC capacitor of FIG. 42 mounted and installed directly on top of a hermetic seal feedthrough assembly.

FIG. 46 shows the chip capacitor or MLCC capacitor 194 of FIG. 42 mounted and installed directly on top of a hermetic seal feedthrough assembly as has been previously described. As can be seen in the cross-section, the left-hand termination of the left-hand chip capacitor is designated as 142 since it is electrically connected 152 to the ferrule 112. Importantly, in accordance with the present invention, the electrical connection material 152 at least partially makes electrical and physical contact to the gold braze 250, which is contained in the novel pocket area 248. There is a second chip capacitor associated with the other feedthrough leadwire (bipolar) shown on the right-hand side of the cross-section of FIG. 46. As shown, its ground electrical connection 152 is also attached from its ground metallization 142 to gold braze area 250.

FIG. 47 illustrates a hermetic seal subassembly with various types of co-sintered and filled vias, which are more thoroughly described in U.S. patent application Ser. No. 15/797,278. Referring once again to FIG. 47, one can see that there is a circuit board 155 that is disposed on the device side of the hermetic seal insulator. The circuit board has at least one internal ground plate 161, as illustrated. It will be appreciated that the circuit board may have a number of internal ground plates or even an external ground plate. Various types of circuit boards and grounding techniques are more thoroughly described in U.S. Pat. No. 8,195,295, the contents of which are incorporated herein fully be reference. In accordance with the present invention, the circuit board internal ground plate 161 is grounded to the ferrule 112 through the novel pocket pads 250 of the present invention. It will be appreciated that a combination of external and internal ground plates may be embodied in the circuit board 147. The circuit board has a number of MLCC capacitors 194 that have their active termination attached to one of the respective active leadwires 111 and their ground sides attached through via holes (not shown) to the at least one ground plate 161. It will also appreciated that on the top of the circuit board, there could be active circuit traces between the active side of the MLCC chip capacitors and the ground pins 111 or alternatively, the capacitor active metallization could be butted up or aligned adjacent to the various active leads 111 along with an electrical connection. Various options for the co-sintered conductive fill are shown in the insulator 160 passageways in accordance with the Ser. No. 15/797,278 application. On the left, Option 1 is illustrated, which was previously described in FIG. 40 herein. Option 2 illustrates a co-fired via with a substantially pure platinum inner core 186 surrounded by the ceramic reinforced metal composite 185. Option 3 illustrates a solid metallic structure, such as a platinum leadwire 186W, which is co-sintered with a CRMC material 185. Option 4 is very similar to Option 2, except that both the device side and the body fluid side have been counter-bored to provide a larger contact area to the substantially pure platinum 186. It will be appreciated that the counter-bore could appear on the device side, the body fluid side or both, as illustrated. Option 5 illustrates a metallic or substantially solid core 186W, which could comprise of platinum leadwire surrounded by an area of sintered pure platinum 186, which is also surrounded by a layer of CRMC 185. Now referring back to Option 2, one will also appreciate that the CRMC layer 185 may be graduated. In other words, one may first fill the empty via hole with a CRMC material that has a relatively low metal content, then allowed to dry and then drill it out and fill it again, this time, with a CRMC having a higher metal content. Then after drying that, it is drilled out and the center is filled with a substantially pure platinum 186. The resulting structure is then co-sintered along with the green insulator 160 to form a co-fired composite highly conductive and hermetically sealed via. Again, this is more fully described in pending application Ser. No. 15/797,278. Referring now back to FIG. 47, Option 6 is very similar to Option 4, except that metallic and substantially solid end cap 186C have been co-fired, in this case, to both the device and body fluid sides. This cap 186C would typically be of substantially pure platinum so that it would readily co-fire to the substantially pure platinum paste 186. It will be appreciated that the novel end cap 186 may be disposed on the device side, on the body fluid side or both, as illustrated.

As shown in FIG. 30, the gold braze 250 that is in the pocket 248 is relatively formed and disposed on the same device side as the gold braze 150. To the contrary as shown in FIG. 47, the gold braze 150 is formed mostly from and on the body fluid side whereas the gold braze 250 is still disposed on the device side in the pocket 248. To manufacture these different embodiments, there are unique corresponding methods that are now discussed herein. For example, referring back to FIG. 30 and all of the embodiments of the invention presented herein, the first gold braze 150 may be made at the same time or at a different time in comparison to the melting of the gold preform 250 that is in the pocket 248. Furthermore, the first gold braze 150 may be the same or of a different material composition in comparison to the gold pocket pad preform 250.

Referring once again to FIG. 47, having the first gold braze and a gold pocket pad(s) on opposite sides of the ferrule (device side and body fluid side) may lead to an assembly problem in that, typically, the first gold braze and the gold pocket pad preforms are reflowed at the same time in a gold brazing furnace. The problem arises when the first gold braze 150 is on the opposite side of the ferrule than the gold pocket pad 250, which is attributed to the force of gravity. Creative fixturing is an option if brazing both at the same time are deemed necessary. As used throughout this entire specification, the terms "brazing" or "braze" may mean that the gold pocket pad preform has been melted and metallurgically bonded to the ferrule pocket. For example, braze pocket support features can be designed to hold the first gold braze 150 in place and to guide gold pocket pad preform flow during the single brazing step. Alternatively, multi-stage brazing also provides a viable solution wherein one gold braze (braze preform 150 or pocket pad preform 250) is a conventional high temperature gold braze preform and the other gold braze preform (150 or 250) would be a lower temperature braze preform.

For example, in the case of multi-stage brazing, the first gold braze preform 150 and the gold pocket pad preform 250 could comprise two different materials configured to reflow at different temperatures, wherein the first gold braze preform 150 comprises a higher melting temperature braze material and the gold pocket pad preform 250 comprises a lower melting temperature material. Again, as one skilled in the art will now appreciate, the brazing operations could be flipped such that the gold pocket pad preform 250 is metallurgically melted and fully captured into the pocket 248 and then the first gold braze preform 150 is made at a lower temperature in a second brazing operation. Brazing at two different temperatures allows one braze preform to be disposed on the body fluid side whereas the other pocket pad preform is disposed on the device side.

Multi-stage brazing materials typically include materials with a wide range of melting points. For example, a primary material may be pure gold (99.99%). Subsequent materials may be various biocompatible, lower temperature gold alloys. A preferred gold alloy is one which contains more than 50% gold by weight. Two non-limiting examples for lower temperature, multi-stage biocompatible brazing (<850° C.) include: 82Au-18In (530° C.) and 88Au-12Ge (356° C.). When chosen as the braze of choice for sustained hermeticity, the ductility, oxidation resistance, and wettability of gold and gold alloys of compositions more than 50% gold by weight make these brazes a good choice for creating and sustaining a hermetic seal.

First gold braze preforms 150 or gold pocket pad preforms 250 that are manufactured from nano-gold particles offer yet another alternative for multi-stage brazing. Particle sizes less than about 5 nm allow melting temperatures of 700° C. or less depending on uniformity of size and size distribution. It would be known to one skilled in the art that the smaller the particle size, the lower the melting temperature. It would also be known to one skilled in the art that melting temperatures can be customized based on optimal particle size selection, mixing and preform manufacturing. Notably, if a fine gold wire is the desired start material to form first gold braze rings or gold pocket pad preforms, then melt temperature control is based on wire grain size. The smaller the grain size, the lower the melt temperature. Specifically to pocket pads 248, 250 for filter attach or circuit board attach, in both the nano particle and fine wire cases, one skilled in the art would know alternative oxide-resistant conductive materials are usable. Biocompatible materials would specifically be used in the case of pocket pads designed for body fluid side filter attach.

In cases where the risk of direct body fluid contact is negligible, other first gold braze preform 150 or pocket pad preform alloys 250 can be used. Among the alloys that could be considered are: copper/silver (28/72)—MP 780° C.;

indium/copper/silver (10/27/63)—MP 685-730° C.; gold/nickel (82/18)—MP 950° C.; nickel/gold/copper (3/35/62)—MP 1,000-1,030° C.; gold/nickel/titanium compositions including those disclosed in U.S. Pat. No. 4,938,922, the contents of which are incorporated herein by reference.

The best control of first gold braze preform 150 or pocket pad preform volumes 250 is achieved by using die cut performs. This assures a consistent material volume for all seals or melts in a lot. However, a preform ring can also be made by cutting loops of wire off of a coil wrapped around a mandrel. The preform rings created this way usually need to be gently flattened and squeezed to close any cutting gap. A ceramic body can be joined to the flange or the terminal pin or filled via in a number of ways, including brazing, active metal brazing, ceramic/glass/metal joining, transient liquid phase bonding, or other suitable techniques.

In the case of active metal brazing, the primary braze material may be combined by forging or cladding a small amount of another metal, such as, but not limited to, titanium in order to enhance desired reactivity of the braze. It is known, for example, that the addition of titanium to several braze alloy compositions results in increased reactivity and considerable improvement in wetting behavior with a ceramic material. The ceramic is wet by the formation of an intermetallic interfacial reaction product which can then form a joint with the braze alloy. In active metal brazing, the metal facilitates the bonding mechanism to an unmetallized ceramic surface, thus creating the hermetic seal. Although flow characteristics for these alloys are limited since the addition of the metal may make them non-eutectic, and sometimes they also tend to form joints that are more brittle than traditional sputtered seals, this effect becomes less important as the feedthrough size becomes smaller. Active metal brazing would be appropriate where the size of the feedthrough insulator is too small to allow for traditional metallization.

FIG. 48 is very similar to FIG. 47, except that in this case, an insulator 212 is used in conjunction with BGA dots 202, as illustrated. The BGA dots can be solders, solder paste, thermal-setting conductive adhesives and the like. In this case, the BGA dots are shown as half spheroids, but it will be appreciated that after curing, as illustrated, they would flow to take on the shape to fill the openings in the insulator 212.

Figure 48A:
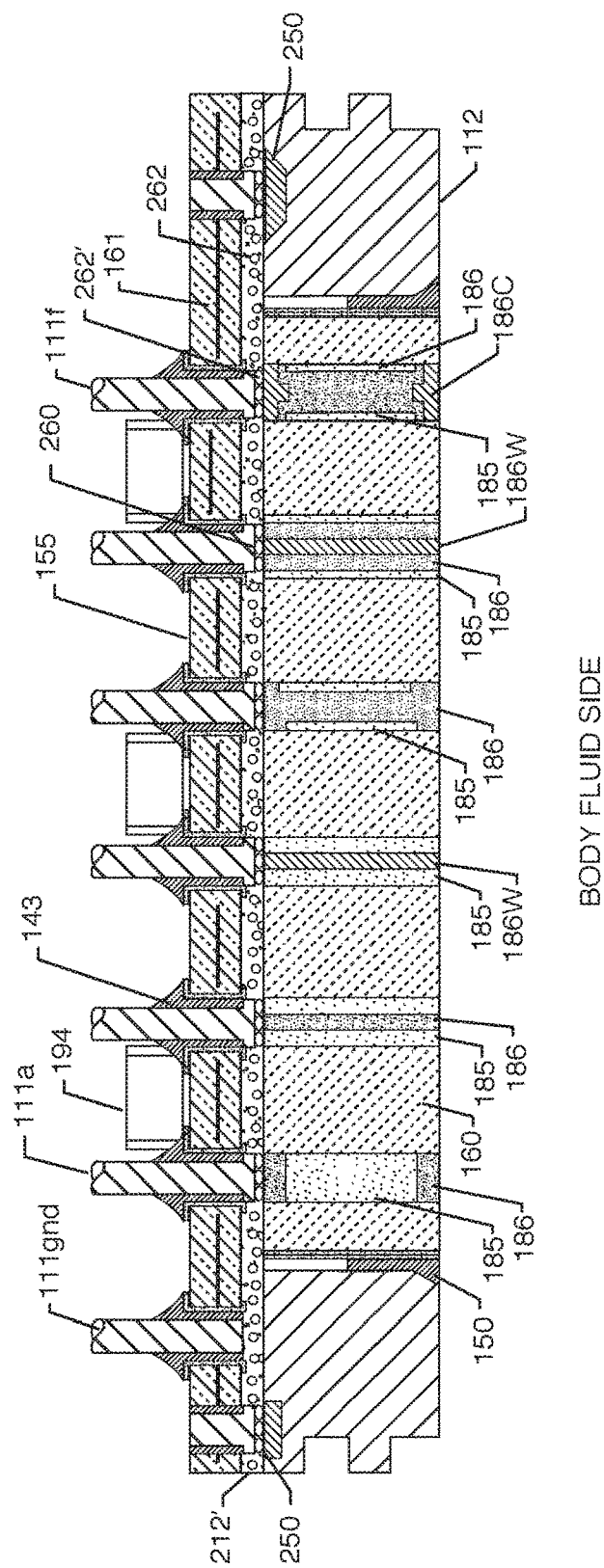
FIG. 48A is similar to FIGS. 47 and 48 now showing an anisotropic conductive film for electrical connection.

FIG. 48A is an adaptation of FIG. 48 wherein an ACF is used as illustrated. In this case, shown are leadwires 111 that are co-formed with novel nail-head structures 260. These nail-head structures stand proud of the bottom surface of the circuit board 155, as illustrated. As previously described, the proud areas facilitate compression of conductive spheres 262' thereby providing highly conductive and highly reliable electrical connection between the co-sintered vias and the nail-head structures 260, which are contiguous and part of leadwires 111. Also shown are two ground pads 250 and 250', as illustrated. These ground pads allow multi-point grounding of the internal electrode plate of the circuit board 161. For convenience, as shown, an additional via hole may be provided in the circuit board for a ground lead 111gnd, which may then be routed to AIMD electronic circuit board (not shown).

FIG. 49 is very similar to FIGS. 47 and 48, except that the wires 111 have been eliminated. Instead, the vias have been filled with electrically conductive material 264, as illustrated. Referring once again to FIG. 49, one can see that the material 264 has been cross-hatched in a different direction than the BGA dots 202. This illustrates that the 264 material is first installed in the vias of the circuit board, which can include a variety of highly conductive fills, including solders, thermal-setting conductive adhesives, conductive inserts and the like. In another embodiment (not shown), the 264 material would be cross-hatched in the same direction as the BGA dots 202 and a solder or thermal-setting conductive adhesive or solder paste would be filled through the via holes thereby effecting the connection in the area of the BGA dots 202 while at the same time, filling the via holes, as illustrated.

FIG. 50 is an adaptation of FIG. 49, such that an anisotropic conductive fill can be used to establish a reliable electrical connection between the circuit board vias and the co-sintered vias of the insulator 160. As one can see, there are via hole inserts 300, which are co-soldered or co-attached to the conductive vias of the circuit board 155. These conductive inserts 300 can be elongated to include a leadwire 111, similarly to that previously illustrated in FIG. 40A or they can be shortened to be short stubs, as illustrated in FIG. 50. In either case, it is important that the inserts comprise a proud nail-head surface 260, such that the conductive spheres 262', in the contact area, are desirably compressed and elongated into elliptical shapes. As previously described, when the conductive spheres are compressible, they become spring-like, which avoids overstressing and fracturing of the mating surfaces and also ensures a long-term and reliable electrical contact.

FIG. 50A is taken from section 50A-50A from FIG. 50 and illustrates a ground gold pad 250 of the present invention. As can be seen, the ACF has round or spheroidal conductive spheres 262, but in the proud area 260, these spheres have been compressed into elliptical shapes 262', as shown. These compressed ellipsoids or oblate spheroidal shapes remain under compression, thereby, through their gold plating (or equivalent), effect a high conductivity connection between the proud insert 300 and bond pad 250. It will be appreciated that the section 50A-50A could also be taken from any of the other conductive areas from FIG. 50. In other words, between the active co-sintered pathways through insulator 160, a similar electrical connection, using ACF and a proud insert shape 300 may also be used. The use of ACFs is particularly indicated for all implantable neurostimulator applications, including spinal cord stimulators, urinary incontinence stimulators, deep brain stimulators, cochlear stimulators, vagus nerve stimulators and the like. The reason for this is that, in general, neurostimulator applications require very low voltages and very low currents. In contrast, the use of ACFs for an implantable defibrillator, which must deliver a very high voltage and very large amount of current, would be more challenging and require more robust compressed spheroids. In the case of an implantable defibrillator, larger mating and proud surface areas may be required. Further, ACFs with conductive compressible cores coated with low resistivity layers may be required. Adjusting conductive particle number, size, and size distribution may further be useful.

Referring once again to FIG. 50, it will be appreciated that the novel insert pads 300 could also be replaced with via hole eyelets, which are well known in the industry. In other words, the via holes could first be metallized by any type of metal plating or metal deposition as shown and then a metallic eyelet, which can be of a compressed shape or a pop rivet construction, could be added. The advantage of the metallic eyelet is that it would stand proud. The eyelets could be filled with solder or could even be solid eyelets on the mating surface between the circuit board and at least one of the insulator 160 and the ferrule 112. The eyelets then would accomplish the same purpose as having a surface standing proud as the nail head of the surface 260.

Referring once again to FIG. 50, one is referred to the right-hand active via hole 264f, which has end caps 186C'. It will be appreciated that the end caps 186C' could stand proud, particularly in the mating area between the circuit board 155 and at least one of the insulator 160 and ferrule 112. With 186C' standing proud, one would have two proud surfaces coming together, i.e. 260 and 186C' thereby more completely assure compression of the conductive spheroid 262' thereby resulting in a highly conductive and very reliable Z-axis electrical connection. It will also be appreciated that by having structural pad 186' standing proud, one could eliminate the necessity to have the opposite surface 260 standing proud. In other words, having the insert pedestal 186C' allows for additional design options to ensure that the spheroids 262 or 262' are properly compressed in the electrical mating surface area. In an embodiment, not illustrated, it will be appreciated that metallic structures could be embedded in a layer of the ACF, thereby eliminating the need for proud surface area 260 or 186C'. In other words, if embedded and parallel metallic discs were embedded in the ACF, that would ensure compression only in that area of the conductive spheroid, so they take on the shape 262', as described.

Referring once again to circuit board drawings illustrated in FIGS. 47, 48, 48A, 49 and 50, one will appreciate that the attachment technology, by using ACFs, is equally applicable to all of the drawings and variations illustrated in U.S. Pat. No. 7,957,806; U.S. Ser. No. 12/407,402; U.S. Pat. Nos. 8,195,295; 9,895,534; Patent Publication 2015/024,5468; 2015/0245468 and U.S. Pat. No. 9,521,744, the contents of all of which are incorporated herein fully by reference. It will be further appreciated that any of the noble gold pocket pads that are associated with an AIMD ferrule in accordance with the present invention, are fully or at least partially applicable to any of the patents that have been incorporated by reference.

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. All references cited in the "Detailed Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the apparatus and systems of this technology and, unless explicitly stated otherwise, are not intended to be a representation that given embodiments of this technology have, or have not, been made or tested.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. In addition, disclosure of ranges includes disclosure of all distinct values and further divided ranges within the entire range.

What is claimed is:

1. A filtered feedthrough that is attachable to an active implantable medical device (AIMD), the filtered feedthrough comprising:
   a) a titanium ferrule configured to be installed in an opening of a housing of the AIMD, the ferrule comprising:
      i) a conductive ferrule body separating a ferrule body fluid side end surface opposite a ferrule device side end surface, wherein, when the ferrule is installed in the opening of the AIMD housing, the ferrule body fluid side end surface and the ferrule device side end surface reside outside the housing and inside the housing, respectively;
      ii) at least one surface disposed on the ferrule device side end surface;
      iii) a ferrule opening passing through the at least one surface and extending to the ferrule body fluid side end surface and to the ferrule device side end surface; and
      iv) at least one pocket provided in the at least one surface disposed on the ferrule device side end surface; and
   b) an insulator hermetically sealed in the ferrule opening by a first gold braze, the insulator having at least one via hole extending through the insulator to an insulator body fluid side and to an insulator device side, wherein the insulator comprises alumina ceramic;
   c) at least one conductive pathway disposed through and hermetically sealed to the insulator in the at least one via hole;
   d) a gold pocket-pad disposed within the at least one pocket in the ferrule device side end surface;
   e) wherein the first gold braze and gold pocket-pad do not physically touch one another; and
   f) a filter capacitor disposed on the ferrule device side end surface, the filter capacitor comprising:

i) at least one active electrode plate disposed parallel and spaced from at least one ground electrode plate, wherein the active and ground electrode plates are disposed within a capacitor dielectric substrate;
ii) a first passageway disposed through the capacitor dielectric substrate;
iii) a capacitor active metallization disposed within the first passageway and being electrically connected to the at least one active electrode plate, but in a non-conductive relation with the at least one ground electrode plate; and
iv) a capacitor ground metallization disposed on an outer surface of the capacitor dielectric substrate and being electrically connected to the at least one ground electrode plate, but in a non-conductive relation with the at least one active electrode plate; and
g) wherein the at least one conductive pathway is electrically connected to the capacitor active metallization; and
h) an electrical connection material electrically connecting the capacitor ground metallization to the gold pocket-pad disposed within the at least one pocket of the ferrule device side end surface.

2. The filtered feedthrough of claim 1, wherein the electrical connection material comprises a thermal-setting conductive adhesive or a solder.

3. The filtered feedthrough of claim 1, wherein the filter capacitor is selected from the group consisting of a feedthrough filter capacitor, a chip capacitor, an MLCC, an X2Y attenuator, an internally grounded feedthrough capacitor, a hybrid internally grounded feedthrough capacitor, and a chip capacitor, and wherein when the chip capacitor, the MLCC or the X2Y attenuator is mounted on a circuit board, the circuit board is disposed adjacent to at least one of the ferrule and the insulator.

4. The filtered feedthrough of claim 1, wherein the insulator is selected from the group consisting of an alumina ceramic, a glass, and a glass-ceramic, and wherein the glass seal or the glass-ceramic seal comprises a fusion seal or a compression seal.

5. The filtered feedthrough of claim 1, wherein:
a) a capacitor first perimeter surface of the filter capacitor extends outwardly beyond a ferrule first perimeter surface of the ferrule,
b) a capacitor second perimeter surface of the filter capacitor does not extend outwardly beyond a ferrule second perimeter surface of the ferrule,
c) the capacitor ground metallization is disposed on at least a portion of the capacitor second perimeter surface,
d) the at least one pocket is located adjacent to the ferrule second perimeter surface,
e) the capacitor first perimeter surface, the capacitor second perimeter surface, the ferrule first perimeter surface and the ferrule second perimeter surface are perpendicular to the at least one surface of the titanium ferrule,
f) the capacitor first perimeter surface is perpendicular to the capacitor second perimeter surface, and
g) the ferrule first perimeter surface is perpendicular to the ferrule second perimeter surface.

6. The filtered feedthrough of claim 1, wherein the at least one conductive pathway comprises a solid through pin.

7. The filtered feedthrough of claim 1, wherein the at least one conductive pathway comprises:

i) a first conductive leadwire having a first conductive leadwire first end disposed within the at least one via hole in the insulator and having a first conductive leadwire second end extending outwardly beyond the insulator body fluid side;
ii) a second conductive leadwire having a second conductive leadwire first end disposed within the at least one via hole in the insulator and having a second conductive leadwire second end extending outwardly beyond the insulator device side and being disposed within the first passageway of the filter capacitor;
iii) wherein the first conductive leadwire first end is in contact with or adjacent to the second conductive leadwire first end;
iv) wherein the first conductive leadwire is not the same material as the second conductive leadwire;
v) a second braze electrically connecting the first conductive leadwire first end to the second conductive leadwire first end;
vi) a third conductive leadwire having a third conductive leadwire first end disposed within the first passageway of the filter capacitor;
vii) wherein the third conductive leadwire first end is in contact with or adjacent to the second conductive leadwire second end;
viii) wherein a third conductive leadwire second end extends outwardly beyond the filter capacitor adjacent to the ferrule device side end surface and the insulator device side;
ix) wherein the third conductive leadwire is not the same material as the first conductive leadwire or the second conductive leadwire; and
x) a second electrical connection material electrically connecting the second conductive leadwire second end to the third conductive leadwire first end.

8. The filtered feedthrough of claim 1, wherein the at least one conductive pathway comprises:
i) a first conductive leadwire disposed through the at least one via hole in the insulator and having a first conductive leadwire first end extending outwardly beyond the insulator device side and being disposed within the first passageway of the filter capacitor, and having a first conductive leadwire second end extending outwardly beyond the insulator body fluid side;
ii) a second conductive leadwire having a second conductive leadwire first end disposed within the first passageway of the filter capacitor and having a second conductive leadwire second end extending outwardly beyond the filter capacitor on the device side;
iii) wherein the first conductive leadwire first end is in contact with or adjacent to the second conductive leadwire first end;
iv) wherein the first conductive leadwire is not of the same material as the second conductive leadwire; and
v) a second electrical connection material electrically connecting the first conductive leadwire first end to the second conductive leadwire first end.

9. The filtered feedthrough of claim 1, wherein the at least one conductive pathway comprises:
i) a first conductive leadwire having a first conductive leadwire first end disposed within the at least one via hole in the insulator and having a first conductive leadwire second end extending outwardly beyond the insulator body fluid side; and
ii) a second conductive leadwire having a second conductive leadwire first end disposed within the at least one via hole in the insulator and having a second conductive leadwire second end extending outwardly beyond the insulator device side and extending through the first passageway of the filter capacitor;

iii) wherein the first conductive leadwire first end is conductively connected to the second conductive leadwire first end, and iv) wherein the first conductive leadwire is not the same material as the second conductive leadwire.

10. The filtered feedthrough of claim 1, wherein the insulator comprises alumina ceramic, and wherein the at least one conductive pathway comprises a composite fill characterized as having been co-sintered with the alumina ceramic or a substantially pure platinum fill characterized as having been co-sintered with the alumina ceramic, the composite fill extending from a composite fill first end to a composite fill second end, wherein the composite fill first end is in contact with or adjacent to the device side of the insulator, and wherein the composite fill second end is in contact with or adjacent to the body fluid side of the insulator, wherein the composite fill comprises a ceramic reinforced metal composite comprising a mixture of alumina and platinum surrounding a substantially pure platinum fill or a metallic wire.

11. The filtered feedthrough of claim 1, wherein the insulator comprises alumina ceramic, and further including an adhesion layer attached to the insulator and a wetting layer attached to the adhesion layer, wherein the first gold braze is physically disposed between the wetting layer and the metallic ferrule, and wherein the adhesion layer comprises titanium and the wetting layer comprises at least one of molybdenum and niobium, or, wherein the adhesion layer and the wetting layer are formed as one layer.

12. A filtered feedthrough that is attachable to an active implantable medical device (AIMD), the filtered feedthrough comprising:
  a) a titanium ferrule configured to be installed in an opening of a housing of the AIMD, the ferrule comprising:
    i) a ferrule first end surface opposite a ferrule second end surface;
    ii) a ferrule opening extending to the ferrule first end surface and to the ferrule second end surface;
    iii) at least one pocket formed in the ferrule first end surface; and
    iv) a gold pocket-pad disposed within the at least one pocket; and
  b) an insulator hermetically sealed in the ferrule opening, the insulator having at least one via hole extending to an insulator first side and to an insulator second side, wherein the insulator first and second sides are adjacent to the ferrule first and second end surfaces, respectively, and wherein the hermetic seal of the insulator to the ferrule and the gold pocket-pad do not physically touch each other; and
  c) at least one conductive pathway disposed through and hermetically sealed to the insulator in the at least one via hole; and
  d) an internally grounded filter capacitor disposed on the ferrule device side end surface, the internally grounded filter capacitor comprising:
    i) a capacitor dielectric supporting at least one active electrode plate in a capacitive relationship with at least one ground electrode plate;
    ii) a first passageway disposed through the capacitor dielectric;
    iii) a capacitor active conductor disposed within the first passageway and being electrically connected to the at least one active electrode plate;
    iv) a second passageway disposed through the capacitor dielectric; and
    v) a capacitor ground conductor disposed within the second passageway and being electrically connected to the at least one ground electrode plate; and
  f) an active electrical connection material conductively connecting the at least one conductive pathway in the insulator to the capacitor active conductor; and
  g) a ground electrical connection material conductively connecting the capacitor ground conductor to the gold pocket-pad disposed within the at least one pocket in the ferrule device side end surface.

13. The filtered feedthrough of claim 12, wherein the insulator is hermetically sealed to the ferrule by one of the group consisting of a gold braze, a glass seal, and a glass-ceramic seal.

14. A feedthrough that is attachable to an active implantable medical device (AIMD), the feedthrough comprising:
  a) a titanium ferrule configured to be installed in an opening of a housing of the AIMD, the ferrule comprising:
    i) a ferrule first end surface opposite a ferrule second end surface;
    ii) a ferrule opening extending to the ferrule first end surface and to the ferrule second end surface;
    iii) at least one pocket formed in the ferrule first end surface; and
    iv) a gold pocket-pad disposed within the at least one pocket; and
  b) an insulator hermetically sealed in the ferrule opening by a first gold braze, the insulator having at least one via hole extending to an insulator first side and to an insulator second side, wherein the insulator first and second sides are adjacent to the ferrule first and second end surfaces, respectively, and wherein the first gold braze and gold pocket-pad do not physically touch each other; and
  c) at least one conductive pathway disposed through and hermetically sealed to the insulator in the at least one via hole.

15. The feedthrough of claim 14, wherein the at least one conductive pathway comprises a solid through pin.

16. The feedthrough of claim 14, further comprising a filter capacitor comprising:
  a) a capacitor dielectric supporting at least one active electrode plate in a capacitive relationship with at least one ground electrode plate;
  b) a first passageway extending through the capacitor dielectric;
  c) a capacitor active metallization disposed within the first passageway and being electrically connected to the at least one active electrode plate; and
  d) a capacitor ground metallization disposed on an outer surface of the capacitor dielectric and being electrically connected to the at least one ground electrode plate,
  f) wherein the at least one conductive pathway comprises:
    i) a first conductive leadwire having a first conductive leadwire first end disposed within the at least one via hole in the insulator and a first conductive leadwire second end extending outwardly beyond the insulator second side adjacent to the ferrule second end surface;
    ii) a second conductive leadwire having a second conductive leadwire first end disposed within the at least one via hole in the insulator and a second conductive leadwire second end extending outwardly beyond the insulator first side, the second conductive leadwire second end being disposed within the first passageway of the filter capacitor, wherein the first conductive leadwire first end is in contact with or adjacent to the second conductive leadwire first end, and wherein the first conductive leadwire is not the same material as the second conductive leadwire;
    iii) a second braze electrically connecting the first conductive leadwire first end to the second conductive leadwire first end; and
    iv) a third conductive leadwire having a third conductive leadwire first end disposed within the first passageway of the filter capacitor, wherein the third conductive leadwire first end is in contact with or adjacent to the second conductive leadwire second end, and wherein a third conductive leadwire second end extends outwardly beyond the filter capacitor adjacent to the ferrule device side end surface and the insulator device side; and
  g) a second electrical connection material electrically connecting the second conductive leadwire second end to the third conductive leadwire first end.

17. The feedthrough of claim 14, further comprising a filter capacitor comprising:
  a) a capacitor dielectric supporting at least one active electrode plate in a capacitive relationship with at least one ground electrode plate;
  b) a first passageway extending through the capacitor dielectric;
  c) a capacitor active metallization disposed within the first passageway and being electrically connected to the at least one active electrode plate; and
  d) a capacitor ground metallization disposed on an outer surface of the capacitor dielectric and being electrically connected to the at least one ground electrode plate,
  f) wherein the at least one conductive pathway comprises:
    i) a first conductive leadwire extending through the at least one via hole in the insulator and having a first conductive leadwire first end extending outwardly beyond the insulator first side and being disposed within the first passageway of the filter capacitor and having a first conductive leadwire second end extending outwardly beyond the insulator second side; and
    ii) a second conductive leadwire having a second conductive leadwire first end disposed within the first passageway of the filter capacitor and having a second conductive leadwire second end extending outwardly beyond the filter capacitor adjacent to the ferrule first end surface, wherein the first conductive leadwire first end is in contact with or adjacent to the second conductive leadwire first end, and wherein the first conductive leadwire is not the same material as the second conductive leadwire; and
  g) a second electrical connection material electrically connecting the first conductive leadwire first end to the second conductive leadwire first end.

18. The feedthrough of claim 14, further comprising a filter capacitor comprising:
  a) a capacitor dielectric supporting at least one active electrode plate in a capacitive relationship with at least one ground electrode plate;
  b) a first passageway extending through the capacitor dielectric;
  c) a capacitor active metallization disposed within the first passageway and being electrically connected to the at least one active electrode plate; and
  d) a capacitor ground metallization disposed on an outer surface of the capacitor dielectric and being electrically connected to the at least one ground electrode plate,
  f) wherein the at least one conductive pathway comprises:
    i) a first conductive leadwire having a first conductive leadwire first end disposed within the at least one via hole in the insulator and a first conductive leadwire second end extending outwardly beyond the insulator second side; and
    ii) a second conductive leadwire having a second conductive leadwire first end disposed within the at least one via hole in the insulator and a second conductive leadwire second end extending outwardly beyond the insulator first side and through the first passageway of the filter capacitor,
    iii) wherein the first conductive leadwire first end is conductively connected to the second conductive leadwire first end, and
    iv) wherein the first conductive leadwire is not of the same material as the second conductive leadwire.

19. The feedthrough of claim 14, wherein the at least one conductive pathway comprises a composite fill comprising a mixture of alumina and platinum surrounding a substantially pure platinum wire, the composite fill extending from a composite fill first end to a composite fill second end, wherein the composite fill first end is in contact with or adjacent to the insulator first side, and wherein the composite fill second end is in contact with or adjacent to the insulator second side.

20. The feedthrough of claim 14, wherein the ferrule includes a peninsula providing the at least one surface disposed on the ferrule first side and extending into the ferrule opening, wherein the at least one pocket and the gold pocket-pad reside in the at least one surface of the ferrule peninsula; and
  a) further including an internally grounded filter capacitor disposed on the insulator first side, the internally grounded filter capacitor comprising:
    i) at least one active electrode plate disposed parallel and spaced from at least one ground electrode plate, wherein the active and ground electrode plates are disposed within a capacitor dielectric substrate;
    ii) a first passageway disposed through the capacitor dielectric substrate perpendicular to the active and ground electrode plates;
    iii) a capacitor active conductor disposed within the first passageway and being electrically connected to the at least one active electrode plate, but in a non-conductive relation with the at least one ground electrode plate;
    iv) a second passageway disposed through the capacitor dielectric substrate perpendicular to the active and ground electrode plates; and
    v) a capacitor ground conductor disposed within the second passageway and being electrically connected to the at least one ground electrode plate, but in a non-conductive relation with the at least one active electrode plate; and
  b) an electrical connection material electrically connecting the capacitor ground conductor to the gold pocket-pad disposed within the at least one pocket in the at least one surface of the ferrule peninsula; and c) wherein the internally grounded filter capacitor does not have a ground metallization disposed on an outer surface of the capacitor dielectric substrate.

21. The feedthrough of claim 20, including a second pocket formed in the at least one surface of the ferrule, and further including a second gold pocket-pad disposed within the second pocket, wherein the internally grounded filter capacitor comprises a capacitor ground metallization disposed on at least a portion of an outer surface of the capacitor dielectric substrate and being electrically connected to the at least one ground electrode plate, and further including a second electrical connection material electrically connecting the capacitor ground metallization to the second gold pocket-pad.

22. The feedthrough of claim 14, wherein the ferrule includes a bridge providing the at least one surface disposed on the ferrule first side and extending across the ferrule opening, wherein the at least one pocket and gold pocket-pad reside in the at least one surface of the ferrule bridge; and
  a) further including an internally grounded filter capacitor disposed on the insulator first side, the internally grounded filter capacitor comprising:
    i) at least one active electrode plate disposed parallel and spaced from at least one ground electrode plate, wherein the active and ground electrode plates are disposed within a capacitor dielectric substrate;
    ii) a first passageway disposed through the capacitor dielectric substrate perpendicular to the active and ground electrode plates;
    iii) a capacitor active conductor disposed within the first passageway and being electrically connected to the at least one active electrode plate, but in a non-conductive relation with the at least one ground electrode plate;
    iv) a second passageway disposed through the capacitor dielectric substrate perpendicular to the active and ground electrode plates; and
    v) a capacitor ground conductor disposed within the second passageway and being electrically connected to the at least one ground electrode plate, but in a non-conductive relation with the at least one active electrode plate; and
  b) an electrical connection material electrically connecting the capacitor ground conductor to the gold pocket-pad disposed in the at least one pocket in the at least one surface of the ferrule bridge; and
  c) wherein the internally grounded filter capacitor does not have a ground metallization disposed on an outer surface of the capacitor dielectric substrate.

23. The feedthrough of claim 14, including a second pocket formed in the at least one surface of the ferrule and a second gold pocket-pad disposed within the second pocket;
  a) wherein the first pocket-pad and the second pocket-pad are disposed at opposite ends of the ferrule first end surface; and
  b) further including a hybrid internally grounded filter capacitor disposed on the insulator first side, the hybrid internally grounded filter capacitor comprising:
    i) at least one active electrode plate disposed parallel and spaced from at least one ground electrode plate, wherein the active and ground electrode plates are disposed within a capacitor dielectric substrate;
    ii) a first passageway disposed through the capacitor dielectric substrate perpendicular to the active and ground electrode plates;
    iii) a capacitor active conductor disposed within the first passageway and being electrically connected to the at least one active electrode plate, but in a non-conductive relation with the at least one ground electrode plate;
    iv) a second passageway disposed through the capacitor dielectric substrate perpendicular to the active and ground electrode plates;
    v) a capacitor ground conductor disposed within the second passageway and being electrically connected to the at least one ground electrode plate, but in a non-conductive relation with the at least one active electrode plate, wherein the capacitor ground conductor is electrically connected to the ferrule;
    vi) a first ground metallization disposed on at least a portion of a first outer surface of the capacitor dielectric substrate and being electrically connected to the at least one ground electrode plate; and
    vii) a second ground metallization disposed on at least a portion of a second outer surface of the capacitor dielectric substrate and being electrically connected to the at least one ground electrode plate; and
  c) a first electrical connection material electrically connecting the first gold pocket-pad to the first ground metallization; and
  d) a second electrical connection material electrically connecting the second gold pocket-pad to the second ground metallization.

24. The feedthrough of claim 14, including a filter disposed on the insulator first side,
  a) the filter being at least one of the group consisting of a chip capacitor, an MLCC, and an X2Y attenuator, the filter comprising:
    i) at least one active electrode plate disposed parallel and spaced from at least one ground electrode plate, wherein the active and ground electrode plates are disposed within a filter dielectric substrate;
    ii) a first filter metallization disposed on one end of the filter and being electrically connected to the at least one active electrode plate, but in a non-conductive relation with the at least one ground electrode plate; and
    iii) a second filter metallization disposed on another end of the filter and being electrically connected to the at least one ground electrode plate, but in a non-conductive relation with the at least one active electrode plate; and
  b) a first electrical connection material electrically connecting the first filter metallization to the at least one conductive pathway disposed through and hermetically sealed to the insulator in the at least one via hole; and
  c) a second electrical connection material electrically connecting the second filter metallization to the gold pocket-pad disposed in the at least one pocket of the ferrule;
  d) wherein the filter is attached to at least one of the insulator and the ferrule, or, wherein the filter is attached to a circuit board, and wherein the circuit board is disposed adjacent to at least one of the insulator and the ferrule.

25. The feedthrough of claim 24, wherein the circuit board comprises at least one electrically conductive ground plate, and wherein the capacitor metallization is in electrical communication with the at least one conductive pathway, and wherein the circuit board ground plate is in electrical communication with and disposed between the second capacitor metallization and the gold pocket-pad.

* * * * *

UNITED STATES PATENT AND TRADEMARK OFFICE
CERTIFICATE OF CORRECTION

PATENT NO. : 10,350,421 B2  
APPLICATION NO. : 15/943998  
DATED : July 16, 2019  
INVENTOR(S) : Robert A. Stevenson, Christine A. Frysz and Jason Woods It is certified that error appears in the above-identified patent and that said Letters Patent is hereby corrected as shown below:

In the Claims

Column 46, Line 65 (Claim 25) after the words "wherein the" insert the word --first--

Signed and Sealed this
Twenty-second Day of October, 2019

Andrei Iancu
*Director of the United States Patent and Trademark Office*